United States Patent
Shibuya et al.

(10) Patent No.: US 10,196,416 B2
(45) Date of Patent: *Feb. 5, 2019

(54) PROCESS FOR PRODUCING A PARTICULATE COMPOSITION COMPRISING CRYSTALLINE ALPHA, ALPHA-TREHALOSE DI-HYDRATE

(71) Applicant: HAYASHIBARA CO., LTD., Okayama-shi Okayama (JP)

(72) Inventors: Takashi Shibuya, Okayama (JP); Seisuke Izawa, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/905,407

(22) Filed: Feb. 26, 2018

(65) Prior Publication Data

US 2018/0179245 A1    Jun. 28, 2018

Related U.S. Application Data

(60) Division of application No. 15/653,131, filed on Jul. 18, 2017, now Pat. No. 9,938,311, which is a
(Continued)

(30) Foreign Application Priority Data

Sep. 21, 2011 (JP) .................................. 2011-206482
Jul. 30, 2012 (JP) .................................. 2012-168474

(51) Int. Cl.
  *C07H 3/04*  (2006.01)
  *C12P 19/12* (2006.01)
(Continued)

(52) U.S. Cl.
  CPC ................. *C07H 3/04* (2013.01); *C07H 1/00* (2013.01); *C12N 9/1074* (2013.01); *C12P 19/12* (2013.01);
(Continued)

(58) Field of Classification Search
  None
  See application file for complete search history.

(56) References Cited

U.S. PATENT DOCUMENTS 5,441,644 A    8/1995  Kinouchi
5,472,863 A   12/1995  Maruta et al.
(Continued)

FOREIGN PATENT DOCUMENTS

CN    1174200 A    2/1998
CN    1309570 A    8/2001
(Continued)

OTHER PUBLICATIONS

Jemli et al, The Cyclodextrin Glycosyltransferase of Paenibacillus pabuli US132 Strain: Molecular Characterization and Overproduction of the Recombinant Enzyme, hindawi publishing corporation, journal of biomedicine and biotechology (Year: 2008).*

(Continued)

*Primary Examiner* — Melvin C. Mayes
*Assistant Examiner* — Stefanie J Cohen
(74) *Attorney, Agent, or Firm* — Browdy and Neimark, PLLC

(57) ABSTRACT

A process for enabling the production of a particulate composition containing crystalline trehalose dihydrate is provided. Including allowing an α-glycosyltrehalose-forming enzyme to act on liquefied starch derived from a microorganism of the genus *Arthrobacter* and a trehalose-releasing enzyme derived from a microorganism of the genus *Arthrobacter* along with a starch debranching enzyme and a (Continued)

cyclomaltodextrin glucanotransferase; allowing glucoamylase to act on the resulting mixture to obtain a saccharide solution containing α,α-trehalose; precipitating crystalline α,α-trehalose dihydrate from the above saccharide solution; collecting the precipitated crystalline α,α-trehalose dihydrate by a centrifuge; and ageing and drying the collected crystals. Cyclomaltodextrin glucanotransferase derived from a microorganism of the genus *Paenibacillus* or a mutant enzyme thereof is used to increase the α,α-trehalose content in the saccharide solution to over 86.0% by weight, on a dry solid basis, without passing through a fractionation step by column chromatography.

6 Claims, 3 Drawing Sheets

Specification includes a Sequence Listing.

Related U.S. Application Data continuation of application No. 14/976,281, filed on Dec. 21, 2015, now Pat. No. 9,738,674, which is a division of application No. 14/346,410, filed as application No. PCT/JP2012/073266 on Sep. 12, 2012, now Pat. No. 9,657,045.

(51) Int. Cl.
    C12P 19/18    (2006.01)
    C07H 1/00     (2006.01)
    C12P 19/14    (2006.01)
    C12N 9/10     (2006.01)
    C12P 19/20    (2006.01)
    C13K 13/00    (2006.01)

(52) U.S. Cl.
    CPC .............. *C12P 19/14* (2013.01); *C12P 19/18* (2013.01); *C12P 19/20* (2013.01); *C12Y 204/01019* (2013.01); *C13K 13/007* (2013.01)

(56) References Cited

U.S. PATENT DOCUMENTS

| | | | |
|---|---|---|---|
| 5,723,327 A | 3/1998 | Ikegami et al. | |
| 5,919,668 A | 7/1999 | Mandai et al. | |
| 6,090,792 A | 7/2000 | Nishimoto et al. | |
| 6,699,845 B2 | 3/2004 | Oobae et al. | |
| 7,186,535 B1 * | 3/2007 | Yamamoto | C12N 9/90 |
| | | | 435/183 |
| 2002/0042393 A1 | 4/2002 | Oobae et al. | |
| 2002/0058101 A1 | 5/2002 | Ohashi et al. | |
| 2007/0218529 A1 | 9/2007 | Yamamoto et al. | |

FOREIGN PATENT DOCUMENTS

| | | |
|---|---|---|
| CN | 1740333 A | 3/2006 |
| CN | 101230407 A | 7/2008 |
| CN | 101538292 A | 9/2009 |
| EP | 0919564 A2 | 6/1999 |
| JP | 1994269289 A | 9/1994 |
| JP | 1995170977 A | 7/1995 |
| JP | 1995213283 A | 8/1995 |
| JP | 1996066187 A | 3/1996 |
| JP | 1996073504 A | 3/1996 |
| JP | 1996066188 A | 12/1996 |
| JP | 2000023699 A | 1/2000 |
| JP | 2000228980 A | 8/2000 |
| JP | 2004208637 A | 7/2004 |
| WO | 200003735 A1 | 1/2000 |

OTHER PUBLICATIONS

Tsuei-Yun Fang et al. "Protein Engineering of Sulfolobus solfataricus Maltooligosyltrehalose Synthase to Alter Its Selectivity" Journal of Agricultral and Food Chemistry. 55: 5588-5594 (2007).

Tsue-Yun Fang et al. "Identification of the Essential Catalytic Residues and Selectivity-Related Residues of Maltooligosyltrehalose Trehalohydrolase from the Thermophilic Archaeon Sulfolobus solfataricus ATCC 35092" Journal of Agricultural and Food Chemistry. 56:5628-5633 (2008).

Sonia Jemli et al. "The Cyclodextrin Glycosyltransferase of Paenibacillus pabuli US132 Strain: Molecular Characterization and Overproduction of the Recombinant Enzyme" Journal of Biomedicine and Biotechnology. 2008:692573:1-9 (2008).

Lee et al "Cyclodextrin glycosyltransferase" Database Uniprot [Online] XP002740175, Database accession No. C9WB02 (Jun. 28, 2011), accessed May 27, 2015.

Wakariyasui-Balch-Shoseki (Accessible batch crystallization), edited by Noriaki Kubota and published by the Society of Separation Process Engineers, Japan, pp. 32-47 (Apr. 30, 2010). English language translation of excerpt from pp. 34-35.

Jemli et al, The Cyclodextrin Glycosyltransferase of Paenibacillus pabuli US132 Strain: Molecular Characterization and Overproduction of the Recombinant Enzyme, 2008, Journal of Biomedicine and Biotechnology, Article ID 692573, 9 pages.

Bohlin et al., Application of controlled cooling and seeding in batch crystallization, The Canadian Journal of Chemical Engineering, 70:120-126 (1992).

"Database Unipro" Database accession No. C9WB02, cited in Korean Office Action, dated Apr. 25, 2018, in corresponding Korean Patent Application 10-2017-7024456.

* cited by examiner

PROCESS FOR PRODUCING A PARTICULATE COMPOSITION COMPRISING CRYSTALLINE ALPHA, ALPHA-TREHALOSE DI-HYDRATE

CROSS REFERENCE TO RELATED APPLICATION

This is application is a DIV of U.S. application Ser. No. 15/653,131, filed on Jul. 8, 2017, now U.S. Pat. No. 9,938,131, which is a CON of U.S. application Ser. No. 14/976,281, filed on Dec. 21, 2015, now U.S. Pat. No. 9,738,674, which is a DIV of U.S. application Ser. No. 14/346,410, filed May 21, 2014, now U.S. Pat. No. 9,657,045, filed as application No. PCT/JP2012/073266 on Sep. 12, 2012, each of which claim priority to JP2012-168474, filed Jul. 30, 2012 and JP2011-206482, filed Sep. 12, 2012 and all of which are incorporated herein in their entirety by this reference thereto.

TECHNICAL FIELD

The present invention relates to a process for producing a particulate composition containing crystalline α,α-trehalose dihydrate, particularly, to a process for producing a high-purity particulate composition containing crystalline α,α-trehalose dihydrate, which produces a particulate composition containing crystalline α,α-trehalose dihydrate from starch on an industrial scale and in a satisfactory yield through consistent steps, and to a particulate composition containing crystalline α,α-trehalose dihydrate obtained thereby.

BACKGROUND ART

Various methods have been conventionally known as processes for producing particulate compositions containing crystalline α,α-trehalose dihydrate ("α,α-trehalose" is abbreviated as "trehalose" throughout the specification, hereinafter). For example, Patent Literature 1 discloses a process for producing a particulate composition containing crystalline trehalose dihydrate by allowing β-amylase with or without a starch debranching enzyme to act on liquefied starch, allowing a maltose/trehalose converting enzyme to act on the resulting mixture to obtain a trehalose-containing saccharide solution, appropriately purifying the saccharide solution, and crystallizing trehalose; and Patent Literature 2 discloses a process for producing a particulate composition containing crystalline trehalose dihydrate by allowing an α-glycosyltrehalose-forming enzyme (another name "a non-reducing saccharide-forming enzyme") and a trehalose-releasing enzyme along with a starch debranching enzyme to act on liquefied starch, allowing glucoamylase to act on the resulting mixture to obtain a trehalose-containing saccharide solution, appropriately purifying the saccharide solution, and crystallizing trehalose.

Patent Literatures 3 and 4 disclose processes for producing particulate compositions containing crystalline trehalose dihydrate, which increase the trehalose content in the above-identified trehalose-containing saccharide solution by modifying the process disclosed in Patent Literature 2, wherein a starch debranching enzyme and a cyclodextrin glucanotransferase (abbreviated as "CGTase", hereinafter) are allowed to act on their substrates, with a combination use of an α-glycosyltrehalose-forming enzyme and a trehalose-releasing enzyme. Patent Literatures 5 and 6 disclose processes for producing particulate compositions containing crystalline trehalose dihydrate by allowing a thermostable α-glycosyltrehalose-forming enzyme derived from a microorganism of the genus *Sulfolobus* or a thermostable α-glycosyltrehalose-forming enzyme and a thermostable trehalose-releasing enzyme to act on liquefied starch to obtain a trehalose-containing saccharide solution, appropriately purifying the solution, and crystallizing trehalose.

Among these conventional production processes, in the case of combinationally using the enzymes disclosed in Patent Literatures 3 and 4, a trehalose-containing saccharide solution with a trehalose content of over 80% by weight, on a dry solid basis (d.s.b.), can be easily prepared from liquefied starch as a material with only enzymatic reactions without passing through a fractionation step by column chromatography, and has the merit that the trehalose-containing saccharide solution thus prepared has a satisfactory crystallizability of trehalose because the saccharide composition thereof is composed of almost glucose except for trehalose. Therefore, according to the above production processes disclosed in Patent Literatures 3 and 4, a relatively high-purity particulate composition containing crystalline trehalose dihydrate can be produced by precipitating crystalline trehalose dihydrate from the above trehalose-containing saccharide solution and subjecting the resulting mixture to a solid-liquid separation method by centrifugation to collect the crystals.

Particularly, in the above production processes disclosed in Patent Literatures 3 and 4, when the enzymes derived from microorganisms of the genus *Arthrobacter* are used as the α-glycosyltrehalose-forming enzyme and the trehalose-releasing enzyme, such enzymes can be distinctly advantageously used in producing a particulate composition containing crystalline trehalose dihydrate on an industrial scale because the above microorganisms can grow relatively fast and also have a high productivity of the above enzymes. Thus, the applicant of the present invention has now been producing "TREHA", a product name of a high-purity particulate composition containing crystalline trehalose dihydrate with a purity of at least 98.0% by weight as a product standard, commercialized by Hayashibara Co., Ltd., Okayama, Japan (called "a food-grade powder containing crystalline trehalose dihydrate", hereinafter), by using the enzymes derived from a microorganism of the genus *Arthrobacter* as the α-glycosyltrehalose-forming enzyme and the trehalose-releasing enzyme, and by the processes disclosed in Patent Literatures 3 and 4; and commercializing "TREHA" mainly as a material for food products, cosmetics, etc. At present, according to the above production process, however, the trehalose content in the trehalose-containing saccharide solution obtained by the enzymatic reactions remains at around about 85% by weight, d.s.b., and the trehalose yield against starch does not reach 40% by weight even when the enzymatic reaction conditions are variously optimized.

While, Non-Patent Literatures 1 and 2 disclose that a trehalose-containing saccharide solution with a trehalose content of about 87% by weight, d.s.b., is obtained by either allowing recombinant enzymes, which have been prepared by allowing respective genes for a thermostable α-glycosyltrehalose-forming enzyme, thermostable trehalose-releasing enzyme, and thermostable isoamylase derived from a microorganism of the species *Sulfolobus solfataricus* to express in *Escherichia coli* (*E. coli*), or allowing mutant enzymes, which have been constructed by additionally introducing site specific mutations into the above genes, to act on soluble starch.

However, since the soluble starch used as a material in Non-Patent Literatures 1 and 2, which is prepared by treating starch with an acid to remove amorphous parts in starch granules, is a quite specific and expensive material, the use of such soluble starch as a material for industrial scale production of a particulate composition containing crystalline trehalose dihydrate is costly, unlikely acceptable, even if an enzymatic reaction solution with an increased trehalose content is obtained. When the recombinant enzymes or mutant enzymes disclosed in Non-Patent Literatures 1 and 2 are allowed to act on not soluble starch but liquefied starch used in an industrial scale production, the trehalose content in the trehalose-containing saccharide solution obtained by the enzymatic reactions is understandably as below as about 87% by weight and is still remained at the level of about 85% by weight, and it cannot be expected to improve the yield of a particulate composition containing crystalline trehalose dihydrate against starch more than those of the current production processes.

Incidentally, if only the trehalose content in a trehalose-containing saccharide solution is merely increased to 86.0% by weight or more, a column fractionation using column chromatography can possibly be applied to the trehalose-containing saccharide solution to obtain a trehalose-rich fraction. When such a column fractionation is employed, the more the steps, the higher the production cost becomes, and moreover, an inevitable loss of trehalose contained in fractions other than collected fractions rich in trehalose may be induced and it cannot be avoided the reduction of the yield of a particulate composition containing crystalline trehalose dihydrate against starch by a large margin even if a trehalose-containing saccharide solution with a trehalose content of over 86.0% by weight, d.s.b., is obtained by the above column fractionation in such a manner of preparing a particulate composition containing crystalline trehalose dihydrate by collecting crystalline trehalose dihydrate precipitated from such a saccharide solution.

If only to simply increase the production yield against starch, the following so called total sugar method can be employed in place of employing the solid-liquid separation method for collecting precipitated crystals by centrifugation; a massecuite containing precipitated crystals is placed in a container and allowed to crystallize/solidify the total contents and pulverize the resultant to obtain a powder, or a massecuite is spray-dried to obtain a powder. However, in the case of such total sugar method, since even concomitants, which are characteristic to the method used, such as glucose contained in a massecuite are pulverized together with crystallized trehalose, the trehalose content in the resulting particulate composition containing crystalline trehalose dihydrate is not increased to a level more than the trehalose content in the massecuite, and a high-purity particulate composition containing crystalline trehalose dihydrate could not be obtained as a disadvantage.

Starch is a material that is now relatively abundant and easily available at a low price, however, it is not an inexhaustible substance and is limited in its total amount produced annually by humans on the earth. On the other hand, starch is extensively used and it has recently been used as a new fuel material for bioethanol, etc., as a recent increased demand for clean energy in addition to conventional uses for industries, food products, feeds, and food materials. Under these circumstances, the improvement of the production yield against starch for a product or a particulate composition containing crystalline trehalose dihydrate is quite important in terms of effective utilization of limited resources.

PRIOR ART LITERATURE

Patent Literature

[Patent Literature 1] Japanese Patent Kokai No. 170977/95
[Patent Literature 2] Japanese Patent Kokai No. 213283/95
[Patent Literature 3] Japanese Patent Kokai No. 73504/96
[Patent Literature 4] Japanese Patent Kokai No. 2000-228980
[Patent Literature 5] Japanese Patent Kokai No. 66188/96
[Patent Literature 6] Japanese Patent Kokai No. 66187/96

Non-Patent Literature

[Non-Patent Literature 1] *Journal of Agricultural and Food Chemistry*, Fang et al., Vol. 55, pp. 5588-5594, 2007
[Non-Patent Literature 2] *Journal of Agricultural and Food Chemistry*, Fang et al., Vol. 56, pp. 5628-5633, 2008

DISCLOSURE OF INVENTION

Object of the Invention

The present invention, which was made to solve the inconvenience in the above-identified conventional processes for producing particulate compositions containing crystalline trehalose dihydrate and to increase the yield of such a particulate compositions against starch while keeping the trehalose purity, has objects to provide a process for producing a particulate composition containing crystalline trehalose dihydrate that enables the production of a high-purity particulate composition containing crystalline trehalose dihydrate in a satisfactory yield through consistent steps using starch as a material, and to provide a novel particulate composition containing crystalline trehalose dihydrate produced by the process.

Means to Attain the Object

To overcome the above objects, the present inventors continued studying by considerations and repeated trial and error about the combination of the enzymes used in the above production methods disclosed in Patent Literatures 3 and 4, revealing that, when the enzymes derived from microorganisms of the genus *Arthrobacter*, which are easy to culture and high in enzyme productivity, are used as an α-glycosyltrehalose-forming enzyme and a trehalose-releasing enzyme, the use of a natural or recombinant CGTase derived from a microorganism of the genus *Paenibacillus* or a mutant enzyme thereof, in place of the CGTase derived from *Geobacillus stearothermophilus* Tc-91 strain (FERM BP-11273) that has been used so far, more efficiently proceeds a trehalose-forming reaction and improves the trehalose content in a trehalose-containing saccharide solution after glucoamylase treatment up to a level of, on a dry solid basis, over 86.0% by weight, preferably, 87.0% by weight or more without passing through a fractionation step by column chromatography. The trehalose-containing saccharide solution thus obtained is in conventional manner decolored, desalted, and concentrated before precipitating crystalline trehalose dihydrate, followed by collecting the resulting crystals by a centrifuge and ageing and drying the crystals to obtain a high-purity particulate composition containing crystalline trehalose dihydrate with a trehalose content of 98.0% by weight or more, d.s.b., in a higher production yield against starch than ever before. Thus, they accomplished the present invention.

The present invention solves the above objects by providing a process for producing a particulate composition containing crystalline trehalose dihydrate with a trehalose content of 98.0% by weight or more, d.s.b., characterized in that the process contains the steps of allowing, together with a starch debranching enzyme and CGTase, an α-glycosyl-trehalose-forming enzyme and a trehalose-releasing enzyme which are derived from a microorganism of the genus *Arthrobacter* to act on liquefied starch, allowing glucoamylase to act on the resulting mixture to obtain a trehalose-containing saccharide solution, precipitating crystalline trehalose dihydrate from the saccharide solution, collecting the precipitated crystalline trehalose dihydrate by a centrifuge, and ageing and drying the crystals, wherein a natural or recombinant CGTase derived from a microorganism of the genus *Paenibacillus* or a mutant thereof is used as the above CGTase to increase the trehalose content in the above saccharide solution to over 86.0% by weight, d.s.b., without passing through a fractionation step by column chromatography.

According to the present inventors' confirmation, the particulate composition containing crystalline trehalose dihydrate produced by the above process of the present invention is in no way inferior to a conventional food-grade powder containing crystalline trehalose dihydrate in view of its satisfactory trehalose purity and free-flowing ability, and it can be used as a material for food products and cosmetics similar to a conventional food-grade powder containing crystalline trehalose dihydrate.

Examples of the above microorganism of the genus *Paenibacillus* as a source for CGTase include those of the species *Paenibacillus illinoisensis, Paenibacillus pabuli,* and *Paenibacillus amylolyticus,* among which those of the species *Paenibacillus illinoisensis* and *Paenibacillus pabuli* are preferable in that they produce CGTases having an effect of highly improving the trehalose content in an enzymatic reaction solution in the formation reaction of trehalose, particularly, those of the species *Paenibacillus illinoisensis* are preferable.

As the above CGTases, those which have the following partial amino acid sequences of (a) to (d) are preferably used:

```
(a)     Gly-Ser-X₁-Ala-Ser-Asp;

(b)     Lys-Thr-Ser-Ala-Val-Asn-Asn;

(c)     Lys-Met-Pro-Ser-Phe-Ser-Lys;
and (d)     Val-Asn-Ser-Asn-X₂-Tyr.
```

(Wherein $X_1$ means Ala or Ser and $X_2$ means Ala or Thr, respectively.)

Examples of more preferable CGTases usable in the present invention are those which have any one of the amino acid sequences represented by SEQ ID NOs: 1, 2, 3, 12 and 13.

The present inventors further repeated trial and error and revealed that, when crystalline trehalose dihydrate is precipitated from the above trehalose-containing saccharide solution with a trehalose content of, on a dry solid basis, over 86.0% by weight, preferably, 87.0% by weight or more, the production yield of the resulting particulate composition containing crystalline trehalose dihydrate against starch can be more increased by applying thereunto the later described controlled cooling method or semi-controlled cooling method, compared to the case of precipitating crystalline trehalose dihydrate by an unforced cooling method for cooling the temperature of a trehalose-containing saccharide solution by leaving it to nature. In detail, the present invention also solves the above objects by providing a process for producing a particulate composition containing crystalline trehalose dihydrate, wherein the above step for precipitating crystalline trehalose dihydrate is effected by a controlled cooling method or semi-controlled cooling method.

The reason why the production yield against starch is increased by the application of such a controlled cooling method or semi-controlled cooling method is uncertain, however, it can be speculated that any of these methods can inhibit both a rapid increment of saturation degree and a formation of secondary crystal nuclei by cooling to form a plurality of substantially homogeneous-sized minute crystal nuclei in the early phase of crystallization, and can grow a plurality of homogeneous-sized crystal nuclei all together by promptly cooling a plurality of roughly homogeneous-sized crystal nuclei in the late phase of crystallization, and therefore a massecuite containing crystals with a lesser amount of microcrystals and a uniform granule size is obtained to facilitate the recovery of crystals by centrifugation, and the recovered crystals can be washed with a relatively small amount of water to reduce the loss of trehalose when in washing.

In addition, the present inventors found that the particulate composition containing crystalline trehalose dihydrate prepared by applying a controlled cooling method or semi-controlled cooling method to the precipitation of crystalline trehalose dihydrate similarly as in the above is surprisingly superior in that it is hardly cakeable compared to a particulate composition containing crystalline trehalose dihydrate and a conventional food-grade powder containing crystalline trehalose dihydrate, which are prepared by an unforced cooling method. They confirmed that these superior properties are due to the differences in the purity of trehalose and the degree of crystallinity for crystalline trehalose dihydrate of a particulate composition containing crystalline trehalose dihydrate, and thus they accomplished the present invention for a particulate composition containing crystalline trehalose dihydrate per se.

More specifically, the present invention solves the above objects by providing a particulate composition containing crystalline trehalose dihydrate, obtained by the process of employing a controlled cooling method or semi-controlled cooling method in precipitating crystalline trehalose dihydrate, which contains, on a dry solid basis, 99.0% by weight or more but not more than 99.6% by weight of trehalose and has a degree of crystallinity for crystalline trehalose dihydrate of 90.0% or higher but not higher than 96.0% when determined on its powder X-ray diffraction profile.

For reference, a particulate composition containing crystalline trehalose dihydrate, which contains, on a dry solid basis, 99.0% by weight or more but not more than 99.6% by weight of trehalose and has a degree of crystallinity for crystalline trehalose dihydrate of 90.0% or higher but not higher than 96.0% when determined on its powder X-ray diffraction profile, is a novel particulate composition distinguishable from a conventional food-grade powder containing crystalline trehalose dihydrate in that it has a significantly higher degree of crystallinity for crystalline trehalose dihydrate than that of a conventional food-grade powder containing crystalline trehalose dihydrate even though the trehalose content is substantially the same or a slightly higher level than that of a conventional food-grade powder containing crystalline trehalose dihydrate.

The reason why a hardly cakeable particulate composition containing crystalline trehalose dihydrate is obtained by applying a controlled cooling method or semi-controlled cooling method is uncertain, however, it can be speculated that the increment of both the purity of trehalose and the degree of crystallinity for crystalline trehalose dihydrate may Effect on the above because, as described above, a massecuite that contains crystals with a lesser amount of microcrystals and a homogeneous granule size is obtained by such a controlled cooling method or semi-controlled cooling method. This speculation can also be evidenced even by the fact that the degree of crystallinity for crystalline trehalose dihydrate of the particulate composition containing crystalline trehalose dihydrate of the present invention, obtained by applying a controlled cooling method or semi-controlled cooling method, is significantly higher than that of a particulate composition obtained by an unforced cooling method and a conventional food-grade powder containing crystalline trehalose dihydrate.

Effect of the Invention

According to the process of the present invention, a high-purity particulate composition containing crystalline trehalose dihydrate can be obtained in a satisfactory production yield against starch and on an industrial scale by consistent steps of using starch as a material and an α-glycosyltrehalose-forming enzyme and a trehalose-releasing enzyme derived from a microorganism of the genus *Arthrobacter* that is easily cultured and high in enzyme productivities. Accordingly, the process imparts an advantageous contribution to the effective use of starch resources as a material. In particular, when a controlled cooling method or semi-controlled cooling method is applied in precipitating crystalline trehalose dihydrate from a trehalose-containing saccharide solution, the production yield of a produced particulate composition, containing crystalline trehalose dihydrate, against starch is more improved as a merit. The particulate composition containing crystalline trehalose dihydrate produced by the process of the present invention, which applies a controlled cooling method or semi-controlled cooling method, is a superior particulate composition in that it is hardly cakeable and high in both trehalose purity and degree of crystallinity for crystalline trehalose dihydrate, compared to a conventional food-grade powder containing crystalline trehalose dihydrate.

BEST MODE FOR CARRYING OUT THE INVENTION

1. Definition of Terms

Figure 1:
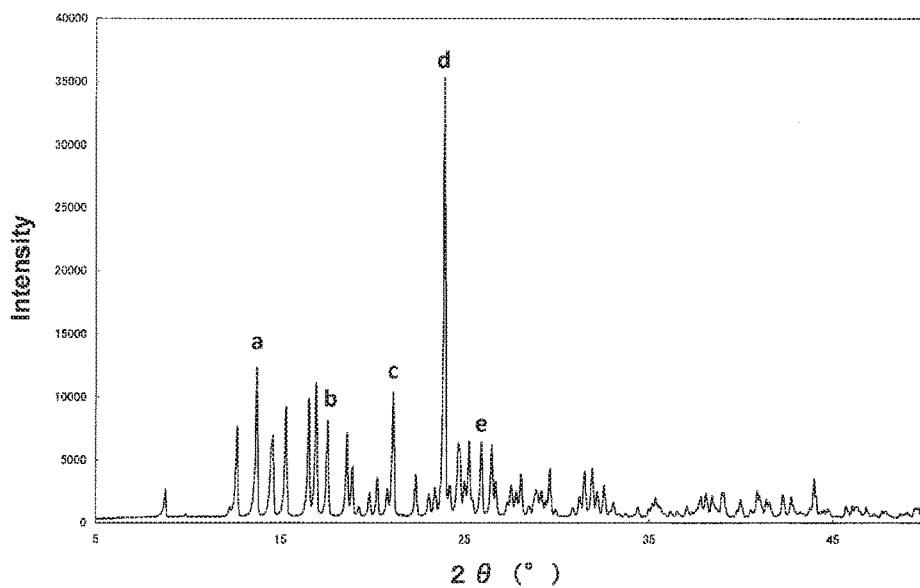
FIG. 1 is an example of a powder X-ray diffraction pattern with a characteristic X-ray for a particulate composition containing crystalline trehalose dihydrate, which substantially consists of crystalline trehalose dihydrate.

Throughout the specification, the following terms mean as follows:

<Production Yield Against Starch>

The term "production yield against starch" as referred to in the specification is expressed by a percentage (%) for the rate of the weight, d.s.b., of a particulate composition containing crystalline trehalose dihydrate per unit mass, d.s.b, of a material starch. The specification assumes that a particulate composition containing crystalline trehalose dihydrate is produced by consistent steps of allowing enzymes to act on starch as a material to form trehalose, crystallizing the formed trehalose, and then collecting, ageing, and drying the crystallized trehalose; and the meaning of "production yield against starch" as referred to in the specification means the production yield of a particulate composition containing crystalline trehalose dihydrate, which is produced from the firstly precipitated crystals, i.e., the first-stage crystals precipitated from a trehalose-containing saccharide solution obtained by allowing enzymes to act on starch, against the starch; and it does not include any particulate composition containing crystalline trehalose dihydrate produced by recrystallization from a saccharide solution remained after collecting the precipitated crystals or from the one returned with a syrup separated from a massecuite, i.e., it does not include any particulate composition containing crystalline trehalose dihydrate prepared from the second and more stage crystals. For comparison, when crystallized by adding a seed crystal, the amount of the seed crystal is included in the amount of the obtained particulate composition containing crystalline trehalose dihydrate, when calculating the production yield against starch, throughout the specification.

<CGTase Activity>

The term "CGTase activity" as referred to in the specification is defined as follows: To five milliliters of an aqueous substrate solution containing 0.3% (w/v) of a soluble starch, 20 mM acetate buffer (pH 5.5), and 1 mM calcium chloride is added 0.2 ml of an enzyme solution diluted appropriately, and the resulting substrate solution is kept at 40° C. and sampled at 0 min and 10 min after initiating the enzymatic reaction in respective amounts of 0.5 ml, followed by immediately adding 15 ml of 0.02 N sulfuric acid solution to each sample to stop the enzymatic reaction. Each of the resulting sulfuric acid solutions is admixed with 0.2 ml of 0.1 N iodine solution to develop colors, and, after 10 min, the colored solutions are respectively measured for absorbance at a wavelength of 660 nm by a spectrophotometer, followed by calculating for starch decomposing activity with the following Formula [1]. One unit activity of CGTase is defined as the enzyme amount that completely diminishes the iodine color of a solution containing 15 mg of starch.

Formula [1]:

$$\text{Activity (unit/ml)} = \frac{Aa - Ab}{Aa} \times \frac{1}{0.2} \times (\text{dilution rate}) \quad \text{[Equation 1]}$$

Note: "Aa" means the absorbance at a wavelength of 660 nm of a reaction solution at 0 min after initiating the enzymatic reaction.

"Ab" means the absorbance at a wavelength of 660 nm of a reaction solution at 10 min after initiating the enzymatic reaction.

<Controlled Cooling Method>

The term "controlled cooling method" as referred to in the specification means a method for precipitating crystals by "controlled cooling" and means a cooling method where the liquid temperature "T" at the time "t" is basically expressed by Formula [7], wherein "τ" is the operation time established for a crystallization step, "$T_0$" is the liquid temperature at the initiation of crystallization, and "$T_f$" is the targeted liquid temperature at the termination of crystallization.

Formula [2]:

$$T = T_0 - (T_0 - T_f)(t/\tau)^3 \quad \text{[Equation 2]}$$

Figure 5:
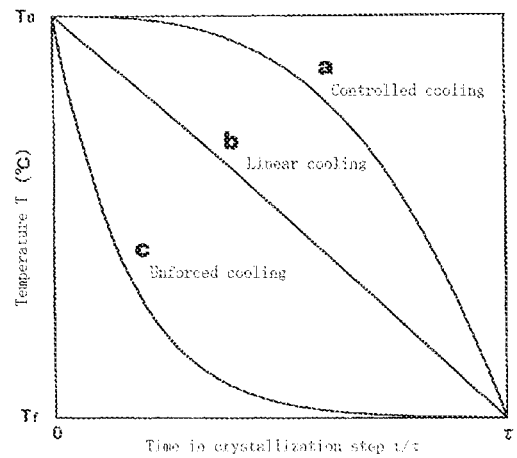
FIG. 5 is a figure of cooling patterns.

A controlled cooling method is expressed with "a" in FIG. 5, when expressed with a graph that describes concretely (schematically) the controlled cooling method, wherein the abscissa axis corresponds to the operation time settled for a crystallization step and the longitudinal axis corresponds to the liquid temperature when in crystallization. As shown in the symbol "a" in FIG. 5, according to a controlled cooling method, the liquid temperature gradually decreases in the early phase of crystallization at which the liquid temperature is relatively high but the liquid temperature promptly decreases in the later phase at which the liquid temperature has decreased to some extent. Accordingly, at the time of t=τ/2, i.e., the liquid temperature "$T_m$" at the middle point of crystallization step is maintained at least on the connection of $T_m > [(T_0 - T_f)/2 + T_f]$ (or the temperature change at the middle point of crystallization step becomes less than 50% of the total temperature change). In the changing pattern of the liquid temperature against time, the controlled cooling method is clearly distinguished from both a linear cooling method (the symbol "b" in FIG. 5) where the liquid temperature linearly decreases with the time "τ" from the liquid temperature $T_0$ to $T_f$, and a usual unforced-cooling method (the symbol "c" in FIG. 5) where the liquid temperature decreases exponentially and promptly at the early phase of crystallization but gradually decreases at the more later phase of crystallization with a decreased liquid temperature. To alter the liquid temperature "T" as a function of the time "t" represented in the above Formula [2], for example, a commercialized general-purpose programmed constant circulator for crystallization system, etc., can be used.

When such a controlled cooling method is applied in crystallization step, the cooling of the liquid temperature is gradually carried out at the early phase of crystallization after the addition of seed crystals of trehalose, and this inhibits both a prompt increment of the saturation degree of trehalose and a secondary crystal nucleation by cooling and results in a predominant growth of crystals from the added seed crystals as crystal nuclei. Meanwhile, in the later phase of crystallization at which crystals from the added seed crystals as crystal nuclei have been homogeneously generated, the homogeneously formed crystals are allowed to grow all together when the liquid temperature is promptly cooled, and therefore it gives the merit that a controlled cooling method affords a massecuite containing crystals with a homogeneous particle size and a lesser amount of microcrystals. For reference, "controlled cooling method" is described in detail in "*Wakariyasui-Batch-Shoseki*" (Accessible batch crystallization), edited by Noriaki KUBOTA, published by The Society of Separation Process Engineers, Japan, published on Apr. 30, 2010, pp. 32-47.

<Semi-Controlled Cooling Method>

The term "semi-controlled cooling method" as referred to in the specification means literally a semi-cooling-method of the above-identified controlled cooling method, wherein the liquid temperature "T" is not strictly altered against the time "t" according to the above Formula [2], and more specifically it means a cooling method, wherein the liquid temperature "T" is allowed to linearly or stepwisely decrease against the time "t" in order to keep the variation ($T_0 - T_m$) of the liquid temperature "T" at the point of "t=τ/2" to be at least 5% but less than 50% of the total temperature change ($T_0 - T_f$), preferably, at least 10% but less than 30%, because, varying depending on the purity, concentration, saturation degree, and seed-crystal content of trehalose in a solution containing trehalose used in crystallization, it is preferable that crystal nuclei are almost completely generated at the operation time "t=τ/2" (at the middle point in crystallization step). In the case of allowing the liquid temperature "T" to linearly or stepwisely decrease against the time "t" so as to adjust the variation ($T_0 - T_m$) of the liquid temperature "T" at the point of "t=τ/2" to be at least 5% but less than 50% of the total temperature change ($T_0 - T_f$), the liquid temperature "T" gradually decreases against the time "t" at early phase of crystallization, where the liquid temperature is relatively high, while the liquid temperature "T" promptly decreases against the time "t" at a later phase of crystallization, where the liquid temperature has decreased to some extent. As a result, it may be somewhat inferior to a controlled cooling method, however, a semi-controlled cooling method exerts substantially the same merits as the controlled cooling method, wherein the semi-controlled cooling method enables to provide a massecuite containing crystals with a lesser amount of microcrystals and a homogeneous particle size.

Concretely speaking, for example, the liquid temperature "T" is allowed to linearly or stepwisely decrease against the time "t" in such a manner of dividing the operation time "τ" into at least two, preferably, at least three zones and then, in a zone of early phase of crystallization step, allowing the thermal gradient in cooling to change gradually (to slow the cooling rate); and as it changes from the early phase or from the middle phase to the later phase, allowing the thermal gradient to increase (to fasten the cooling rate) to make the variation ($T_0 - T_m$) of the liquid temperature "T" at the point of "t=τ/2" to be at least 5% but less than 50% of the total temperature change ($T_0 - T_f$), preferably, at least 10% but less than 30%. In the case that the variation ($T_0 - T_m$) of the liquid temperature "T" at the point of "t=τ/2" is at least 50% of the total temperature change ($T_0 - T_f$), the cooling rate in the early phase of crystallization step is so fast as to possibly promptly increase the saturation degree by cooling to form the secondary crystal nuclei, while in the case of less than 5%, the cooling rate in the early phase of crystallization step is so slow as to get into the later phase of crystallization step, where a prompt cooling will start before the completion of forming crystals from crystal nuclei that have not been sufficiently formed from the added seed crystals. In any event, it becomes impossible to obtain a massecuite containing crystals with a lesser amount of microcrystals and a homogeneous particle size.

To conduct the controlled cooling method as described above, the liquid temperature "T" should be changed as a function of the time "t" represented in Formula [2], and an apparatus or a crystallizer, which can control the liquid temperature by a predetermined program, is essential; however, according to a semi-controlled cooling method, the liquid temperature "T" can be linearly or stepwisely decreased against the time "t" so as to adjust the variation $(T_0-T_m)$ of the liquid temperature "T" at the point of "$t=\tau/2$" to a level of at least 5% but less than 50% of the total temperature change $(T_0-T_f)$, preferably, at least 10% but less than 30% so that such a semi-controlled cooling method has the merit that it can be relatively easily conducted even in the case that there is no facility that controls the liquid temperature accurately.

<Degree of Crystallinity>

The term "a degree of crystallinity for crystalline trehalose dihydrate" as referred to in the specification means a value defined by the following Formula [3].

Formula [3]:

$$\text{Degree of crystallinity (\%)} = \frac{Hs - H_0}{H_{100} - H_0} \times 100 \quad \text{[Equation 3]}$$

$H_{100}$: An analytical value for a degree of crystallinity, determined based on the powder X-ray diffraction profile for a powdered standard sample containing crystalline trehalose dihydrate, where the powdered standard sample consists substantially of crystalline trehalose dihydrate.

$H_0$: An analytical value for a degree of crystallinity, determined based on the powder X-ray diffraction profile for a powdered standard sample containing trehalose, where the powdered standard sample consists substantially of an amorphous form of trehalose.

Hs: An analytical value for a degree of crystallinity, determined based on the powder X-ray diffraction profile for, as a test sample, a powder containing trehalose.

In Formula [3], the powder X-ray diffraction profiles for the basis of determining analytical values $H_{100}$, $H_0$, and Hs can be usually determined by a powder X-ray diffractometer equipped with a reflective or transmissive optical system. The powder X-ray diffraction profiles contain data for diffraction angles and diffraction strengths of crystalline trehalose dihydrate contained in a test or standard sample. Examples of methods for determining the analytical data for the degrees of crystallinity of such samples include the Hermans' method, Vonk's method, etc. Among which the Hermans' method is preferable because of its easiness and accuracy. Since these analytical methods have now been provided as computer softwares, any powder X-ray diffractometers, equipped with an analytical apparatus installed with any of the above computer softwares, can be suitably used.

As "a powdered standard sample containing crystalline trehalose dihydrate, where the powdered standard sample consists substantially of crystalline trehalose dihydrate", for determining the analytical value $H_{100}$, there must be used a crystalline trehalose dihydrate in the form of a powder or a single crystal, which has a trehalose purity of 99.9% by weight or higher (throughout the specification, "% by weight" is abbreviated as "%", unless specified otherwise but the "%" affixed to the degree of crystallinity should not be limited thereunto), exhibits characteristic diffraction peaks inherent to crystalline trehalose dihydrate on its powder X-ray diffraction pattern, and consists substantially of crystalline trehalose dihydrate. Examples of those in the form of a particulate composition or a single crystal include "TREHALOSE 999" (Code No: TH224, a trehalose purity of at least 99.9%), a product name of a particulate composition containing crystalline trehalose dihydrate, commercialized by Hayashibara Co., Ltd., Okayama, Japan, or sold by the present applicant as an analytical reagent; and those in the form of a particulate composition containing crystalline trehalose dihydrate or in the form of a single crystal, obtained by recrystallizing the above product. For reference, when analyzed with a computer software for the Hermans' method, the powder X-ray diffraction profile of a particulate composition containing crystalline trehalose dihydrate, as the above-identified powdered standard sample, which consists substantially of crystalline trehalose dihydrate, gives an analytical value $H_{100}$, usually, ranging from about 50.6% to about 50.9%.

As "a powdered standard sample containing trehalose, where the powdered standard sample consists substantially of an amorphous form of trehalose" for determining the analytical value $H_0$, the one, which has a trehalose purity of 99.9% or higher and consists substantially of amorphous trehalose, is used. Examples of such a powdered standard sample include those which are obtained by dissolving the above-identified powdered standard sample for determining the aforesaid analytical value $H_{100}$ in an appropriate amount of refined water, concentrating the solution, freeze-drying the concentrate, and drying the resultant in vacuo up to give a moisture content of 2.0% or lower, when determined on the Karl Fischer method. With these treatments, it is known by experience that a particulate composition consisting substantially of an amorphous form of trehalose is obtained. In general, even a particulate composition consisting substantially of an amorphous form of trehalose, the analytical value should not necessarily be 0% because, when the particulate composition is subjected to a powder X-ray diffractometer and the resulting powder X-ray diffraction profile is analyzed on the Hermans' method, Vonk's method, etc., a part of the scattering light, derived from the amorphous form inherent to the algorithm of a computer software for operating the analytical methods, is calculated. For reference, when analyzed with a computer software for the Hermans' method, the powder X-ray diffraction profile of the particulate composition containing trehalose, as the above-identified powdered standard sample, which consists substantially of an amorphous form of trehalose, gives an analytical value $H_0$, usually, ranging from about 8.5% to about 8.7%.

<Average Crystallite Diameter>

In general, a powder particle is recognized as being constituted by a plurality of single crystals, i.e., crystallites. The size of crystallite (crystallite diameter) in a powder containing crystals is speculated to be reflected in its property. The term "an average crystallite diameter for crystalline trehalose dihydrate" (called simply "crystallite diameter", hereinafter) as referred to in the present invention means an average of crystallite diameters calculated in such a manner of subjecting a particulate composition containing crystalline trehalose dihydrate to the powder X-ray diffraction analysis; selecting five diffraction peaks from among diffraction peaks detected on the obtained powder X-ray diffraction patterns, i.e., diffraction peaks (the symbols "a" to "e" in FIG. 1) at diffraction angles (2θ) of 13.7° (Miller's index (hkl): 101), 17.5° (Miller's index (hkl): 220), 21.1° (Miller's index (hkl): 221), 23.9° (Miller's index (hkl): 231), and 25.9° (Miller's index (hkl): 150), which located in a relatively low-angle region that is to be least disruptive to diffraction peak width due to heterogeneous strain of crystallite, and which were well separated from other diffraction peaks; calibrating the respective half widths (full widths at half maxima) and the diffraction angles based on the measured values determined when silicon ("Si640d", provided by NIST: National Institute of Standards and Technology, as a standard sample for X-ray diffraction) is used as a standard sample; and calculating respective averages of crystallite diameters with the Scherrer's equation shown in the following Formula [4]:

Formula [4]:

$$D = \frac{K\lambda}{B\cos\theta} \qquad \text{[Equation 4]}$$

D: Size of crystallite (Å)
λ: Wavelength of X-ray (Å)
β: Diffraction linewidth (rad)
θ: Diffraction angle (°)
K: Constant (0.9 when a half-width (a full-width at half maximum) is used for β)

Since a common powder X-ray diffractometer is installed with a computer software for calculating such crystallite diameters, an average crystallite diameter of crystalline trehalose dihydrate is relatively easily determined as long as a particulate composition containing crystalline trehalose dihydrate is available. Prior to powder X-ray diffraction analysis, each test sample is brayed in a mortar and sieved with a 53 µm sieve to obtain a powder passed through the sieve for use.

<Reducing Power>

The term "a reducing power of the whole particulate composition" as referred to in the specification can be obtained by using D-glucose as a standard substance; determining the reducing sugar content and the total sugar content, respectively, based on the D-glucose conversion, by the Somogyi-Nelson method and the anthrone-sulfuric acid method widely used in the art; and calculating the percentage (%) of the reducing saccharide content to the total sugar content in a particulate composition by using the following Formula [5].

Formula [5]:

$$\text{Reducing power (\%)} = \frac{\text{Reducing sugar content}}{\text{Total sugar content}} \times 100 \qquad \text{[Equation 5]}$$

<Particle Size Distribution>

The particle size distribution of a particulate composition is determined as follows in the specification: Metal sieves with opening sizes of 425, 300, 212, 150, 106, 75 and 53 µm, produced by Kabushiki Gaisha Iida Seisaku-sho, Tokyo, Japan, which are compliant with Japanese Industrial Standards (JIS Z 8801-1), are accurately weighed, stacked in the above-identified order, and mounted on "R-1", a product name of a ro-tap sieving shaker, produced by Kabushiki Gaisha Tanaka Kagaku Kikai Seisaku-sho, Osaka, Japan. A prescribed amount of weighed sample is placed on the uppermost sieve (having an opening size of 425 µm) in the stacked sieves, followed by shaking the sieves for 15 min while keeping the stacked state. Thereafter, each of the stacked sieves was accurately weighed again, and the weight of the sample collected on each of the sieves was determined by subtracting the weight of each of the sieves before loading on it the sample from the weight of the corresponding each of the sieves after shaking. Particle size distribution is expressed by calculating the weight percentage (%) of each of the weights of the particulate compositions with respective particle sizes collected on each of the sieves to the weight of the sample loaded on the uppermost sieve.

2. Process for Producing Crystalline Trehalose Dihydrate of the Present Invention The process of the present invention basically includes the following steps (1) to (6):

(1) a step of forming trehalose by allowing an α-glycosyltrehalose-forming enzyme and a trehalose-releasing enzyme, which are derived from a microorganism of the genus *Arthrobacter*, along with a starch debranching enzyme and a natural or recombinant CGTase or a mutant thereof to act on a liquefied starch solution to form trehalose;
(2) a step of treating with glucoamylase by allowing glucoamylase to act on the resulting reaction solution containing trehalose obtained in the step of forming trehalose;
(3) a step of purifying and concentrating the reaction solution containing trehalose by filtering, decoloring, desalting, and concentrating the reaction solution;
(4) a step of precipitating crystalline trehalose dihydrate by incorporating a seed crystal of crystalline trehalose dihydrate into the concentrate containing trehalose;
(5) a step of collecting a resulting crystalline trehalose dihydrate from the massecuite obtained in the precipitation step; and
(6) a step of ageing, drying, and optionally pulverizing the collected crystalline trehalose dihydrate.

The above steps (1) to (6) are subsequently explained below:

<Step (1) (Step of Forming Trehalose)>

This step is the one of allowing an α-glycosyltrehalose-forming enzyme and a trehalose-releasing enzyme, both of which are derived from a microorganism of the genus *Arthrobacter*, along with a starch debranching enzyme and a natural or recombinant CGTase or a mutant thereof to act on liquefied starch as a material to form trehalose.

The α-glycosyltrehalose-forming enzyme is an enzyme that forms α-glycosyltrehalose having a trehalose structure at the molecular terminus by acting on liquefied starch, while the trehalose-releasing enzyme is an enzyme that releases trehalose by acting on α-glycosyltrehalose. Accordingly, trehalose can be efficiently produced by allowing the α-glycosyltrehalose-forming enzyme and the trehalose-releasing enzyme along with a starch debranching enzyme to act on liquefied starch obtained by gelatinizing and liquefying starch.

Examples of the material starch used in producing trehalose include any of aboveground starches such as corn starch, rice starch, and wheat starch; subterranean starches such as potato starch, ocarina starch, and tapioca starch; and partial starch hydrolyzates obtained by partially hydrolyzing these starches with acids or amylases. The material starch is usually suspended in water into an about 10 to about 50% starch suspension and gelatinized/liquefied by heating in the presence of a thermostable α-amylase. The liquefaction degree of liquefied starch is usually controlled to a dextrose equivalent (DE) of less than 10, more particularly, less than 5.

Examples of the α-glycosyltrehalose-forming enzyme and the trehalose-releasing enzyme, which are derived from microorganisms of the genus *Arthrobacter*, include those disclosed in Japanese Patent Kokai No. 143876/95, Patent Literatures 2 to 4, etc. Recombinant α-glycosyltrehalose-forming enzymes and trehalose-releasing enzymes, which are disclosed in Japanese Patent Kokai Nos. 322880/95, 322883/95, 298887/95, and 298880/95, and Patent Literature 4, etc., can be used and positively modified mutant enzymes prepared by introducing site specific mutations into these enzymes can be also used. Particularly, an α-glycosyltrehalose-forming enzyme and trehalose-releasing enzyme, which are derived from *Arthrobacter* sp. S34 strain (FERN BP-6450) disclosed in Patent Literature 4 or derived from mutants thereof with high enzyme productivity, can be suitably used.

In the process of the present invention, isoamylase and pullulanase, which are widely used in the art, can be used as starch debranching enzymes. Any of commercialized enzyme preparations and those isolated from microorganisms can be used. Examples of such isoamylase include those which are derived from microorganisms of the species *Pseudomonas amyloderamosa* and *Myroides odoratus* are well known, particularly, an isoamylase specimen derived from a microorganism of the species *Pseudomonas amyloderamosa*, produced by Hayashibara Co., Ltd., Okayama, Japan, is preferable. Examples of pullulanase preparations include a pullulanase derived from a microorganism of the species *Klebsiella pneumoniae* commercialized by Hayashibara Co., Ltd., Okayama, Japan; and "PROMOZYME", a product name of a pullulanase derived from a microorganism of the species *Bacillus amylopullulyticus*, commercialized by Novozymes Japan Ltd., Tokyo, Japan.

The role of CGTase in the above steps of forming trehalose is to more proceed the above reaction of forming trehalose to more increase the trehalose content in the reaction solution by mainly converting maltooligosaccharides, having a glucose polymerization degree of four or lower, which are inevitably formed in the above trehalose-forming reaction process by an α-glycosyltrehalose-forming enzyme and a trehalose-releasing enzyme, into maltooligosaccharides, having a glucose polymerization degree of five or more, by a disproportionation reaction (an intermolecular rearrangement reaction of linear saccharides) catalyzed by CGTase.

CGTases have been isolated from different microorganisms and their functions and physicochemical properties have been revealed (see, for example, "*Kogyo-yo-Toshitsu-Handbook*" (Handbook of Industrial Enzyme for Saccharides), edited by Kodansha Scientific Ltd., Tokyo, Japan, published by Kodansha Ltd., Tokyo, Japan, pp. 28-32, 1999, etc). The genes for some of the above-identified CGTases have been cloned and the amino acid sequences have been determined based on the base sequences of the cloned genes. It has been also known that there exist four conserved regions that are recognized to commonly exist in the group of enzymes classified as α-amylase family on the amino acid sequences of the above CGTases. The CGTase protein derived from a microorganism of the species *Geobacillus stearothermophilus* has been already revealed its stereostructure by an X-ray crystal structural analysis, and the three catalytic residues of the CGTase, i.e., the $225^{th}$ aspartic acid residue (D225), the $253^{rd}$ glutamic acid residue (E253), and the $324^{th}$ aspartic acid residue (D324) in the amino acid sequence of SEQ ID NO:4 have been also revealed (see, for example, "*Kogyo-yo-Toshitsu-Koso-Handbook*" (Handbook of Industrial Enzyme for Saccharides), edited by Kodansha Scientific Ltd., Tokyo, Japan, published by Kodansha Ltd., Tokyo, Japan, pp. 56-63, 1999).

A natural or recombinant CGTase, derived from a microorganism of the genus *Paenibacillus*, or mutant enzymes thereof can be suitably used as CGTase in the process of the present invention. For example, CGTases derived from heretofore known strains of microorganisms of the species *Paenibacillus illinoisensis*, *Paenibacillus pabuli*, and *Paenibacillus amylolyticus*, and those derived from a microorganism of the genus *Paenibacillus*, isolated from the natural world, can be used as "a natural CGTase derived from a microorganism of the genus *Paenibacillus*" as referred to in the present invention. More concretely, CGTases derived from *Paenibacillus illinoisensis* NBRC15959 strain, *Paenibacillus illinoisensis* NBRC15379 strain, *Paenibacillus pabuli* NBRC13638 strain, and *Paenibacillus amylolyticus* NBRC15957 strain, and those derived from mutant strains thereof with high enzyme productivity, which are obtained by introducing mutations into the above microorganisms of the genus *Paenibacillus*, for example, by such as mutation treatments with ultraviolet irradiation and chemical substances, conventionally used in the art, are most suitably used. Further, "ALKALI CD AMYLASE", a product name of a CGTase derived from a microorganism of the species *Paenibacillus* sp., produced by Nagase ChemteX Corp., Osaka, Japan, can also be used as a CGTase derived from a microorganism of the genus *Paenibacillus*. Incidentally, CGTase, which has been conventionally used in producing a food-grade powder containing crystalline trehalose dihydrate, is the one derived from a microorganism of the species *Geobacillus stearothermophilus*.

In the process of the present invention, CGTases, having the following partial amino acid sequences of (a) to (d), are suitably used:

(a) Gly-Ser-$X_1$-Ala-Ser-Asp;

(b) Lys-Thr-Ser-Ala-Val-Asn-Asn;

(c) Lys-Met-Pro-Ser-Phe-Ser-Lys; and (d) Val-Asn-Ser-Asn-$X_2$-Tyr.

(Wherein $X_1$ means Ala or Ser and $X_2$ means Ala or Thr, respectively.)

The above partial amino acid sequences are characteristic of CGTases derived from microorganisms of the genus *Paenibacillus*.

As examples of "a recombinant CGTase derived from a microorganism of the genus *Paenibacillus*" as referred to in the present invention, those, which are obtained by cloning a CGTase gene derived from the above microorganism of the genus *Paenibacillus* and allowing to express the cloned CGTase gene in an appropriate host microorganism such as *E. coli* and *Bacillus subtilis*, can be suitably used. For comparison, CGTases derived from *Paenibacillus illinoisensis* NBRC15379 strain, *Paenibacillus pabuli* NBRC13638 strain, and *Paenibacillus amylolyticus* NBRC15957 strain are respectively cloned CGTase genes from these microorganisms by the present applicant independently and determined base sequences of the cloned genes, revealing that they have the amino acid sequences of SEQ ID NOs: 1, 2 and 3, respectively. The recombinant CGTases having any one of the amino acid sequences of SEQ ID NOs: 1 to 3 can be used similarly as a natural CGTase derived from a microorganism of the genus *Paenibacillus* in the process of the present invention.

As examples of "a mutant enzyme of a CGTase derived from a microorganism of the genus *Paenibacillus*" (abbreviated as "a mutant CGTase", hereinafter) as referred to in the present invention, mutant CGTases, into which deletion, replacement or addition of one or more amino acids are introduced into the amino acid sequence of the above microorganism within a range of not substantially altering substrate specificity and enzyme activity as CGTase, can be suitably used. The number of amino acid residues which can be deleted, replaced, or added in the amino acid sequence of such a mutant CGTase should not specifically be restricted as long as the substrate specificity and enzyme activity as CGTase can be retained, however, preferable are less than 5% of the amino acid sequence consisting of about 680 amino acid residues, i.e., amino acid residues of up to about 30, preferably, at least one but less than 20, more preferably, at least one but less than 10. Also referring to the mutation-introduced site on the amino acid sequence, it should not specifically be restricted as long as substrate specificity and enzyme activity as CGTase are substantially retained, however, there should desirably be avoided any mutation introduction to four conservative regions that are common in a group of enzymes classified as the alpha-amylase family and present on the amino acid sequence of CGTase, and to the above-identified partial amino acid sequences of (a) to (d) that are characteristic to CGTases derived from microorganisms of the genus *Paenibacillus*.

More concrete examples of "a natural or recombinant CGTase derived from a microorganism of the genus *Paenibacillus* or a mutant enzyme thereof" include the above-identified CGTases having any of the above-mentioned respective amino acid sequences of SEQ ID NOs: 1 to 3, and mutant CGTases having the amino acid sequence of SEQ ID NO: 12 or 13, prepared by introducing a site specific mutation into the CGTase gene of *Paenibacillus illinoisensis* NBRC15379 strain disclosed in the later described Example.

In the process of the present invention, the above-identified α-glycosyltrehalose-forming enzyme derived from a microorganism of the genus *Arthrobacter*, the above-identified trehalose-releasing enzyme derived from a microorganism of the genus *Arthrobacter*, a starch debranching enzyme, and a CGTase derived from a microorganism of the genus *Paenibacillus* are suitably added to liquefied starch (pH of about 4 to about 10) as a substrate in respective amounts of 0.5 to 10 units, 2.5 to 25 units, 50 to 1,000 units, and 0.5 to 50 units per gram starch at a temperature in the range of 30 to 60° C. for 10 to 100 hours. The trehalose content in the resulting reaction solution at the time upon termination of enzymatic reactions is usually about 86%, d.s.b.

<Step (2) (Step of Glucoamylase Treatment)>

This step is the one of further allowing a glucoamylase specimen to act on the reaction solution, obtained in the step (1) of forming trehalose, to increase the trehalose content, d.s.b. Incidentally, the reaction solution obtained in the step of forming trehalose contains, along with trehalose, saccharides such as D-glucose, maltose, maltooligosaccharides having a glucose polymerization degree of at least three, α-glucosyltrehalose, and α-maltosyltrehalose, and, when glucoamylase is allowed to act on the solution, maltose and maltooligosaccharides having a glucose polymerization degree of at least three can be hydrolyzed up to D-glucose, while α-glycosyltrehalose such as α-glucosyltrehalose and α-maltosyltrehalose can be hydrolyzed up to D-glucose and trehalose to increase the trehalose purity, i.e., the trehalose content, d.s.b., in the reaction solution.

Glucoamylases usable in the process of the present invention should not specifically be restricted depending on their sources and origins as long as they can hydrolyze maltose and maltooligosaccharides having a glucose polymerization degree of at least three up to D-glucose and also hydrolyze α-glycosyltrehalose such as α-glucosyltrehalose and α-maltosyltrehalose up to D-glucose and trehalose. Commercialized glucoamylase specimens, for example, such as "GLUCZYME AF6", a product name thereof commercialized by Amano Enzyme Inc., Aichi, Japan, and "GLUCOZYME", a product name thereof commercialized Nagase ChemteX Corp., Osaka, Japan, can be suitably used.

The trehalose content in the reaction solution after glucoamylase treatment or in the trehalose-containing saccharide solution is usually over 86.0%, d.s.b., preferably, 87.0% or higher. For comparison, when CGTase derived from a microorganism of the species *Geobacillus stearothermophilus* is used instead of using CGTase derived from a microorganism of the genus *Paenibacillus*, the trehalose content in the trehalose-containing saccharide solution after glucoamylase treatment is less than 86.0%, d.s.b., and never be 86.0% or higher.

<Step (3) (Step of Purification and Concentration)>

This step is the one of removing impurities by treating a trehalose-containing saccharide solution having an increased trehalose content, d.s.b., after glucoamylase treatment, with filtration, centrifugation, etc., in usual manner; decoloring the resulting saccharide solution with an activated charcoal; desalting the solution with a cation-exchange resin ($H^+$-form) and an anion-exchange resin ($OH^-$-form); and concentrating the resulting solution up to give a concentration suitable for crystallization. Since the trehalose content, d.s.b., in the reaction solution has been increased up to a level of 86.0% or higher through the step (2) of glucoamylase treatment, in the step (3) of purification and concentration, there requires no need of a step of further increasing the trehalose content, such as a fractionation step by column chromatography.

<Step (4) (Step of Crystallization)>

This step is the one of precipitating crystalline trehalose dihydrate from the trehalose-containing saccharide solution obtained through the steps (1) to (3) in the presence of a seed crystal of crystalline trehalose dihydrate. After the saccharide solution with a trehalose content, d.s.b., which had been increased up to a prescribed level, is usually controlled to give a saturation degree of trehalose in the range of 1.05 to 1.50, or controlled to give a trehalose concentration of about 60 to about 85% and to give a liquid temperature of about 40 to about 80° C., the resulting saccharide solution is transferred to a crystallizer, incorporated with a seed crystal of crystalline trehalose dihydrate in an amount usually equal to 0.1 to 5% (w/v), and particularly, 0.5 to 2% (w/v) of the volume of the resulting concentrated saccharide solution in the crystallizer, and the concentrated saccharide solution is unforcedly cooled to 5 to 60° C. over 3 to 48 hours under gentle stirring conditions to induce the precipitation of crystalline trehalose dihydrate. For comparison, when a seed crystal of crystalline trehalose dihydrate is already present in the crystallizer, etc., no additional seed crystal of crystalline trehalose dihydrate should specifically be required. The precipitation of crystalline trehalose dihydrate from the concentrated solution is, in view of work efficiency, usually effected in the presence of a seed crystal.

A controlled cooling method or semi-controlled cooling method can be advantageously used in the crystallization step, in place of the above unforced cooling method. In the case of conducting crystallization by such a controlled cooling method or semi-controlled cooling method, the trehalose-containing saccharide solution, which had been adjusted to a prescribed temperature through the above step (3), is transferred to a crystallizer, incorporated with a seed crystal of crystalline trehalose dihydrate in an amount equal to 0.1 to 5% (w/v), particularly, 0.5 to 2% (w/v) of the volume of the concentrated saccharide solution in the crystallizer, and allowed to effect crystallization by allowing the liquid temperature to gradually decrease in the early stage of the crystallization step and to promptly decrease in the later stage of the cooling step by controlling the cooling under gentle stirring conditions. The time required for crystallization varies depending on the amount of a seed crystal of crystalline trehalose dihydrate to be added; for example, in the case of a semi-controlled cooling method, the total cooling time is sectioned by at least two zones, preferably, at least three zones, and then, in each zone the temperature is roughly linearly decreased against time; the liquid temperature "T" is allowed to linearly or stepwise decrease against the time "t" in such a manner of allowing the variation $(T_0-T_m)$ of the liquid temperature "T" at the point of "$t=\tau/2$" to be at least 5% but less than 50% of the total temperature change $(T_0-T_f)$, preferably, at least 10% but less than 30%. For example, when crystals are precipitated by cooling the trehalose-containing saccharide solution from 60° C. to 20° C. over 10 hours, the cooling time is divided into two zones of 6 hours and 4 hours, where the solution is preferably cooled from 60° C. to 50° C. over 6 hours and then the solution is cooled from 50° C. to 20° C. over 4 hours, or the cooling time is divided into two zones of 7 hours and 3 hours, where the solution is also preferably cooled from 60° C. to 45° C. over 7 hours and then the solution is cooled from 45° C. to 20° C. over 3 hours. More preferably, the cooling time is divided into three zones of 4, 3 and 3 hours, and the solution is successively cooled from 60° C. to 55° C. over 4 hours in the first zone, cooled from 55° C. to 50° C. over 3 hours in the next zone, and cooled from 50° C. to 20° C. over 3 hours in the last zone.

In this way, according to a controlled cooling method or semi-controlled cooling method, a massecuite, which hardly generates microcrystals of crystalline trehalose dihydrate and contains crystals with a substantially homogeneous particle diameter, can be obtained, compared to a crystallization method that unforcedly cools the liquid solution without controlling the temperature. As a result, the production yield of the obtained crystalline trehalose dihydrate against starch can be more increased than that attained by an unforced cooling method. As described later, the obtained particulate composition containing crystalline trehalose dihydrate has characteristic features of having both a higher purity of trehalose and a higher degree of crystallinity for crystalline trehalose dihydrate that becomes to be an important index for cakeability than those of a powder obtained by an unforced cooling method. In the case of a controlled cooling method or semi-controlled cooling method, a particulate composition with more homogeneous particle size distribution is obtained as a merit, compared to a powder obtained by a crystallization method of unforced cooling.

<Step (5) (Step of Collection)>

This step is the one of collecting crystalline trehalose dihydrate by centrifugation according to a conventional solid-liquid separation method from the massecuite obtained in the crystallization step (4). The collected crystalline trehalose dihydrate is washed by spraying (showering) with a small amount of refined water to remove a syrup with amorphous saccharides, adhered to the surface of the crystalline trehalose dihydrate. The amount of refined water used for washing the crystals is preferably usually at least 3% but not more than 10% to the weight of a massecuite before centrifugation. When the amount of the above refined water is less than 3%, a sufficient washing could not be attained, resulting in remaining a syrup with amorphous saccharides and a fear of not obtaining a desired trehalose purity. On the contrary, when the amount of refined water used for washing is over 10%, the amount of crystalline trehalose dihydrate to be dissolved and removed by washing increases and results in a fear of decreasing the production yield against starch.

<Step (6) (Step of Ageing and Drying)>

This step is the one of obtaining a particulate composition containing crystalline trehalose dihydrate by allowing the collected crystalline trehalose dihydrate to stand in an atmosphere with a prescribed temperature and humidity for a prescribed period of time to age the crystals while drying with hot air. The product temperature of crystals, the relative humidity of atmosphere, and the retention time in the ageing and drying step are not specifically restricted as long as a desired particulate composition is obtained, however, the crystals should preferably be kept at a temperature of 20 to 55° C. as a product temperature and at an ambient relative humidity of 60 to 90%, and the ageing and drying time should preferably be about 5 to about 24 hours. The particulate composition obtained through the ageing and drying step is then unforcedly cooled down to an ambient temperature. The particulate composition can be advantageously forcedly cooled down to make the product temperature to give about ambient temperature by blowing to the contents a clean air with about ambient temperature. The particulate composition thus obtained can be used intact or optionally pulverized into a final product.

According to the process of producing the particulate composition containing crystalline trehalose dihydrate of the present invention, a trehalose-containing saccharide solution with a trehalose content of as high as over 86.0%, d.s.b., and it requires no fractionation step by column chromatography and there is no loss by fractionation. Thus, a particulate composition containing crystalline trehalose dihydrate can be obtained in a high production yield against starch. Since the process employs a separation method of centrifugally separating the precipitated crystals to remove a syrup containing impurities without employing a total sugar method of crystallizing a whole massecuite containing precipitated crystals and solidifying or spray-drying the resultant, the trehalose content in the resulting particulate composition containing crystalline trehalose dihydrate can be easily increased to a level of 98.0% or more to produce a high-purity particulate composition containing crystalline trehalose dihydrate.

When crystallization is effected by an unforced cooling method, the particulate composition containing crystalline trehalose dihydrate thus produced is substantially the same powder as a conventional food-grade powder containing trehalose in terms of the property of cakeability, etc., when stored, and it usually contains particles with a particle size of 53 μm or larger but smaller than 425 μm in an amount of 70% or more of the whole particulate composition and those with a particle size of 53 μm or larger but smaller than 300 μm in an amount of 50% or more of the whole particulate composition. When crystallization is effected by a controlled cooling method or semi-controlled cooling method, the particulate composition containing crystalline trehalose dihydrate produced by the process of the present invention is a significantly, hardly cakeable powder compared to the conventional food-grade powder containing trehalose, and it usually contains particles with a particle size of 53 μm or larger but smaller than 425 μm in an amount of 80% or more of the whole particulate composition and those with a particle size of 53 μm or larger but smaller than 300 μm in an amount of 60% or more of the whole particulate composition. The particulate composition containing crystalline trehalose dihydrate produced by the process of the present invention usually has a reducing power of 0.5% or lower when calculated by the above-mentioned Formula [5], and it is a superior particulate composition free of causing color change induced by browning even when incorporated into food products, pharmaceuticals, etc.

Accordingly, the particulate composition produced by the process of the present invention can be used intact or used after appropriately controlling the particle size as a powdered material for food products, cosmetics, quasi-drugs, pharmaceuticals, etc. In particular, as described above, the particulate composition containing crystalline trehalose dihydrate produced by the process of the present invention that employs a controlled cooling method when in crystallization is a significantly, hardly cakeable particulate composition compared to a conventional food-grade powder containing trehalose and it can be said to be a conventionally unknown, completely novel particulate composition containing crystalline trehalose dihydrate. The particulate composition has a superior merit that it can be incorporated into a single or plurality of other powdered materials for food products, cosmetics, quasi-drugs, pharmaceuticals, etc., in the fields of producing food products, cosmetics, quasi-drugs, and pharmaceuticals, which are produced by using production plants that are designed where powdered materials will be used on the premise.

The following experiments concretely explain the process for producing the particulate composition containing crystalline trehalose dihydrate of the present invention:

<Experiment 1: Effect of the Origin of CGTase on the Trehalose Content in Enzymatic Reaction Solution>

The following experiments were conducted to examine how does the origin of CGTase used effect on the trehalose content in a saccharide solution, formed by an enzymatic reaction, in an enzymatic reaction system, where an α-glycosyltrehalose-forming enzyme derived from a microorganism of the genus *Arthrobacter* and a trehalose-releasing enzyme derived from also a microorganism of the genus *Arthrobacter* are allowed to act on liquefied starch along with a starch-debranching enzyme and CGTase, and then glucoamylase is allowed to act on the resulting mixture to form trehalose.

<Experiment 1-1: Preparation of Enzyme Solution Containing α-Glycosyltrehalose-Forming Enzyme and Trehalose-Releasing Enzyme Derived from Microorganism of the Genus *Arthrobacter*>

By the method disclosed in Example 2-1 of Patent Literature 4 (Japanese Patent Kokai No. 2000-228980), *Arthrobacter* sp. S34 strain (FERN BP-6450) was cultured to obtain an about 20 L culture. To the 20 L culture was added two grams of "EGG WHITE LYSOZYME", a product name of a lysozyme specimen produced by Nagase ChemteX Corp., Osaka, Japan, to effect cell lysis in the culture by stirring at 260 rpm at 37° C. for 24 hours. The resulting cell-lysed solution was centrifuged to collect a supernatant to obtain a cell extract, which was then in usual manner salted out with ammonium sulfate. The formed precipitation was dialyzed against 10 mM sodium phosphate buffer (pH 7.0), and the dialysate was subjected to an anion-exchange chromatography using "SEPABEADS FP DA13", a gel produced by Mitsubishi Chemical Industries, Co., Tokyo, Japan, to collect an enzyme fraction. The collected fraction was a partially purified enzyme preparation containing about 15,600 units of a trehalose-releasing enzyme and about 3,100 units of an α-glycosyltrehalose-forming enzyme. The activities of the α-glycosyltrehalose-forming enzyme and the trehalose-releasing enzyme were determined in accordance with the methods disclosed in the above Patent Literature 4 (Japanese Patent Kokai No. 2000-228980).

<Experiment 1-2: CGTases Derived from Various Microorganisms>

The following CGTases were used as those derived from various microorganisms. A CGTase derived from *Geobacillus stearothermophilus* Tc-91 strain (FERN BP-11273), produced by Hayashibara Co., Ltd., Okayama, Japan, was used as a CGTase derived from a microorganism of the species *Geobacillus stearothermophilus*; "CONTIZYME", a product name of a commercialized CGTase sold by Amano Enzyme Inc., Aichi, Japan, was used as a CGTase derived from a microorganism of the species *Bacillus macerans*; and "TORUZYME", a product name of a commercialized CGTase sold by Novozymes Japan Ltd., Tokyo, Japan, was used as a CGTase derived from a microorganism of the species *Thermoanaerobacterium thermosulfurigenes*.

The following CGTases were prepared as CGTases derived from microorganisms of the genus *Paenibacillus*: *Paenibacillus illinoisensis* NBRC15959 strain, *Paenibacillus illinoisensis* NBRC15379 strain, *Paenibacillus pabuli* NBRC13638 strain, and *Paenibacillus amylolyticus* NBRC15957 strain were respectively cultured in a liquid culture medium containing 2% dextrin, 0.5% ammonium chloride, 0.05% potassium hydrogen phosphate, 0.025% magnesium sulfate, and 0.5% calcium carbonate at 27° C. for three days. The resulting cultures were centrifuged, and the respective supernatants were in usual manner salted out with ammonium sulfate and dialyzed to obtain crude enzyme solutions of CGTases derived from different microorganisms. The crude enzyme solutions of CGTases thus obtained were respectively subjected to an anion-exchange column chromatography using DEAE-TOYOPEARL 650S GEL commercialized by Tosoh Corp., Tokyo, Japan, and a hydrophobic column chromatography using BUTYL-TOYOPEARL 650M GEL commercialized by Tosoh Corp., Tokyo, Japan, to obtain partially purified CGTases. The activity of each of the CGTases derived from different microorganisms was determined according to the above-identified method and calculated with Formula [1].

<Experiment 1-3: Trehalose-Forming Reaction>

Corn starch was suspended in water to give a concentration of 30% and admixed with 0.1% calcium carbonate. The resulting suspension was adjusted to pH 6.0 and admixed with "TERMAMEAL 60L", a product name of a thermostable α-amylase specimen commercialized by Novozymes Japan Ltd., Tokyo, Japan, in an amount equal to 0.2% of the starch, d.s.b., to gelatinize and liquefy the starch by enzymatically reacting at 95° C. for 15 min. The resulting liquefied starch solution was autoclaved at 120° C. for 30 min, cooled to 51° C., adjusted to pH 5.7, admixed with two units/g starch, d.s.b., of an α-glycosyltrehalose-forming enzyme, 10 units/g starch, d.s.b., of a trehalose-releasing enzyme, 300 units/g starch, d.s.b., of an isoamylase specimen commercialized by Hayashibara Co., Ltd., Okayama, Japan, and 2 units/g starch, d.s.b, of any of the CGTases disclosed in Experiment 1-2 or prepared in Experiment 1-2, and enzymatically reacted for 64 hours. The resulting reaction solution was heated at 97° C. for 30 min to inactivate the remaining respective enzymes, adjusted to pH 4.5, admixed with 10 units/g starch, d.s.b, of "GLUCOZYME #20000", a product name of a glucoamylase specimen commercialized by Nagase ChemteX Corp., Osaka, Japan, and enzymatically reacted for 24 hours. The reaction solution thus obtained was heated at 95° C. for 10 min to inactivate the remaining enzyme, and subjected to the assay for trehalose content in the reaction solution disclosed in the below. Incidentally, a reaction solution, obtained by conducting an enzymatic reaction under the same condition as above except for not adding CGTase, was made as a control.

<Experiment 1-4: Assay for Trehalose Content in Reaction Solution>

The reaction solutions obtained in Experiment 1-3 were respectively made into reaction solutions 1 to 8 shown in Table 1, and the trehalose content in each reaction solution was determined as follows: The reaction solutions 1 to 8 were respectively prepared into 1% solutions with refined water, filtered with a 0.45 μm membrane filter, and subjected to HPLC analysis under the following conditions, followed by calculating the trehalose content in each reaction solution based on the peak areas appeared on chromatograms by a differential refractometer and converting the values based on a dry solid basis. The results are in Table 1. The trehalose contents in the reaction solutions shown in Table 1 are the values that can be obtained in a relatively high reproducibility within a considerable variability even when the respective CGTases are repeatedly subjected to trehalose-forming reaction and glucoamylase treatment five times under the same conditions.

Analytical Conditions:
HPLC system: "LC-10AD", commercialized by Shimadzu Corp., Kyoto, Japan;
Degasser: "DGU-12AM", commercialized by Shimadzu Corp., Kyoto, Japan;
Column: "MCL GEL CK04SS", commercialized by Mitsubishi Chemical Corp., Tokyo, Japan;
Sample injection volume: 20 μl;
Eluent: Refined water;
Flow rate: 0.4 ml/min;
Temperature: 85° C.;
Differential refractometer: "RID-10A", commercialized by Shimadzu Corp., Kyoto, Japan;
Data processing apparatus: "CHROMATOPAC C-R7A", commercialized by Shimadzu Corp., Kyoto, Japan;

TABLE 1

| Reaction solution | Origin of CGTase | Trehalose content in reaction solution after glucoamylase treatment (% by weight, d.s.b.) |
| --- | --- | --- |
| 1 | Control (with no addition of CGTase) | 82.8 |
| 2 | Geobacillus stearothermophilus Tc-91 | 84.7 |
| 3 | Bacillus macerans | 85.1 |
| 4 | Thermoanaerobacterium thermosulfurigenes | 83.4 |
| 5 | Paenibacillus illinoisensis NBRC15959 | 87.6 |
| 6 | Paenibacillus illinoisensis NBRC15379 | 87.4 |
| 7 | Paenibacillus pabuli NBRC13638 | 87.1 |
| 8 | Paenibacillus amylolyticus NBRC15957 | 86.5 |

As evident from Table 1, when the CGTase derived from Geobacillus stearothermophilus Tc-91 strain which had been conventionally used to form trehalose (reaction solution 2), the trehalose content after glucoamylase treatment was up to 84.7%, while the trehalose content was increased to 85.1%, when the CGTase derived from a microorganism of the species Bacillus macerans was used (reaction solution 3), even though the increased amount was negligible. When the CGTase derived from a microorganism of the species Thermoanaerobacter thermosulfurigenes (reaction solution 4), the trehalose content was 83.4% that was lower than the case of using a conventionally used CGTase, derived from Geobacillus stearothermophilus Tc-91 strain (reaction solution 2), in forming trehalose.

On the contrary, when the CGTases derived from microorganisms of the genus Paenibacillus were used (reaction solutions 5 to 8), the trehalose content of any of the solutions after glucoamylase treatment was over 86.0%, d.s.b., which was significantly increased compared to that of using the CGTase derived from Geobacillus stearothermophilus Tc-91 strain that had been conventionally used in forming trehalose (reaction solution 2). Particularly, when the CGTases derived from Paenibacillus illinoisensis NBRC15959 strain (reaction solution 5), Paenibacillus illinoisensis NBRC15379 strain (reaction solution 6), and Paenibacillus pabuli NBRC13638 strain (reaction solution 7) were used as CGTases, the trehalose contents were over 87.0%, revealing that trehalose-containing saccharide solutions with a high trehalose content are obtained by such enzymatic reactions. Among the results of this experiment, when a CGTase derived from a microorganism of the species Paenibacillus illinoisensis was used, the highest trehalose content was obtained, revealing that the CGTases derived from microorganisms of the species Paenibacillus illinoisensis are most preferable.

<Experiment 2: Trehalose Purity, Production Yield Against Starch, and Properties of Particulate Compositions Containing Crystalline Trehalose Dihydrate, Prepared from Saccharide Solutions with Different Trehalose Contents>

<Experiment 2-1: Preparation of Test Samples>

<Test Samples 1 to 8>

The reaction solutions 1 to 8 with different trehalose contents, obtained in Experiment 1, were respectively purified by decoloration treatment using an activated charcoal and desalting treatment using an ion-exchange resin, and concentrated up to give a solid concentration of about 60%, d.s.b., to obtain trehalose-containing saccharide solutions 1 to 8 (containing 82.8 to 87.6% trehalose, d.s.b.) which corresponded to the reaction solutions 1 to 8, respectively.

The above trehalose-containing saccharide solutions 1 to 8 were respectively concentrated in vacuo to give a solid concentration of about 85%, d.s.b., placed in a crystallizer, admixed with about 1% w/v crystalline trehalose dihydrate as a seed crystal to the volume of each saccharide solution, and crystallized under stirring conditions by unforcedly cooling the mixture from 60° C. to 20° C. over about 10 hours to obtain massecuites with precipitated crystalline trehalose dihydrate. From each of the above massecuites, a crystalline trehalose dihydrate was collected in usual manner by a basket-type centrifuge, washed with 8% deionized water to the weight of each massecuite, aged and dried at 40° C. for eight hours, forcedly cooled by blowing to the resultants 25° C. clean air for 30 min, and pulverized to obtain particulate compositions containing crystalline trehalose dihydrate. The particulate compositions containing crystalline trehalose dihydrate, which had been respectively prepared from the trehalose-containing saccharide solutions 1 to 8, were respectively made into test samples 1 to 8.

<Test Sample 9>

"TREHA" (Lot No.: 91131), a product name of a food-grade powder containing crystalline trehalose dihydrate, commercialized by Hayashibara Co., Ltd., Okayama, Japan, was used as test sample 9.

<Experiment 2-2: Trehalose Purity, Production Yield Against Starch, and Cakeability of Test Samples 1 to 9>

<Trehalose Purity>

The trehalose purity of test samples 1 to 9 were determined by the same HPLC method as in Experiment 1-3. The results are in Table 2.

<Production Yield Against Starch>

The production yields against starch of test samples 1 to 8 prepared in the above were obtained by calculating the weight, d.s.b., of a material starch based on the weight of each of the enzymatic reaction solutions used in preparing the test samples and the concentration (30%) of a material starch at the initial production, dividing the weight, d.s.b., of each of the test samples 1 to 8 by the weight calculated in the above, and multiplying the resulting values by 100. The results are in Table 2.

<Caking Test>

For each test samples 1 to 9, the following experiments were conducted for the purpose of examining the cakeability of each powder. Test samples 1 to 9 were respectively weighed by one gram, separately placed in "FALCON TUBE 2059", a product name of a 14-ml polypropylene cylindrical tube, 1.7 cm in diameter and 10 cm in height, having a hemispherical bottom shape and a cap, commercialized by Becton, Dickinson and Company, New Jersey, USA. The tubes were set to a tube rack uprightly and housed in "IC-410", a product name of an incubator commercialized by Advantec Toyo Kaisha, Ltd., Tokyo, Japan, controlled at 50° C. After allowing to stand for 24 hours, the tubes were taken out from the incubator, followed by removing the cap from each tube, taking out each test sample from the tubes to place them on a black-plastic-plane plate by turning the tubes upside down slowly, and macroscopically observing the conditions of the taken-out test samples.

The degree of caking of each test sample was judged based on the following criteria: "Caked", (+): Test sample clearly kept the hemispherical shape of the bottom of the tube even when placed on the plane plate; "Slightly caked", (±): Test sample slightly, recognizably showed the hemispherical shape of the bottom of the tube; and "Not caked", (−): Test sample deformed and kept no hemispherical shape of the bottom of the tube. The results are shown in the column of "Caking" in Table 2.

TABLE 2

| Test sample | Trehalose purity (% by weight) | Production yield against starch (% by weight) | Caking |
|---|---|---|---|
| 1 | 98.4 | 31 | + |
| 2 | 98.8 | 38 | ± |
| 3 | 99.2 | 39 | ± |
| 4 | 98.7 | 37 | + |
| 5 | 99.3 | 42 | ± |
| 6 | 99.2 | 42 | ± |
| 7 | 99.2 | 42 | ± |
| 8 | 99.1 | 41 | ± |
| 9 | 99.0 | — | ± |

As shown in Table 2, the trehalose contents, d.s.b., of the particulate compositions containing crystalline trehalose dihydrate of test samples 1 to 8, i.e., the trehalose purities were all over 98.0%, and they were high-purity particulate compositions containing crystalline trehalose dihydrate similarly as test sample 9 as a conventional food-grade powder containing crystalline trehalose dihydrate. Nevertheless, as for the production yield against starch, those in test samples 2 to 4, where CGTases other than those derived from microorganisms of the genus Paenibacillus, remained in a production yield against starch of as high as 39%, while test samples 5 to 8, prepared with CGTases derived from microorganisms of the genus Paenibacillus, showed a production yield against starch of 41 to 42% as higher than 40%, revealing that there was found a difference among the origins of CGTases used. Comparing the results in Table 1 with those in Table 2, the particulate compositions containing crystalline trehalose dihydrate prepared from enzymatic reaction solutions with higher trehalose contents after glucoamylase treatment were tended to have a higher production yield against starch, and there was found a relationship between the trehalose contents in enzymatic reaction solutions and the production yields against starch.

Based on these results, when CGTases derived from microorganisms of the genus Paenibacillus (test samples 5 to 8) are used as CGTases, the trehalose contents in enzymatic reaction solutions after glucoamylase treatment are over 86.0%, and as a result it was revealed that the production yields against starch for particulate compositions containing crystalline trehalose dihydrate also increase to 41% or higher. In particular, when CGTases derived from microorganisms of the species Paenibacillus illinoisensis or Paenibacillus pabuli (test samples 5 to 7), the trehalose contents in enzymatic reaction solutions after glucoamylase treatment are over 87.0% and the production yields against starch further increase to 42%. When CGTases derived from microorganisms of the genus Paenibacillus are used, the levels of improvement in the production yields against starch (the production yields against starch for test samples 5 to 8) are 3 to 4% compared to that with a conventionally used CGTase derived from Geobacillus stearothermophilus Tc-91 strain (test sample 2), however, it must be distinctly extraordinary the fact that the production yields against starch are improved even by 3 to 4% on an industrial scale production of particulate compositions containing crystalline trehalose dihydrate.

As for cakeability as an important property in handling as a powder, test sample 1 prepared from a trehalose-containing saccharide solution without using any CGTase and test sample 4 prepared with a CGTase derived from a microorganism of the species Thermoanaerobacter thermosulfurigenes were judged as "Caked" (+) in the above caking test, while test samples 2, 3 and 5 to 8 prepared with other CGTases were judged as only "Slightly caked" (±) in the above caking test similarly as a conventional food-grade powder containing crystalline trehalose dihydrate (test sample 9). The results indicate that the particulate compositions containing crystalline trehalose dihydrate prepared by using CGTases derived from microorganisms of the genus Paenibacillus (test samples 5 to 8) are in no way inferior to a commercialized conventional food-grade powder containing crystalline trehalose dihydrate (test sample 9) and they are particulate compositions that can be used as powdered materials for food products, cosmetics, quasi-drugs, or pharmaceuticals similarly as a conventionally commercialized food-grade powder containing crystalline trehalose dihydrate.

<Experiment 3: Effect of Semi-Controlled Cooling when in Crystallization on Trehalose Purity, Production Yield Against Starch, and Cakeability>

In this experiment, it was examined the Effect of the application of a semi-controlled cooling method to the preparation of a particulate composition containing crystalline trehalose dihydrate on the trehalose purity, production yield against starch, and cakeability of the particulate composition, when crystalline trehalose dihydrate is precipitated from the trehalose-containing saccharide solutions 1 to 8 prepared in Experiment 2-1.

<Experiment 3-1: Preparation of Test Samples>

The trehalose-containing saccharide solutions 1 to 8 with different trehalose contents, d.s.b, prepared in Experiment 2-1, were respectively concentrated in vacuo up to give a solid concentration of about 85%, d.s.b., placed in a crystallizer, admixed with about one percent of crystalline trehalose dihydrate as a seed crystal to the volume of each saccharide solution, followed by preparing massecuites having precipitated crystalline trehalose dihydrate similarly as in Experiment 2 except for crystallizing by a semi-controlled cooling method of cooling the solutions from 60° C. to 20° C. over about 10 hours. The semi-controlled cooling method was carried out in such a manner of dividing the total 10 hours of cooling time into three zones with four, three, and three hours, roughly linearly cooling the liquid temperature against time in such a manner of decreasing from 60° C. to 55° C. over four hours in the first zone, from 55° C. to 50° C. over three hours in the next zone, and from 50° C. to 20° C. over three hours in the last zone. Crystalline trehalose dihydrate was collected from each of the obtained massecuites in usual manner by a basket-type centrifuge, washed with eight percent of deionized water to the weight of each massecuite, aged and dried at 40° C. for eight hours, forcedly cooled by blowing 25° C. clean air for 30 min, and pulverized into particulate compositions containing crystalline trehalose dihydrate. The particulate compositions containing crystalline trehalose dihydrate, obtained from respective trehalose-containing saccharide solutions 1 to 8 by the semi-controlled cooling method, were made into test samples 1c to 8c.

<Experiment 3-2: Trehalose Purity, Production Yield Against Starch, and Cakeability of Test Samples 1c to 8c>
<Trehalose Purity>

The trehalose purities of test samples 1c to 8c were determined by the same HPLC method as in Experiment 1-3. The results are in Table 3.

<Production Yield Against Starch>

The production yields against starch of test samples 1c to 8c were calculated by the same method as in Experiment 2-2. The results are in Table 3 in parallel.

<Caking Test>

The cakeability of test samples 1c to 8c were evaluated by the same caking test as in Experiment 2-2. The results are in Table 3 in parallel.

TABLE 3

| Test sample | Trehalose purity (% by weight) | Production yield against starch (% by weight) | Caking |
|---|---|---|---|
| 1c | 99.0 | 35 | ± |
| 2c | 99.2 | 40 | ± |
| 3c | 99.4 | 41 | ± |
| 4c | 99.1 | 39 | ± |
| 5c | 99.6 | 45 | − |
| 6c | 99.6 | 45 | − |
| 7c | 99.5 | 44 | − |
| 8c | 99.4 | 43 | − |

As evident from Table 3, the trehalose purities of test samples 1c to 8c, prepared by applying a semi-controlled cooling method in their crystallization steps, were in the range of 99.0 to 99.6%. Comparing the result with the trehalose purities of test samples 1 to 8 obtained through crystallization by an unforced cooling method in Experiment 2 (the column of "trehalose purity" in Table 2), the trehalose purity of any of test samples 1c to 8c were increased by 0.2 to 0.6%. The result indicates that the trehalose purity of a particulate composition can be increased by applying a semi-controlled cooling method in its crystallization step.

The production yields against starch of test samples 1c to 8c were 35 to 45%. Comparing the result with the production yields against starch of test samples 1 to 8 obtained through precipitation by an unforced cooling method in Experiment 2, the production yields against starch of test samples 1c to 8c were increased by about 2 to 4%. The result means that the application of a semi-controlled cooling method to crystallization will increase the production yield against starch, compared to the case of crystallization by an unforced cooling method. The reason why the production yield against starch of a resulting particulate composition containing crystalline trehalose dihydrate is increased by applying a semi-controlled cooling method, even though there is found no change in trehalose content in a trehalose-containing saccharide solution used in crystallization, is not sure; however, it can be speculated that a loss of trehalose is reduced when in collecting crystals from a massecuite by centrifugation and washing the collected crystals with water because crystals that have a lesser amount of microcrystals and a uniform particle size are obtained by a semi-controlled cooling method as mentioned above.

When test samples 1c to 8c were subjected to caking test similarly as in Experiment 2-2 to examine their cakability, test samples 1c to 4c as shown in Table 3 were all judged as "Slightly caked" (±), while any of test samples 5c to 8c deformed when taken out on a plane plate and did not keep their shapes with the bottom of the tube, and thus they were judged as "Not caked" (−). These results indicate that, when a semi-controlled cooling method is applied in crystallization, the cakeability of a resulting particulate composition is tended to be surprisingly improved compared to the case of crystallization by an unforced cooling method. Among which, the conventional food-grade powder containing crystalline trehalose dihydrate (test sample 9) was judged as "Slightly caked" (±) (see, for example, Table 2) in caking test, while the particulate compositions containing crystalline trehalose dihydrate obtained from trehalose-containing saccharide solutions 5 to 8 with a relatively-high trehalose content of as over as 86% (test samples 5c to 8c) by applying a semi-controlled cooling method were judged as "Not caked" (−). The fact indicates that a particulate composition containing crystalline trehalose dihydrate, which is significantly hardly cakeable compared to a conventional food-grade powder containing crystalline trehalose dihydrate and is superior in property as a particulate composition, can be produced by being precipitated from a trehalose-containing saccharide solution with a relatively-high trehalose content of as over as 86% by applying a semi-controlled cooling method.

Based on the above results, it was revealed that a particulate composition containing crystalline trehalose dihydrate with a higher trehalose purity can be obtained in a higher production yield against starch by applying a semi-controlled cooling method in crystallization step, compared to the case of being precipitated by an unforced cooling method. It was revealed that a particulate composition containing crystalline trehalose dihydrate, produced from a saccharide solution with a relatively high trehalose content of as over as 86% through crystallization by a semi-controlled cooling method, is an advantageous particulate composition in that it is not caked even under the conditions where a conventional food-grade powder containing crystalline trehalose dihydrate produced by an unforced cooling method is judged as "Slightly caked" (±), and it retains a free-flowing ability as a particulate composition.

<Experiment 4: Effect of the Degree of Crystallinity and the Average Crystallite Diameter on the Difference of Cakeability of Particulate Composition>

Test samples 5c to 8c as particulate compositions containing crystalline trehalose dihydrate, which had been prepared from a saccharide solution with a relatively high trehalose content of over 86% by applying a semi-controlled cooling method in Experiment 3, had a superior powder property of hardly caking even though they were not so different from other test samples in terms of trehalose purity. For the purpose of revealing the reason, the degrees of crystallinity and the average crystallite diameters of the particulate compositions containing crystalline trehalose dihydrate of test samples 1 to 8 obtained in Experiment 2 and test samples 1c to 8c obtained in Experiment 3 were measured in this experiment. As a control, test sample 9 was also examined similarly.

<Experiment 4-1: Preparation of Standard Samples Used for Measuring the Degree of Crystallinity>

<Standard Sample A>

As test sample A, a standard specimen consisting substantially of crystalline trehalose dihydrate was prepared by recrystallizing "TREHALOSE 999" (Code No.: TH224, purity of 99.9% or higher), a product name of a reagent-grade powder containing crystalline trehalose dihydrate: In 1,000 g of refined water was dissolved by heating 1,840 g of the above reagent-grade powder containing crystalline trehalose dihydrate, and the solution was placed in a constant-temperature chamber controlled at 20° C. and allowed to stand overnight to effect recrystallization. The crystalline trehalose dihydrate precipitated by the recrystallization was collected in usual manner by using a basket-type centrifuge, dried at 40° C. for eight hours to obtain an about 950 g crystalline trehalose dihydrate for use as test sample A. The trehalose purity of test sample A was revealed to be 100% when determined on the HPLC method disclosed in Experiment 1.

<Standard Sample B>

A standard specimen consisting substantially of amorphous trehalose as test sample B was prepared by the following procedure: Test sample A was dissolved in an adequate amount of refined water, freeze-dried over three days, and dried in vacuo at 40° C. or lower overnight to obtain a powder consisting substantially of amorphous trehalose for use as test sample B. The trehalose purity of test sample B was revealed to be 100% when determined on the HPLC method disclosed in Experiment 1. The moisture content of test sample B was 2.0% when determined on the Karl Fischer method.

<Experiment 4-2: Degree of Crystallinity of Test Samples A and B, Test Samples 1 to 9, and Test Samples 1c to 8c>

<Degree of Crystallinity>

The degrees of crystallinity for crystalline trehalose dihydrate of test samples A and B, test samples 1 to 9, and test samples 1c to 8c were determined as follows: Analytical values for the degrees of crystallinity of test samples A and B, test samples 1 to 9, and test samples 1c to 8c were respectively determined by the Hermans' method based on the powder X-ray diffraction profiles obtained by using "X' Pert PRO MPD", a product name of a commercially available reflected-light powder X-ray diffractometer commercialized by Spectris Co., Ltd., Tokyo, Japan, which irradiates a CuKα-ray (X-ray electric current: 40 mA, X-ray tube voltage: 45 kV, wavelength: 1.5405 Å), as a characteristic X-ray irradiated from a Cu target; and using a computer analysis software exclusively installed in the diffractometer. Prior to the analysis of the degree of crystallinity by the Hermans' method, the particle degree and the bending factor pre-set in the software were respectively adjusted to appropriate levels for obtaining a base-line judged to be most preferable, while considering mutually overlapping peaks, diffraction intensity, and scattering intensity in respective powder X-ray diffraction patterns. The Hermans' method is described in detail in P. H. Hermans and A. Weidinger, "*Journal of Applied Physics*, Vol. 19, pp. 491-506 (1948) and P. H. Hermans and A. Weidinger, "*Journal of Polymer Science*", Vol. 4, pp. 135-144 (1949).

The degrees of crystallinity were determined by substituting into the aforesaid Formula [3] the analytical values for the degrees of crystallinity of test sample A, test sample B, and each test sample as respective analytical values $H_{100}$, $H_0$, and Hs. Incidentally, when analyzed by the Hermans' method, the analytical value of the degree of crystallinity for test sample A ($H_{100}$) and that for test sample B ($H_0$) were respectively 50.69% and 8.59%. The results are in Table 4. For test samples A and B, their powder X-ray diffraction patterns are respectively shown in FIGS. 1 and 2.

Figure 2:
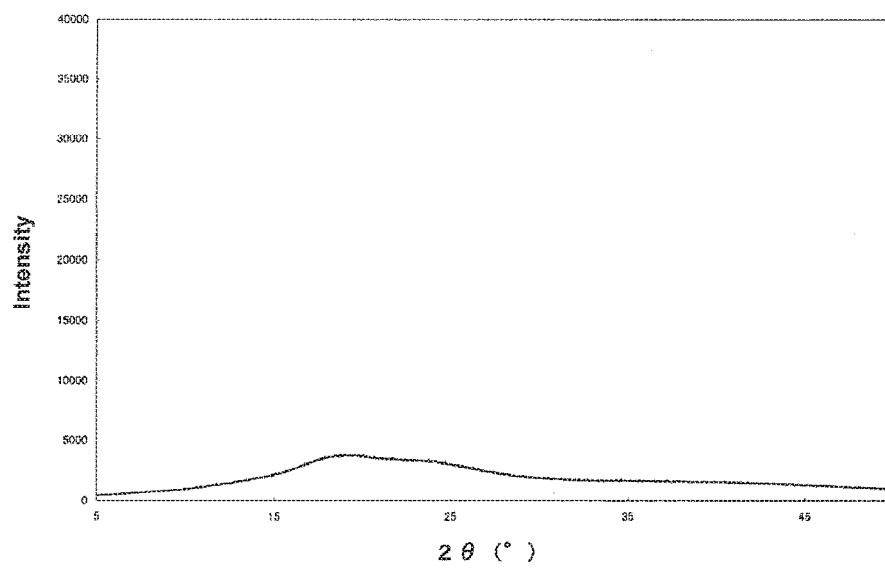
FIG. 2 is an example of a powder X-ray diffraction pattern with a characteristic X-ray for a particulate composition containing trehalose, which substantially consists of an amorphous form of trehalose.

As found in FIG. 1, clear and sharp diffraction peaks specific to crystalline trehalose dihydrate were found in the range of diffraction angles (2θ) of 5 to 50° in the powder X-ray diffraction pattern of test sample A, but no halo specific to an amorphous form of trehalose was found. While, as found in FIG. 2, unlike the powder X-ray diffraction pattern of FIG. 1, a halo specific to an amorphous form of trehalose was clearly found as a bunch of baseline in the powder X-ray diffraction pattern of test sample B, but no diffraction peak specific to crystalline trehalose dihydrate or anhydrous crystalline trehalose was found.

<Experiment 4-3: Powder X-Ray Diffractions of Test Samples A and B Using Synchrotron Radiation>

This experiment was carried out to further confirm that test samples A and B were proper samples for determining the analytical values $H_{100}$ and $H_0$, respectively: These samples were subjected to a transmitted-light powder X-ray diffraction, which detects a weak diffraction and scattering signal, using a synchrotron radiation (called "radiation", hereinafter), as an X-ray source. The analytical conditions were as follows.

<Analytical Conditions>

Powder X-ray diffractometer: Model "PDS-16", a high-speed powder X-ray diffractometer (debye Scherrer mode, camera length: 497.2 mm) commercialized by Kohzu Precision Co., Ltd., Kanagawa, Japan;

X-Ray source: "Beam line of Hyogo Prefecture (BL08B2)", a radiation light from bending electromagnet;
Wavelength: 1.2394 Å (10.00 keV);
Strength: $10^9$ photons/sec;
Measuring angle: 3 to 38°;
Exposure time: 600 sec;
Image recording: "IMAGING PLATE BAS-2040", an imaging plate commercialized by Fujifilm Corp., Tokyo, Japan; and
Image reading system: "BIO-IMAGE ANALYZER BAS-2500", an image analyzer commercialized by Fujifilm Corp., Tokyo, Japan.

The measurement was conducted by using "Beam line of Hyogo Prefecture (BL08B2)" placed in "SPring-8", a synchrotron radiation facility, 1-1-1, Kouto, Sayo-cho, Sayo-gun, Hyogo, Japan.

Prior to powder X-ray diffraction measurement, test samples A and B were respectively ground in a mortar and sieved with a 53 μm mesh-sieve. Then, each of the resulting particulate compositions passed through the sieve was homogeneously injected into "MARKTUBE No. 14", a product name of a capillary for powder X-ray diffraction (diameter: 0.6 mm, Lindeman glass), commercialized by Toho K K, Tokyo, Japan, to give an injected sample length of about 30 mm. Successively, the capillary was cut at the end terminal of the injected sample and the open end was sealed with an adhesive. Then, the capillary was fixed on a sample mount with a clay, and the sample mount was set to the powder X-ray diffractometer to give the longitudinal direction of the capillary perpendicularly against the optic axis of the powder X-ray diffractometer. To remove adverse effect of the orientation of crystalline trehalose dihydrate on its powder X-ray diffraction profile, the measurement of the powder X-ray diffraction was carried out by allowing the sample mount to rotate at a uniform velocity and at a cycle of twice/sec.

In the processes of analyzing the powder X-ray diffraction profiles and preparing the powder X-ray diffraction patterns of test samples A and B, background signals inherent to the powder X-ray diffractometer were eliminated from each powder X-ray diffraction profile according to conventional manner for improving the measurement accuracy. The resulting powder X-ray diffraction patterns of test samples A and B are respectively shown in FIGS. 3 and 4.

Figure 3:
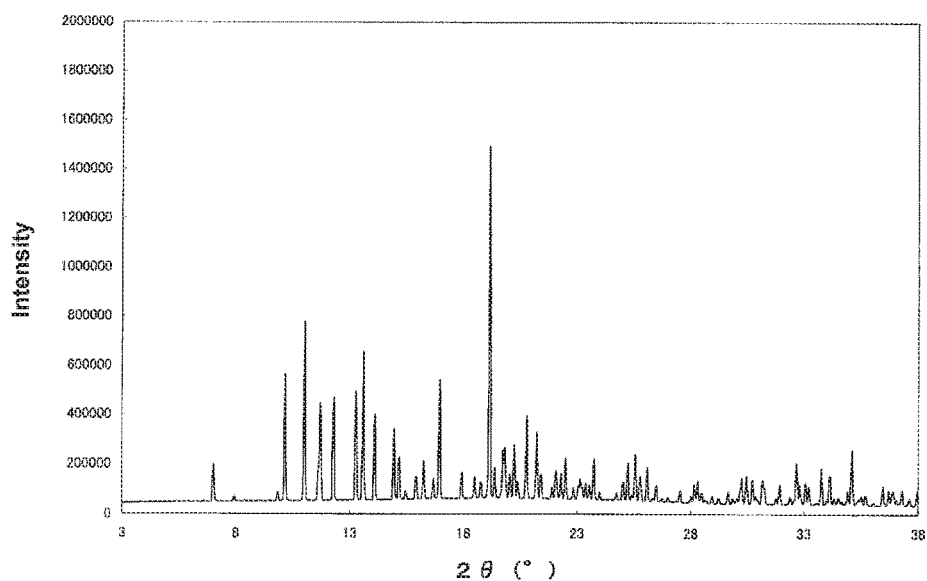
FIG. 3 is an example of a powder X-ray diffraction pattern with a synchrotron radiation for a particulate composition containing crystalline trehalose dihydrate, which substantially consists of crystalline trehalose dihydrate.

As found in FIG. 3, the diffraction peaks specific to crystalline trehalose dihydrate appeared clearly and sharply in the range of diffraction angles (2θ) of 3 to 38° for the powder X-ray diffraction pattern of test sample A, measured on the powder X-ray diffraction using the synchrotron radiation. Since the wavelength of the synchrotron radiation (1.2394 Å) was different from that of the characteristic X-ray (1.5405 Å) compared to FIGS. 3 and 1, each diffraction peak in FIG. 3 appeared by about four fifth of the diffraction angle (2θ) of each of the corresponding peaks in FIG. 1. However, the powder X-ray diffraction patterns in FIGS. 1 and 3 were extremely well coincided with each other. The half width of each diffraction peak in FIG. 3 was evidently narrower than that in FIG. 1 and each diffraction peak in FIG. 3 showed a higher resolution than that in FIG. 1, although the strength of each diffraction peak in FIG. 3 was higher than that in FIG. 1 by nearly 50-folds. The powder X-ray diffraction pattern in FIG. 3 showed no halo specific to an amorphous form of trehalose, as shown in the later described FIG. 4. The result indicates that test sample A has a distinctly high crystallinity for crystalline trehalose dihydrate and it consists substantially of crystalline trehalose dihydrate.

Figure 4:
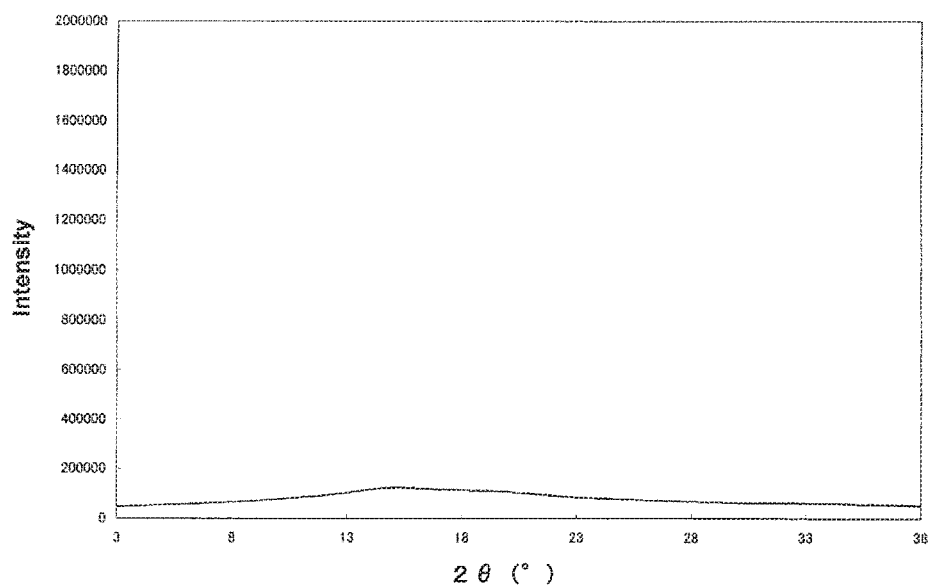
FIG. 4 is an example of a powder X-ray diffraction pattern with a synchrotron radiation for a particulate composition containing trehalose, which substantially consists of an amorphous form of trehalose.

As shown in FIG. 4, the powder X-ray diffraction pattern of test sample B, obtained by the powder X-ray diffraction using the synchrotron radiation, showed a remarkable halo specific to an amorphous form of trehalose as a bunch of baseline but no diffraction peak specific to crystalline trehalose dihydrate was observed. The fact indicates that test sample B consists substantially of an amorphous form of trehalose.

The above results, obtained by using the synchrotron radiation as an X-ray source, support that test samples A and B are proper samples for defining the analytical values $H_{100}$ and $H_0$, respectively, for use in Formula [3].

<Experiment 4-4: Average Crystallite Diameters of Test Sample a, Test Samples 1 to 9, and Test Samples 1c to 8c>

Based on the half widths and the diffraction angles (2θ) of each diffraction peak in a powder X-ray diffraction pattern, crystallite diameters can be calculated. The present inventors considered that an average value of crystallite diameters (average crystallite diameter) calculated from diffraction peaks would be a parameter that defines the physical property of a particulate composition containing crystals, and they determined average crystallite diameters for test samples as particulate compositions containing crystalline trehalose dihydrate.

Test sample A, test samples 1 to 9, and test samples 1c to 8c, excluding test sample B which is an amorphous powder and which exhibits no diffraction peak in its powder X-ray diffraction pattern, were further determined their respective average crystallite diameters by using each of their powder X-ray diffraction patterns that had been used in determining their degrees of crystallinity. Each average crystallite diameter was determined by selecting five diffraction peaks in the powder X-ray diffraction patterns for each particulate composition containing crystalline trehalose dihydrate, i.e., diffraction peaks (the symbols "a" to "e" in FIG. 1) at diffraction angles (2θ) of 13.7° (Miller's index (hkl): 101), 17.5° (Miller's index (hkl): 220), 21.1° (Miller's index (hkl): 221), 23.9° (Miller's index (hkl): 231), and 25.9° (Miller's index (hkl): 150), which located in a relatively low-angle region that was considered to be least disruptive to diffraction peak width due to heterogeneous strain of crystallite, and which were well separated from other diffraction peaks; calibrating the half widths and diffraction angles (2θ) of the diffraction peaks based on a measured value determined by using "X' pert Highscore Plus" as an analytical processing computer software exclusively installed in the powder X-ray diffractometer, and a silicon ("Si640d", provided by NIST: National Institute of Standards and Technology, as a standard sample for X-ray diffraction) as a standard sample; calculating crystallite diameters based on the above Formula [4]; and averaging the above five data. The results are in Table 4 in parallel.

The results on the trehalose purity and the caking test on particulate compositions for test samples 1 to 9 and test samples 1c to 8c are respectively transcribed from Tables 2 and 3 and shown in parallel in Table 4. Test samples A and B, used as standard specimens for determining degree of crystallinity, were respectively subjected to the same caking test as in Experiments 2-2 and 3-2 and evaluated their cakeability. The results are in Table 4 in parallel.

TABLE 4

| Test sample | Trehalose purity (% by weight) | Degree of crystallinity (%) | Average crystallite diameter (Å) | Caking |
|---|---|---|---|---|
| A | 100 | 100 | 3,910 | − |
| B | 100 | 0 | — | + |
| 1 | 98.4 | 78.7 | 2,150 | + |
| 2 | 98.8 | 85.1 | 2,540 | ± |
| 3 | 99.2 | 85.3 | 2,660 | ± |
| 4 | 98.7 | 80.8 | 2,200 | + |
| 5 | 99.3 | 88.1 | 2,830 | ± |
| 6 | 99.2 | 87.7 | 2,750 | ± |
| 7 | 99.2 | 87.4 | 2,670 | ± |
| 8 | 99.1 | 86.6 | 2,610 | ± |
| 9 | 99.0 | 85.4 | 2,590 | ± |
| 1c | 99.0 | 85.7 | 2,540 | ± |
| 2c | 99.2 | 87.3 | 2,780 | ± |
| 3c | 99.4 | 88.6 | 2,850 | ± |
| 4c | 99.1 | 88.3 | 2,630 | ± |
| 5c | 99.6 | 96.0 | 3,580 | − |
| 6c | 99.6 | 94.2 | 3,490 | − |
| 7c | 99.5 | 93.3 | 3,300 | − |
| 8c | 99.4 | 91.0 | 3,210 | − |

The average crystallite diameter of test sample A (trehalose purity: 100.0%, degree of crystallinity: 100.0%), used as a standard sample for determining analytical value $H_{100}$ in measuring the degree of crystallinity, was 3,910 Å. As shown in Table 4, test sample A was judged as "Not caked" (−) in the caking test. In contrast, test sample B used as a standard sample for determining the analytical value $H_0$ (trehalose purity: 100.0%, degree of crystallinity: 0.0%) was judged as "Caked" (+) because it still kept its hemispherical shape of the bottom of a tube even when taken out from the tube and placed on a plane plate. The hemispherical shape of test sample B was not collapsed when a slight vibration was merely given to the plate. While, the trehalose purity and the degree of crystallinity of test sample 9 as a conventionally commercialized food-grade crystalline trehalose dihydrate were respectively 99.0% and 85.4%.

As shown in the column of "Degree of crystallinity" in Table 4, the degrees of crystallinity of test samples 1 to 8, which had been obtained by precipitation by an unforced cooling method in the crystallization step, were in the range of 78.7 to 88.1%, while those of test samples 1c to 8c, which had been obtained by applying a semi-controlled cooling method in the crystallization step, were in the range of 85.7 to 96.0%. Comparing the degrees of crystallinity of test samples 1 to 8 with those of test samples 1c to 8c in terms of the difference of crystallization methods, it was revealed that the degrees of crystallinity of test samples 1c to 8c obtained by a semi-controlled cooling method were increased by 3.1 to 7.9% compared to those of test samples 1 to 8 obtained by an unforced cooling method, though the degrees of crystallinity of test samples 1c to 8c varied one another.

The results in Table 4 indicate that the degree of crystallinity of a particulate composition correlates with its cakeability. More specifically, as shown in Table 4, every test sample A and test samples 5c to 8c with a degree of crystallinity of 90% or higher were judged as "Not caked" (−), while every test samples 2, 3, and 5 to 9 and test samples 1c to 4c with a degree of crystallinity of 85% or higher but less than 90% were judged as "Slightly caked" (±), and every test sample B and test samples 1 and 4 with a degree of crystallinity of less than 85% were judged as "Caked" (+). The fact indicates that the degree of crystallinity can be a potent index for defining a hardly cakeable particulate composition containing crystalline trehalose dihydrate.

Further the above result indicates that, in the process for producing a particulate composition containing crystalline trehalose dihydrate, the degree of crystallinity for crystalline trehalose dihydrate becomes 90% or higher by increasing the trehalose content in a reaction solution up to over 86.0% and then applying a semi-controlled cooling method in the following crystallization step, resulting in obtaining a significantly, hardly cakeable particulate composition containing crystalline trehalose dihydrate compared to a conventional food-grade powder containing crystalline trehalose dihydrate.

As shown in the column of "Average crystallite diameter" in Table 4, the average crystallite diameters of test samples 1 to 8 obtained by crystallization by an unforced cooling method in the crystallization step were in the range of 2,150 to 2,830 Å, while those of test samples 1c to 8c prepared by a semi-controlled cooling method in the crystallization step were in the range of 2,540 to 3,580 Å. Comparing test samples 1c to 8c with test samples 1 to 8 in terms of their average crystallite diameters, it was revealed that the average crystallite diameters of test samples 1c to 8c obtained by a semi-controlled cooling method were increased by 190 to 750 Å compared to those of test samples 1 to 8 obtained by an unforced cooling method, though the average crystallite diameters of test samples 1c to 8c varied one another. The result shows that the application of a semi-controlled cooling method in the crystallization step for crystalline trehalose dihydrate is a superior method for obtaining a particulate composition containing crystalline trehalose dihydrate with a relatively large average-crystallite-diameter.

In test samples 1 to 8 and test sample 1c to 8c, there was found a tendency that the higher the trehalose purity and the degree of crystallinity for crystalline trehalose dihydrate in particulate compositions, the larger the average crystallite diameter. This tendency indicates that the average crystallite diameter of a particulate composition containing crystalline trehalose dihydrate has a certain correlation with both the trehalose purity and the degree of crystallinity of a particulate composition containing crystalline trehalose dihydrate, considering both the fact that the average crystallite diameter of test sample 1, which had a trehalose purity of 100.0% and a degree of crystallinity of 100.0%, was 3,910 Å and that test sample 9 as a food-grade powder containing crystalline trehalose dihydrate was 2,590 Å.

Further, the results in Table 4 indicate that the average crystallite diameter also correlates with the cakeability of a particulate composition. In detail, as shown in Table 4, test sample A and test samples 5c to 8c, which had an average crystallite diameter of 3,210 Å or larger, were all judged as "Not caked" (−); test samples 2, 3, and 5 to 9 and test samples 1c to 4c, which had an average crystallite diameter in the range of 2,500 Å or larger but less than 3,200 Å, were all judged as "Slightly caked" (±); and test sample B and test samples 1 to 4, which had an average crystallite diameter of less than 2,500 Å, were all judged as "Caked" (+). The fact indicates that, in addition to the degree of crystallinity, the average crystallite diameter can also be a potent index for defining a hardly cakeable crystalline trehalose dihydrate.

<Experiment 5: Powder Characteristics of Test Samples (Storage Stability, Solubility in Water)>

Tests for storage stability and solubility in water were conducted for the purpose of further revealing the property of test samples 1 to 9 and test samples 1c to 8c.

<Experiment 5-1: Storage Stability Test>

To confirm whether the caking test conducted in Experiments 2-2, 3-2, etc., are acceptable as a test for evaluating the cakeability of a particulate composition containing crystalline trehalose dihydrate when in actual storage, test samples A and B obtained by the method in Experiment 4-1, test samples 1 to 9 obtained in Experiment 2, and test samples 1c to 8c obtained in Experiment 3 were subjected to a storage stability test designed by considering conditions, circumstances, and period for actually storing particulate compositions containing crystalline trehalose dihydrate as commercially distributed products.

One hundred and fifty grams of any one of test samples A and B, test samples 1 to 9, and test samples 1c to 8c was weighed, placed in "UNI-PACK F-4", a product name of a polyethylene bag, 17 cm×12 cm, commercialized by Seisannipponsha Ltd., Tokyo, Japan, and sealed therein in a deaerated condition to obtain three polyethylene bags for each test sample. A 13.2-kg-weight was placed on each polyethylene bag to homogeneously put a load over the upper surface of each bag so as to give a load of 648 kg/m² for one surface of each bag and stored at the conditions for 60 days under circumstances free of a relatively high temperature and humidity. By comparison, a product of a food-grade powder containing crystalline trehalose dihydrate usually has a 20-kg packing style, and about 10 bags of which are piled up when stored in a storehouse, etc. The load of 648 kg/m² for one surface of a polyethylene bag corresponds to the load received by the lowest bag among the piled-up 10 bags. After 60 days storage, each test sample was taken out from each polyethylene bag, sieved with a sieve having a pore size of 425 µm, and the weights of powders passed through or not passed through the sieve were respectively weighed, followed by determining the weight percentage (%) of particles with a particle size of 425 µm or larger to the whole powder and averaging the data from three bags for each of the test samples tested to evaluate the caking of each particulate composition after 60 days storage. The caking of particulate compositions were evaluated as follows: "Not caked" (−), where particles with a particle size of 425 µm or larger are less than 30% of the whole particulate composition; and "Caked" (+), where particles with a particle size of 425 µm or larger are 30% or more of the whole particulate composition. The criterion of judgement was made as 30% because the dissolution of a particulate composition and the mixing or kneading thereof with other particulate composition(s) will generally be affected when the ratio of particles with a particle size of 425 µm or larger in the particulate composition exceeds 30%. The results are in Table 5.

<Experiment 5-2: Test for Solubility in Water>

Each test sample was weighed by 0.25 g and placed in "FALCON TUBE 2059", a product name of a 14-ml polypropylene cylindrical tube having a hemispherical bottom shape and a cap, commercialized by Becton, Dickinson and Company, New Jersey, USA. To each tube with each test sample was added five milliliters of deionized water, and the tubes were incubated for 30 min in a 50° C. constant temperature water bath, upset two times, and then kept at 50° C. for 15 min to examine the solubility under the conditions. It was judged as "Passable" when a particulate composition is macroscopically judged to be completely dissolved, while it was judged as "Impassable" when an insoluble residue is macroscopically observed. The results are in Table 5 in parallel.

TABLE 5

| Test sample | Storage stability | Solubility in water |
|---|---|---|
| A | − | Impassable |
| B | + | Passable |
| 1 | + | Passable |
| 2 | + | Passable |
| 3 | + | Passable |
| 4 | + | Passable |
| 5 | + | Passable |
| 6 | + | Passable |
| 7 | + | Passable |
| 8 | + | Passable |
| 9 | + | Passable |
| 1c | + | Passable |
| 2c | + | Passable |
| 3c | + | Passable |
| 4c | + | Passable |
| 5c | − | Passable |
| 6c | − | Passable |
| 7c | − | Passable |
| 8c | − | Passable |

As shown in the column of "Storage stability", in the storage stability test where each test sample was stored for 60 days under a circumstance free of a relatively high temperature and humidity, test samples 1 to 9, and test samples 1c to 4c, which had a degree of crystallinity for trehalose of less than 90.0% and an average crystallite diameter of 2,850 Å or smaller, were judged as "Caked" (+), while test sample A and test samples 5c to 9c, which had a degree of crystallinity of 91.0% or more but not more than 96.0% and an average crystallite diameter of 3,210 Å or larger, were judged as "Not caked" (−). The results indicate that the test samples that were judged as "Caked" (+) or "Slightly caked" (±) in the caking tests conducted in Experiments 2-2 and 3-2, etc., are judged as "Caked" (+) in this storage test, while test samples that were judged as "Not caked" (−) in the caking tests conducted in Experiments 2-2 and 3-2, etc., are judged as "Not caked" (−) in this storage test. The fact indicates that the caking test conducted in Experiments 2-2 and 3-2, etc., is proper as a test for evaluating the cakeability of particulate compositions containing crystalline trehalose dihydrate under their actual storage circumstances.

As shown in the column of "Solubility in water" in Table 5, the solubility in water of test sample A, which had a degree of crystallinity of 100% and an average crystallite diameter of 3,910 Å, was judged as "Impassable", while those of test samples 1 to 9 and test samples 1c to 8c, which had a degree of crystallinity of 96.0% or lower and an average crystallite degree of 3,580 Å or lower, were all judged as "Passable". The result indicates that, when the degree of crystallinity and the average crystallite diameter of a particulate composition containing crystalline trehalose dihydrate are increased to the levels of test sample A, and in other words, when they are increased to the levels of a reagent-grade powder containing crystalline trehalose dihydrate, the solubility in water becomes worse as a different problem from cakeability.

<Experiment 6: Partial Amino Acid Sequences Common in CGTases More Suitable for Producing Trehalose>

To characterize a more suitable CGTase for producing trehalose, the amino acid sequences (SEQ ID NOs: 1 to 3) of the aforesaid CGTases, derived from microorganisms of the genus *Paenibacillus* having an improved effect of increasing the trehalose content in enzymatic reaction solutions, i.e., which are respectively derived from *Paenibacillus illinoisensis* NBRC15379 strain, *Paenibacillus pabuli*

NBRC13638 strain, and *Paenibacillus amylolyticus* NBRC15957 stain, were compared with the amino acid sequences (SEQ ID NOs: 4 to 6) of the CGTases, which are respectively derived from the aforesaid *Geobacillus stearothermophilus* Tc-91 strain and microorganisms of the species *Bacillus macerans* and *Thermoanaerobacter thermosulfurigenes*, which have a lower effect of increasing the trehalose content in an enzymatic reaction solution than those of the microorganisms of the genus *Paenibacillus*. All the amino acid sequences represented by SEQ ID NOs: 1 to 3, which were used in the above amino acid sequence comparison, are those which are encoded by the base sequences determined by the present applicant's independent cloning for the respective CGTase genes derived from *Paenibacillus illinoisensis* NBRC15379 strain, *Paenibacillus pabuli* NBRC13638 strain, and *Paenibacillus amylolyticus* NBRC15957 stain. The amino acid sequences of SEQ ID NOs: 4 and 5 are of the CGTases derived from *Geobacillus stearothermophilus* (*Bacillus stearothermophilus* as the old classification) Tc-91 strain, disclosed in Japanese Patent Kokai No. 135581/86 and determined independently by the same applicant as the present invention, and from a microorganism of the species *Bacillus macerans*. For comparison, although the amino acid sequence of SEQ ID NO: 5 is not for "CONTIZYME", a product name of a CGTase derived from a microorganism of the species *Bacillus macerans*, commercialized by Amano Enzyme Inc., Aichi, Japan, used in Experiment 1, it was used as a substitution because it is an amino acid sequence of a CGTase derived from a microorganism belonging to the same species *Bacillus macerans*. As the amino acid sequence of a CGTase derived from a microorganism of the species *Thermoanaerobacter thermosulfurigenes*, the one registered in "GenBank", a gene database, under the accession number of 35484 was used.

In the above-mentioned comparison of amino acid sequences, the following partial amino acid sequences of (a) to (d) were observed in CGTases that have a superior effect of increasing the trehalose content in an enzymatic reaction solution, i.e., such partial amino acid sequences commonly exist in the CGTases derived from the above microorganisms of the genus *Paenibacillus* but do not exist in CGTases, whose trehalose-content-increasing effects in enzymatic reaction solutions are not so high, namely CGTases derived from respective *Geobacillus stearothermophilus*, *Bacillus macerans*, and *Thermoanaerobacter thermosulfurigenes*:

(a) Gly-Ser-$X_1$-Ala-Ser-Asp;

(b) Lys-Thr-Ser-Ala-Val-Asn-Asn;

(c) Lys-Met-Pro-Ser-Phe-Ser-Lys; and (d) Val-Asn-Ser-Asn-$X_2$-Tyr.

(Wherein $X_1$ means Ala or Ser and $X_2$ means Ala or Thr, respectively.)

Based on the above results, CGTases which are more suitable for the process of producing trehalose of the present invention, namely CGTases, which can increase the trehalose content to over 86.0% in an enzymatic reaction solution, can be characterized to have the above-identified partial amino acid sequences of (a) to (d).

The present invention will be explained in more detail based on the following Examples but it should never be restricted thereby.

EXAMPLE 1

<Production of Particulate Composition Containing Crystalline Trehalose Dihydrate>

Corn starch was suspended in water to give a 30% suspension, admixed with calcium carbonate to give a final concentration of 0.1%, and adjusted to pH 6.0. To the resulting solution was added "TERMAMEAL 60L", a product name of a thermostable α-amylase specimen commercialized by Novozymes Japan Ltd., Tokyo, Japan, in an amount equal to 0.2% of the weight, d.s.b., of the starch, and subjected to an enzymatic reaction at 98 to 100° C. for 15 min to gelatinize and liquefy the starch. The resulting liquefied starch solution was autoclaved at 125° C. for 15 min, cooled to 51° C., admixed with a partially purified enzyme solution containing an α-glycosyltrehalose-forming enzyme and a trehalose-releasing enzyme, prepared by the method in Experiment 1-1, in respective amounts of 2 and 10 units/g starch, further admixed with an isoamylase produced by Hayashibara Co., Ltd., Okayama, Japan, in an amount of 300 units/g starch and a CGTase derived from *Paenibacillus illinoisensis* NBRC15959 strain, prepared by the method in Experiment 1-2, in an amount of two units/g starch, and further enzymatically reacted for about 70 hours. Thereafter, the enzymatic reaction solution was heated at 97° C. for 30 min to inactivate the remaining enzymes, adjusted to pH 4.5, admixed with "GLUCOZYME #20000", a product name of a glucoamylase specimen commercialized by Nagase ChemteX Corp., Osaka, Japan, in an amount of 10 units/g starch, and enzymatically reacted for 24 hours to obtain an enzymatic reaction solution with a trehalose purity or a trehalose content of 87.4%, d.s.b. The enzymatic reaction solution thus obtained was heated to inactivate the remaining enzyme and, in usual manner, decolored and filtered with an activated charcoal. The filtrate was desalted with a cation-exchange resin ($H^+$-form) and an anion-exchange resin ($OH^-$-form), concentrated in vacuo into a concentrate with a solid content of about 85%. The concentrate was placed in a crystallizer, admixed with "TREHALOSE 999" (Code No.: TH224, trehalose purity: 99.9% or higher), a product name of a reagent-grade powder containing crystalline trehalose dihydrate, commercialized by Hayashibara Co., Ltd., Okayama, Japan, as a seed crystal, in an amount equal to two percent of the solid contents, adjusted to 55° C., and unforcedly cooled to 15° C. over 24 hours under gentle stirring conditions to precipitate crystalline trehalose dihydrate. The crystals were collected by a basket-type centrifuge, spayed with refined water in an amount equal to about five percent of the weight of a massecuite, aged and dried at 50° C. for two hours, cooled by blowing 20° C. air for 10 min, and pulverized to obtain a particulate composition containing crystalline trehalose dihydrate, which contained, on a dry solid basis, 99.4% trehalose, 0.3% D-glucose, 0.06% 4-O-α-glucosyltrehalose, and 0.09% 6-O-α-glucosyltrehalose, in a production yield against starch of about 42%.

According to the production process of this example, a particulate composition containing crystalline trehalose dihydrate can be produced at a high production yield against starch of about 42%. The degree of crystallinity for crystalline trehalose dihydrate, the average crystallite diameter, and the reducing power of the whole particulate composition of the particulate composition containing crystalline trehalose dihydrate produced by the process of this example were respectively 88.4%, 2,850 Å, and 0.4%. For comparison, the measurement for the above degree of crystallinity was determined on the Hermans' method using the analytical values $H_{100}$ and $H_0$ obtained in Experiment 4-2. The measurement of the particle size distribution of the product revealed that it contained particles with a particle size of 53 µm or larger but smaller than 425 µm in an amount of 73.1%, those with a particle size of 53 µm or larger but smaller than 300 µm in an amount of 68.6%, and those with a particle size of 425 µm or larger in an amount of 8.2%. The product can be used as a material for food products, cosmetics, quasi-drugs, and pharmaceuticals similar to a conventional food-grade powder containing crystalline trehalose dihydrate.

EXAMPLE 2

<Production of Particulate Composition Containing Crystalline Trehalose Dihydrate>

An enzymatic reaction solution with a trehalose purity or a trehalose content of 87.6%, d.s.b., was obtained by conducting a trehalose-forming reaction and a glucoamylase treatment by a similar method as in Example 1, except for setting an enzymatic reaction of 40 hours by using an α-glycosyltrehalose-forming enzyme and a trehalose-releasing enzyme in respective amounts of 3 units and 15 units per g starch and using a CGTase derived from *Paenibacillus illinoisensis* NBRC15379 strain obtained by the method in Experiment 1-2. The enzymatic reaction solution thus obtained was heated to inactivate the remaining enzymes and, in usual manner, decolored and filtered with an activated charcoal. The filtrate was desalted with a cation-exchange resin ($H^+$-form) and an anion-exchange resin ($OH^-$-form), concentrated in vacuo into a concentrate with a solid content of about 85%. The concentrate was placed in a crystallizer, admixed with "TREHALOSE 999" (Code No.: TH224, trehalose purity: 99.9% or higher), a product name of a reagent-grade powder containing crystalline trehalose dihydrate, commercialized by Hayashibara Co., Ltd., Okayama, Japan, as a seed crystal, in an amount equal to one percent of the solid contents, and adjusted to 60° C. Thereafter, the resulting trehalose-containing solution was cooled up to 15° C. over a total time of 24 hours by a semi-controlled cooling method of successively cooling from 60° C. to 50° C. over 12 hours, from 50° C. to 40° C. over six hours, and then from 40° C. to 15° C. over six hours under gentle stirring conditions to precipitate crystalline trehalose dihydrate. The crystals were collected by a basket-type centrifuge, spayed with refined water in an amount equal to about 5% of the weight of a massecuite, aged and dried at 50° C. for two hours, cooled by blowing 20° C. air for 20 min, and pulverized to obtain a particulate composition containing crystalline trehalose dihydrate, which contained, on a dry solid basis, 99.6% trehalose, 0.07% D-glucose, 0.04% 4-O-α-glucosyltrehalose, and 0.06% 6-O-α-glucosyltrehalose, in a production yield against starch of about 45%.

The degree of crystallinity for crystalline trehalose dihydrate, the average crystallite diameter, and the reducing power of the whole particulate composition of the particulate composition containing crystalline trehalose dihydrate produced were respectively 95.6%, 3,520 Å, and 0.15%. For comparison, the measurement for the above degree of crystallinity was determined on the Hermans' method using the analytical values $H_{100}$ and $H_0$ obtained in Experiment 4-2. The measurement of the particle size distribution of the product revealed that it contained particles with a particle size of 53 µm or larger but smaller than 425 µm in an amount of 83.3%, those with a particle size of 53 µm or larger but smaller than 300 µm in an amount of 72.5%, and those with a particle size of 425 µm or larger in an amount of 6.9%.

When subjected to a caking test by the same method as in Experiments 2-2, 3-2, etc., the product was judged as "Not caked" (−). Also, the product was judged as "Passable" when tested for solubility in water by the same method as in Experiment 5.

According to the production process of this example, a particulate composition containing crystalline trehalose dihydrate can be produced in a production yield against starch of as high as about 45%. Although, in terms of the purity of trehalose, the particulate composition containing crystalline trehalose dihydrate produced by the process of this example is not so different from "TREHA", a product name of a conventional food-grade powder containing crystalline trehalose dihydrate, commercialized by Hayashibara Co., Ltd., Okayama, Japan, as a food material or the like, it is a significantly, hardly cakeable particulate composition compared to the conventional food-grade powder, as well as being easily stored and handled. The product is similar to the conventional food-grade powder in that it is a particulate composition containing crystalline trehalose dihydrate; the more easily stored and handled, the more preferably used as a material for food products, cosmetics, quasi-drugs, pharmaceuticals, etc.

EXAMPLE 3

<Production of Particulate Composition Containing Crystalline Trehalose Dihydrate>

When a trehalose-forming reaction was carried out similarly as in Example 1 except for using, as a CGTase, the one derived from *Paenibacillus pabuli* NBRC13638 strain prepared by the method in Experiment 1-2, the trehalose content in the resulting enzymatic reaction solution after glucoamylase treatment was 87.2%, d.s.b. The enzymatic reaction solution thus obtained was heated to inactivate the remaining enzyme and, in usual manner, decolored and filtered with an activated charcoal. The filtrate was desalted with a cation-exchange resin ($H^+$-form) and an anion-exchange resin ($OH^-$-form), concentrated in vacuo into a concentrate with a solid content of about 85%. The concentrate was placed in a crystallizer, admixed with "TREHALOSE 999" (Code No.: TH224, trehalose purity: 99.9% or higher), a product name of a reagent-grade powder containing crystalline trehalose dihydrate, commercialized by Hayashibara Co., Ltd., Okayama, Japan, as a seed crystal, in an amount equal to one percent of the solid contents, adjusted to 60° C., and cooled over 24 hours in such a manner of cooling from 60° C. to 45° C. over 15 hours and from 45° C. to 20° C. over 9 hours under gentle stirring conditions by a two-step semi-controlled cooling method to precipitate crystalline trehalose dihydrate. The crystals were collected by a basket-type centrifuge, spayed with refined water in an amount equal to about 5% of the weight of a massecuite, aged and dried at 50° C. for two hours, cooled by blowing 20° C. air for 10 min, and pulverized to obtain a particulate composition containing crystalline trehalose dihydrate, which contained, on a dry solid basis, 99.2% trehalose, 0.4% D-glucose, 0.06% 4-O-α-glucosyltrehalose, and 0.10% 6-O-α-glucosyltrehalose, in a production yield against starch of about 44%.

The degree of crystallinity for crystalline trehalose dihydrate, the average crystallite diameter, and the reducing power of the whole particulate composition of the particulate composition containing crystalline trehalose dihydrate were respectively 92.6%, 3,130 Å, and 0.5%. For comparison, the measurement for the above degree of crystallinity was determined on the Hermans' method using the analytical values $H_{100}$ and $H_0$ obtained in Experiment 4-2. The measurement of the particle size distribution of the product revealed that it contained particles with a particle size of 53 µm or larger but smaller than 425 µm in an amount of 75.2%, those with a particle size of 53 µm or larger but smaller than 300 µm in an amount of 69.3%, and those with a particle size of 425 µm or larger in an amount of 7.8%. When subjected to a caking test by the same method as in Experiments 2-2, 3-2, etc., the product was judged as "Not caked" (−). Also, the product was judged as "Passable" when tested for solubility in water by the same method as in Experiment 5.

According to the production process of this example, a particulate composition containing crystalline trehalose dihydrate can be produced in a high production yield against starch of about 44%. Although, in terms of the purity of trehalose, the particulate composition containing crystalline trehalose dihydrate produced by the process of this example is not so different from "TREHA", a product name of a conventional food-grade powder containing crystalline trehalose dihydrate, commercialized by Hayashibara Co., Ltd., Okayama, Japan, as a food material or the like, it is a significantly, hardly cakeable particulate composition compared to the conventional food-grade powder, as well as being easily stored and handled. The product is similar to the conventional food-grade powder in that it is a particulate composition containing crystalline trehalose dihydrate; the more easily stored and handled, the more preferably used as a material for food products, cosmetics, quasi-drugs, pharmaceuticals, etc.

EXAMPLE 4

<Production of Particulate Composition Containing Crystalline Trehalose Dihydrate>

An enzymatic reaction solution with a trehalose purity or a trehalose content of 86.6%, d.s.b., was obtained by conducting a trehalose-forming reaction and a glucoamylase treatment similarly as the method in Example 1, except for using tapioca starch as a material starch and a CGTase derived from *Paenibacillus amylolyticus* NBRC15957 strain, as a CGTase, obtained by the method in Experiment 1-2. The enzymatic reaction solution thus obtained was heated to inactivate the remaining enzyme and, in usual manner, decolored and filtered with an activated charcoal. The filtrate was desalted with a cation-exchange resin ($H^+$-form) and an anion-exchange resin ($OH^-$-form), concentrated in vacuo into a concentrate with a solid content of about 86%. The concentrate was placed in a crystallizer, admixed with "TREHALOSE 999" (Code No.: TH224, trehalose purity: 99.9% or higher), a product name of a reagent-grade powder containing crystalline trehalose dihydrate, commercialized by Hayashibara Co., Ltd., Okayama, Japan, as a seed crystal, in an amount equal to one percent of the solid contents, adjusted to 60° C., and cooled to 15° C. over 24 hours in total in such a manner of cooling from 60° C. to 50° C. over eight hours, from 50° C. to 35° C. over eight hours, and from 35° C. to 15° C. over eight hours under gentle stirring conditions by a three-step semi-controlled cooling method to precipitate crystalline trehalose dihydrate. The crystals were collected by a basket-type centrifuge, spayed with refined water in an amount equal to about 5% of the weight of a massecuite, aged and dried at 50° C. for two hours, cooled by blowing 20° C. air for 20 min, and pulverized to obtain a particulate composition containing crystalline trehalose dihydrate, which contained, on a dry solid basis, 99.4% trehalose, 0.06% D-glucose, 0.04% 4-O-α-glucosyltrehalose, and 0.06% 6-O-α-glucosyltrehalose, in a production yield against starch of about 43%.

The degree of crystallinity for crystalline trehalose dihydrate, the average crystallite diameter, and the reducing power of the whole particulate composition of the particulate composition containing crystalline trehalose dihydrate were respectively 93.3%, 3,280 Å, and 0.13%. For comparison, the measurement for the above degree of crystallinity was determined on the Hermans' method using the analytical values $H_{100}$ and $H_0$ obtained in Experiment 4-2. The measurement of the particle size distribution of the product revealed that it contained particles with a particle size of 53 µm or larger but smaller than 425 µm in an amount of 80.7%, those with a particle size of 53 µm or larger but smaller than 300 µm in an amount of 74.4%, and those with a particle size of 425 µm or larger in an amount of 7.1%. When subjected to a caking test by the same method as in Experiments 2-2, 3-2, etc., the product was judged as "Not caked" (−). Also, the product was judged as "Passable" when tested for solubility in water by the same method as in Experiment 5.

According to the production process of this example, a particulate composition containing crystalline trehalose dihydrate can be produced in a production yield against starch of as high as about 43%. Although, in terms of the purity of trehalose, the particulate composition containing crystalline trehalose dihydrate produced by the process of this example is not so different from "TREHA", a product name of a conventional food-grade powder containing crystalline trehalose dihydrate, commercialized by Hayashibara Co., Ltd., Okayama, Japan, as a food material or the like, it is a significantly, hardly cakeable particulate composition compared to the conventional food-grade powder, as well as being easily stored and handled. The product is similar to the conventional food-grade powder in that it is a particulate composition containing crystalline trehalose dihydrate; the more easily stored and handled, the more preferably used as a material for food products, cosmetics, quasi-drugs, pharmaceuticals, etc.

EXAMPLE 5

<Preparation of Recombinant CGTase and Mutant CGTase and Production of Particulate Composition Containing Crystalline Trehalose Dihydrate by Using the Same>

A production of a particulate composition containing crystalline trehalose dihydrate was conducted by using, in place of the CGTase derived from *Paenibacillus illinoisensis* NBRC15379 strain used in Example 2, two types of enzymes of a recombinant (wild type) CGTase obtained by expressing a CGTase gene derived from the above microorganism in *E. coli* as a host, and a mutant CGTase, having a replacement of one amino acid residue in the amino acid sequence with other amino acid residue, prepared by introducing a site-specific mutagenesis into the above wild-type CGTase.

<Preparation of Recombinant CGTase>

Figure 6:
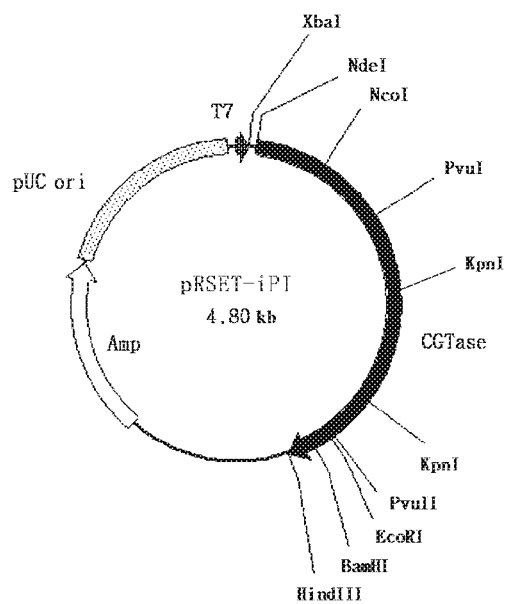
FIG. 6 is a figure of the structure and the restriction enzyme recognition sites of a recombinant DNA "pRSET-iPI", which contains a CGTase gene derived from *Paenibacillus illinoisensis* NBRC15379 strain.

By using a CGTase gene having the base sequence of SEQ ID NO: 7, derived from *Paenibacillus illinoisensis* NBRC15379 strain, which had been cloned from the microorganism and possessed by the present inventors, a recombinant DNA for expression, which contains a gene encoding a natural (wild type) CGTase, was constructed by mutating the above CGTase gene without altering the amino acid sequence encoded by the CGTase gene to introduce or delete a restriction enzyme site (s), etc., and recombining the resultant into an expression plasmid vector "pRSET-A", produced by Invitrogen Corporation, CA, USA. The structure of the obtained recombinant DNA "pRSET-iPI" is shown in FIG. 6. *E. coli* BL21 (DE3), produced by Stratagene, CA, USA, was transformed in usual manner with the recombinant DNA "pRSET-iPI" to obtain a transformant "BL21-RSET-iPI" having the recombinant DNA. Thereafter, the transformant was aerobically cultured at 37° C. for 24 hours in T medium (containing 12 g bacto-tryptone, 24 g bacto-yeast extract, 5 ml of glycerol, 17 mM potassium phosphate, and 72 mM dipotassium phosphate per liter of the medium) containing 100 µl/ml of ampicillin (Na-salt). The resulting culture was centrifuged, and the obtained cells were subjected to a disruption treatment with "ULTRA SONIC HOMOGENIZER UH-600", a product name of an ultrasonic disruptor, commercialized by MST Co., Ltd., Tokyo, Japan, and centrifuged, followed by assaying the supernatant for CGTase activity (starch decomposing activity) to have an enzymatic activity of about 12.8 units/ml when converted into the activity per one milliliter of the culture liquid. The supernatant of the disrupted solution was in usual manner salted out with ammonium sulfate and dialyzed to obtain a crude enzyme solution of a recombinant CGTase, followed by purifying the crude enzyme solution by subjecting it to an anion-exchange column chromatography using DEAE-TOYOPEARL 650S GEL, produced by Tosoh Corp., Tokyo, Japan, and a hydrophobic column chromatography using BUTYL-TOYOPEARL 650M GEL commercialized by Tosoh Corp., Tokyo, Japan, into a partially purified specimen of a recombinant CGTase.

<Preparation of Mutant CGTase>

Two types of mutant CGTases with one amino acid substitution was prepared by introducing a site specific mutation into a natural (wild type) CGTase gene derived from the above-identified *Paenibacillus illinoisensis* NBRC15379 strain in usual manner, and expressing the obtained mutant CGTase gene in *E. coli*. When in introducing the amino acid substitution into the CGTase, any aminoacid substitution mutation is avoided from the following sites and a mutation site is selected from those other than the following sites: The amino acid residues from the $133^{rd}$ aspartic acid residue to the $138^{th}$ histidine residue (Asp 133 to His 138), from the $223^{rd}$ glycine residue to the $231^{st}$ histidine residue (Gly 223 to His 231), from the $255^{th}$ glutamic acid residue to the $258^{th}$ leucine residue (Glu 255 to Leu 258), and from the $321^{st}$ phenylalanine residue to the $326^{th}$ aspartic acid residue (Phe 321 to Asp 326) in the amino acid sequence of SEQ ID NO: 1 corresponding to the amino acid sequence of a CGTase derived from *Paenibacillus illinoisensis* NBRC15379 strain, i.e., amino acid sequences corresponding to four conserved regions commonly conserved in the enzyme group classified as α-amylase family; and the amino acid residues from the $259^{th}$ glycine residue to the $264^{th}$ aspartic acid residue (Gly 269 to Asp 264), from the $331^{st}$ lysine residue to the $337^{th}$ asparagine residue (Lys 331 to Asp 337), from the $375^{th}$ lysine residue to the $381^{st}$ lysine residue (Lys 375 to Lys 381), and from the $567^{th}$ valine residue to the $572^{nd}$ tyrosine residue (Val 567 to Tyr 572) in the amino acid sequence of SEQ ID NO: 1, i.e., the above-identified partial amino acid sequences of (a) to (d) which are characteristic to CGTases derived from microorganisms of the genus *Paenibacillus*.

Based on the above guideline, the following two types of mutant CGTases were decided to prepare; a mutant CGTase (G178R) with the amino acid sequence of SEQ ID NO: 1 wherein the $178^{th}$ glycine residue was replaced with arginine residue, and a mutant CGTase (Y454H) with the amino acid sequence of SEQ ID NO: 1 wherein the $454^{th}$ tyrosine residue was replaced with histidine residue. A recombinant DNA "pRSET-iPI (G178R)" encoding a mutant CGTase (G178R) was obtained by using as a genetic template a recombinant DNA "pRSET-iPI" having a natural (wild type) CGTase gene derived from *Paenibacillus illinoisensis* NBRC15379 strain and using synthetic oligonucleotides having the base sequences of SEQ ID NOs: 8 and 9 as a sense- and anti-sense-primers, respectively; and introducing a site specific mutation into the CGTase gene by conventional PCR and Dpn1 methods using a commercialized "QuickChange Site-Directed Mutagenesis Kit" produced by Stratagene, CA, USA. A DNA "pRSET-iPI (Y454H)" encoding the mutant CGTase (Y454H) was obtained similarly as above except for using synthetic oligonucleotides having the base sequences of SEQ ID NOs: 10 and 11 as a sense- and anti-sense-primers, respectively.

*E. coli* BL21 (DE3), produced by Stratagene, CA, USA, was transformed in usual manner by using the recombinant DNA "pRSET-iPI (G178R)" or "pRSET-iPI (Y454H)", which had a mutant CGTase gene, to obtain transformants of "BL21-RSET-iPI (G178R)" and "BL21-RSET-iPI (Y454H)", which had the above respective recombinant DNAs. Similarly as the above "BL21-RSET-iPI", these transformants were respectively cultured, followed by disrupting the cells and partially purifying the resultants to obtain partially purified specimens of the mutant CGTases, respectively. By the way, the supernatants of each cell disruption solutions were assayed for CGTase activity (starch hydrolyzing activity) and converted into enzyme activities per milliliter of the culture solutions, revealing that they had about 10.3 units/ml for "BL21-RSET-iPI (G178R)" and about 13.7 units/ml for "BL21-RSET-iPI (Y454H)".

<Production of Particulate Composition Containing Crystalline Trehalose Dihydrate>

A particulate composition containing crystalline trehalose dihydrate was produced by the method similarly as in Example 2 except for using the recombinant (wild type) CGTase, and, as a mutant CGTase, G178R, a CGTase having the amino acid sequence of SEQ ID NO: 12; or Y454H, a CGTase having the amino acid sequence of SEQ ID NO: 13, both of which were all obtained in the above. The trehalose contents in the enzymatic reaction solutions obtained by using the respective CGTases, saccharide compositions of the obtained particulate compositions containing crystalline trehalose dihydrate, production yields against starch, degrees of crystallinity for crystalline trehalose dihydrate, average crystallite diameters, reducing powders of the whole powders, and particle size distributions were determined; and the particulate compositions were subjected to both a caking test by the same method as in Experiments 2-2, 3-2, etc., and a test for solubility in water by the same method as in Experiment 5. The results are tabulated in Table 6.

TABLE 6

| | | CGTase | | |
|---|---|---|---|---|
| Item | | Recombinant enzyme (wild type) | Mutant enzyme G178R | Mutant enzyme Y454H |
| Trehalose content in enzymatic reaction solution* (% by weight) | | 87.2 | 87.0 | 87.6 |
| Saccharide composition (% by weight**) | Trehalose | 99.4 | 99.3 | 99.4 |
| | D-Glucose | 0.08 | 0.07 | 0.07 |
| | 4-O-α-Glucosyltrehalose | 0.04 | 0.05 | 0.03 |
| | 6-O-α-Glucosyltrehalose | 0.07 | 0.06 | 0.08 |

TABLE 6-continued

| Item | | CGTase | | |
|---|---|---|---|---|
| | | Recombinant enzyme (wild type) | Mutant enzyme G178R | Mutant enzyme Y454H |
| Production yield against starch (% by weight) | | 45 | 44 | 45 |
| Degree of crystallinity (%) | | 94.4 | 94.9 | 95.1 |
| Average crystallite diameter (Å) | | 3380 | 3430 | 3550 |
| Reducing power of the whole powder (%) | | 0.16 | 0.15 | 0.16 |
| Particle size distribution (% by weight) | 53 μm or larger but smaller than 425 μm | 82.1 | 82.6 | 84.4 |
| | 53 μm or larger but smaller than 300 μm | 73.4 | 74.7 | 71.5 |
| | 425 μm or larger | 6.7 | 6.2 | 6.6 |
| Caking test | | — | — | — |
| Solubility in water | | Passable | Passable | Passable |

*After glucoamylase treatment
**On a dry solid basis

As shown in Table 6, even in the case of using the recombinant CGTase and the mutant CGTases with one amino acid substitution, the trehalose contents in the enzymatic reaction solutions are substantially the same level of 87.0% or more as in the case of natural CGTase; and particulate compositions, containing crystalline trehalose dihydrate having substantially the same trehalose purity, degree of crystallinity, particle size distribution, etc., can be produced in a production yield against starch of as high as about 44% to about 45% according to the same production process. Similarly as the particulate compositions containing crystalline trehalose dihydrate produced with the natural CGTases in Examples 1 to 4, although the particulate compositions containing crystalline trehalose dihydrate produced in the production process of this example are not so different from "TREHA", a conventional food-grade powder containing crystalline trehalose dihydrate, commercialized by Hayashibara Co., Ltd., Okayama, Japan, which has been commercialized as a food material, etc., in terms of trehalose purity, they are significantly, hardly cakeable particulate compositions compared to the conventional food-grade powder, as well as being easily stored and handled.

EXAMPLE 6

A particulate composition containing crystalline trehalose dihydrate, containing, on a dry solid basis, 99.7% trehalose, 0.05% D-glucose, 0.03% 4-O-α-glucosyltrehalose, and 0.05% 6-O-α-glucosyltrehalose, was obtained in a production yield against starch of about 46% by the method similarly as in Example 2 except for precipitating crystalline trehalose dihydrate by applying a controlled cooling method of cooling the contents over 24 hours by a 20-step cooling profile approximated to the aforesaid Equation [2] in such a manner of cooling the contents from 60° C. to 20° C. by using, in the crystallization step for crystalline trehalose dihydrate, a conventional programmed-constant-temperature-circulator for crystallization system and flowing a temperature-controlled heat medium to a jacket of a crystallizer.

The particulate composition containing crystalline trehalose dihydrate had the degree of crystallinity for crystalline trehalose dihydrate of 96.8%, an average crystallite diameter of 3,680 Å, and a reducing power of the whole powder of 0.13%. For comparison, the determination of the above degree of crystallinity was carried out by the Hermans' method using the analytical values $H_{100}$ and $H_0$ determined in Experiment 4-2. The measurement of particle size distribution of the particulate composition revealed that it contained particles with a particle size of 53 μm or larger but smaller than 425 μm in an amount of 84.5%, those with a particle size of 53 μm or larger but smaller than 300 μm in an amount of 76.2%, and those with a particle size of 425 μm or larger in an amount of 6.4%. When subjected to a caking test by the same method as in Experiments 2-2, 3-2, etc., the particulate composition was judged as "Not caked" (−). Also, the particulate composition was judged as "Passable" when tested for solubility in water by the same method as in Experiment 5.

According to the production process of this example, a particulate composition containing crystalline trehalose dihydrate is produced in a production yield against starch of as high as about 46%. Although the particulate composition containing crystalline trehalose dihydrate produced by the process of this example is not so different from "TREHA", a product name of a conventional food-grade powder containing crystalline trehalose dihydrate, commercialized by Hayashibara Co., Ltd., Okayama, Japan, which has been commercialized as a food material, etc., in terms of trehalose purity, it is a significantly, hardly cakeable particulate composition compared to the conventional food-grade powder, as well as being easily stored handled. The product is similar to the conventional food-grade powder in that it is a particulate composition containing crystalline trehalose dihydrate; the more easily stored and handled, the more preferably used as a material for food products, cosmetics, quasi-drugs, pharmaceuticals, etc.

Example for Reference

<Production of Particulate Composition Containing Crystalline Trehalose Dihydrate>

When conducting a trehalose-forming reaction and a glucoamylase treatment similarly as in Example 1 except for using, as a CGTase, a CGTase enzyme specimen derived from *Geobacillus stearothermophilus* Tc-91 strain, produced by Hayashibara Co., Ltd., Okayama, Japan, an enzymatic reaction solution after glucoamylase treatment had a trehalose content of 85.2%, d.s.b. The enzymatic reaction solution was in usual manner decolored and filtered with an activated charcoal, and the filtrate was desalted with a cation-exchange resin ($H^+$-form) and an anion-exchange resin ($OH^-$-form), concentrated in vacuo into a concentrate with a solid content of about 84%. The concentrate was placed in a crystallizer, admixed with "TREHALOSE 999" (Code No.: TH224, trehalose purity: 99.9% or higher), a product name of a reagent-grade powder containing crystalline trehalose dihydrate, commercialized by Hayashibara Co., Ltd., Okayama, Japan, as a seed crystal, in an amount equal to one percent of the solid contents, adjusted to 55° C., and unforcedly cooled from 55° C. to 15° C. over 20 hours under gentle stirring conditions to precipitate crystalline trehalose dihydrate. The crystals were collected by a basket-type centrifuge, spayed with refined water in an amount equal to about 5% of the weight of a massecuite, aged and dried at 50° C. for two hours, cooled by blowing 20° C. air for 20 min, and pulverized to obtain a particulate composition containing crystalline trehalose dihydrate, which contained, on a dry solid basis, 98.5% trehalose, 0.8% D-glucose, 0.07% 4-O-α-glucosyltrehalose, and 0.1% 6-O-α-glucosyltrehalose, in a production yield against starch of about 38%.

The degree of crystallinity for crystalline trehalose dihydrate, the average crystallite diameter, and the reducing power of the whole powder of the particulate composition containing crystalline trehalose dihydrate were respectively 88.3%, 2,580 Å, and 1.0%. For comparison, the measurement for the above degree of crystallinity was determined on the Hermans' method using the analytical values $H_{100}$ and $H_0$ obtained in Experiment 4-2. The measurement of the particle size distribution of the product revealed that it contained particles with a particle size of 53 μm or larger but smaller than 425 μm in an amount of 74.4%, those with a particle size of 53 μm or larger but smaller than 300 μm in an amount of 69.4%, and those with a particle size of 425 μm or larger in an amount of 12.6%. When subjected to a caking test by the same method as in Experiments 2-2, 3-2, etc., the product was judged as "Slightly caked" (±). Also, the product was judged as "Passable" when tested for solubility in water by the same method as in Experiment 5.

INDUSTRIAL APPLICABILITY

As described above, according to the production process for producing particulate compositions containing anhydrous crystalline trehalose dihydrate, those which are relatively high in purity similarly as in conventional food-grade powder containing crystalline trehalose dihydrate and are hardly cakeable, can be produced in a high production yield against starch. In particular, when a controlled cooling method or semi-controlled cooling method is applied in the crystallization step for crystalline trehalose dihydrate, particulate compositions containing a higher purity crystalline trehalose dihydrate are produced in a higher production yield against starch. As described above, the production process according to the present invention enables to more efficiently produce particulate compositions containing crystalline trehalose dihydrate on an industrial scale by using starch, as a material, which is present abundantly but a restricted source, and thus it has a particular industrial utility. The particulate compositions containing crystalline trehalose dihydrate produced by the production process of the present invention, which employs a controlled cooling method or semi-controlled cooling method, are significantly, hardly cakeable particulate compositions compared to the conventional food-grade powders containing crystalline trehalose dihydrate, and they have a superior industrial availability in that they can be used in various uses as more readily handleable powdered materials for food products, cosmetics, quasi-drugs, or pharmaceuticals. Thus, the present invention, which has such an outstanding functions and effects, has distinct industrial utilities.

EXPLANATION OF SYMBOLS

In FIG. 1, the symbols "a" to "e" mean as follows:
a: a diffraction peak at a diffraction angle (2θ) of 13.7° (Miller's index (hkl): 101) for calculating crystallite diameter;
b: a diffraction peak at a diffraction angle (2θ) of 17.5° (Miller's index (hkl): 220) for calculating crystallite diameter;
c: a diffraction peak at a diffraction angle (2θ) of 21.1° (Miller's index (hkl): 221) for calculating crystallite diameter;
d: a diffraction peak at a diffraction angle (2θ) of 23.9° (Miller's index (hkl): 231) for calculating crystallite diameter; and
e: a diffraction peak at a diffraction angle (2θ) of 25.9° (Miller's index (hkl): 150) for calculating crystallite diameter.

In FIG. 5, the symbols "a" to "c" mean as follows:
a: Controlled cooling curve;
b: Linear cooling; and
c: Unforced cooling curve.

In FIG. 6, the following symbols mean as follows:
pUC ori: Replication origin derived from plasmid pUC;
T7: T7 Promotor;
White arrow (Amp): Ampicillin-resistant gene; and
Black arrow: CGTase Gene.

---

The invention claimed is:

1. A process for producing a particulate composition comprising crystalline α,α-trehalose dihydrate with an α,α-trehalose content of 98.0% by weight or more, on a dry solid basis, said process comprising the steps of:

allowing to act on liquefied starch an α-glycosyltrehalose-forming enzyme and a trehalose-releasing enzyme along with a starch debranching enzyme and a cyclomaltodextrin glucanotransferase;

allowing a glucoamylase to act on the resulting mixture to obtain a saccharide solution comprising α,α-trehalose;

precipitating crystalline α,α-trehalose dihydrate from said saccharide solution by a controlled cooling method or semi-controlled cooling method;

collecting the precipitated crystalline α,α-trehalose dihydrate by a centrifuge; and ageing and drying the collected crystals to obtain a particulate composition comprising crystalline α,α-trehalose dihydrate, wherein said cyclomaltodextrin glucanotransferase has the following partial amino acid sequences of (a) to (d):

(a) Gly-Ser-$X_1$-ALa-Ser-Asp;

(b) Lys-Thr-Ser-Ala-Val-Asn-Asn;

(c) Lys-Met-Pro-Ser-Phe-Ser-Lys; and (d) Val-Asn-Ser-Asn-$X_2$-Tyr, wherein $X_1$ means Ala or Ser and $X_2$ means Ala or Thr, respectively, and
said cyclomaltodextrin glucanotransferase is used to increase the α,α-trehalose content in said saccharide solution to over 86.0% by weight, on a dry solid basis, without passing through a fractionation step by column chromatography.

2. The process of claim 1, wherein said α-glycosyltrehalose-forming enzyme and said trehalose-releasing enzyme are derived from a microorganism of the genus *Arthrobacter*.

3. The process of claim 1, wherein said cyclomaltodextrin glucanotransferase is a natural or recombinant enzyme derived from a microorganism of the genus *Paenibacillus* or a mutant enzyme thereof.

4. The process of claim 1, wherein said cyclomaltodextrin glucanotransferase is the one that has an amino acid sequence of SEQ ID NO: 1, 2, 3, 12 or 13.

5. The process of claim 1, wherein said controlled cooling method is a cooling method where the liquid temperature "T" at the time "t" is basically expressed by the formula:

$$T=T_0-(T_0-T_f)(t/\tau)^3,$$

wherein "τ" is the operation time established for a crystallization step, "$T_0$" is the liquid temperature at the initiation of crystallization, and "$T_f$" is the targeted liquid temperature at the termination of crystallization; and wherein said semi-controlled cooling method is a cooling method, where the liquid temperature "T" is allowed to linearly or stepwisely decrease against the time "t" in order to keep the variation ($T_0-T_m$) of the liquid temperature "T" at the point of "t=τ/2" to be at least 5% but less than 50% of the total temperature change ($T_0-T_f$), and wherein "Tm" is the liquid temperature at time "t=τ/2".

6. The process of claim 1, wherein said particulate composition has a degree of crystallinity for crystalline α,α-trehalose dihydrate of 90.0% or higher, when calculated based on its powder X-ray diffraction profile.

* * * * *

SEQUENCE LISTING

```
<160> NUMBER OF SEQ ID NOS: 13

<210> SEQ ID NO 1
<211> LENGTH: 682
<212> TYPE: PRT
<213> ORGANISM: Paenibacillus illinoisensis

<400> SEQUENCE: 1

Asp Thr Ala Val Thr Asn Lys Gln Asn Phe Ser Thr Asp Val Ile Tyr
1               5                   10                  15

Gln Val Phe Thr Asp Arg Phe Leu Asp Gly Asn Pro Ser Asn Asn Pro
            20                  25                  30

Thr Gly Ala Ala Phe Asp Gly Thr Cys Ser Asn Leu Lys Leu Tyr Cys
        35                  40                  45

Gly Gly Asp Trp Gln Gly Leu Ile Asn Lys Ile Asn Asp Asn Tyr Phe
    50                  55                  60

Ser Asp Leu Gly Val Thr Ala Leu Trp Ile Ser Gln Pro Val Glu Asn
65                  70                  75                  80

Ile Phe Ala Thr Ile Asn Tyr Ser Gly Val Thr Asn Thr Ala Tyr His
                85                  90                  95

Gly Tyr Trp Ala Arg Asp Phe Lys Lys Thr Asn Pro Tyr Phe Gly Thr
            100                 105                 110
```

```
Met Thr Asp Phe Gln Asn Leu Val Thr Ser Ala His Ala Lys Gly Ile
            115                 120                 125
Lys Ile Ile Ile Asp Phe Ala Pro Asn His Thr Phe Pro Ala Met Glu
        130                 135                 140
Thr Asp Thr Ser Phe Ala Glu Asn Gly Lys Leu Tyr Asp Asn Gly Ser
145                 150                 155                 160
Leu Val Gly Gly Tyr Thr Asn Asp Thr Asn Gly Tyr Phe His His Asn
                165                 170                 175
Gly Gly Ser Asp Phe Ser Thr Leu Glu Asn Gly Ile Tyr Lys Asn Leu
            180                 185                 190
Tyr Asp Leu Ala Asp Leu Asn His Asn Asn Ser Thr Ile Asp Thr Tyr
        195                 200                 205
Phe Lys Asp Ala Ile Lys Leu Trp Leu Asp Met Gly Val Asp Gly Ile
        210                 215                 220
Arg Val Asp Ala Val Lys His Met Pro Gln Gly Trp Gln Lys Asn Trp
225                 230                 235                 240
Met Ser Ser Ile Tyr Ala His Lys Pro Val Phe Thr Phe Gly Glu Trp
                245                 250                 255
Phe Leu Gly Ser Ala Ala Ser Asp Ala Asp Asn Thr Asp Phe Ala Asn
            260                 265                 270
Glu Ser Gly Met Ser Leu Leu Asp Phe Arg Phe Asn Ser Ala Val Arg
        275                 280                 285
Asn Val Phe Arg Asp Asn Thr Ser Asn Met Tyr Ala Leu Asp Ser Met
        290                 295                 300
Leu Thr Ala Thr Ala Ala Asp Tyr Asn Gln Val Asn Asp Gln Val Thr
305                 310                 315                 320
Phe Ile Asp Asn His Asp Met Asp Arg Phe Lys Thr Ser Ala Val Asn
                325                 330                 335
Asn Arg Arg Leu Glu Gln Ala Leu Ala Phe Thr Leu Thr Ser Arg Gly
            340                 345                 350
Val Pro Ala Ile Tyr Tyr Gly Thr Glu Gln Tyr Leu Thr Gly Asn Gly
        355                 360                 365
Asp Pro Asp Asn Arg Gly Lys Met Pro Ser Phe Ser Lys Ser Thr Thr
370                 375                 380
Ala Phe Ser Val Ile Ser Lys Leu Ala Pro Leu Arg Lys Ser Asn Pro
385                 390                 395                 400
Ala Ile Ala Tyr Gly Ser Thr Gln Gln Arg Trp Ile Asn Asn Asp Val
                405                 410                 415
Tyr Ile Tyr Glu Arg Lys Phe Gly Lys Ser Val Ala Val Val Ala Val
            420                 425                 430
Asn Arg Asn Leu Thr Thr Pro Thr Ser Ile Thr Asn Leu Asn Thr Ser
        435                 440                 445
Leu Pro Ser Gly Thr Tyr Thr Asp Val Leu Gly Gly Val Leu Asn Gly
        450                 455                 460
Asn Asn Ile Thr Ser Ser Gly Asn Ile Ser Ser Phe Thr Leu Ala
465                 470                 475                 480
Ala Gly Ala Thr Ala Val Trp Gln Tyr Thr Ala Ser Glu Thr Thr Pro
                485                 490                 495
Thr Ile Gly His Val Gly Pro Val Met Gly Lys Pro Gly Asn Val Val
            500                 505                 510
Thr Ile Asp Gly Arg Gly Phe Gly Ser Thr Lys Gly Thr Val Tyr Phe
        515                 520                 525
Gly Thr Thr Ala Val Thr Gly Ser Ala Ile Thr Ser Trp Glu Asp Thr
```

```
                530             535             540
Gln Ile Lys Val Thr Ile Pro Pro Val Ala Gly Gly Asp Tyr Ala Val
545                 550                 555                 560

Lys Val Ala Ala Asn Gly Val Asn Ser Asn Ala Tyr Asn Asp Phe Thr
                565                 570                 575

Ile Leu Ser Gly Asp Gln Val Ser Val Arg Phe Val Ile Asn Asn Ala
                580                 585                 590

Thr Thr Ala Leu Gly Glu Asn Ile Tyr Leu Thr Gly Asn Val Ser Glu
                595                 600                 605

Leu Gly Asn Trp Thr Thr Gly Ala Ala Ser Ile Gly Pro Ala Phe Asn
610                 615                 620

Gln Val Ile His Ala Tyr Pro Thr Trp Tyr Tyr Asp Val Ser Val Pro
625                 630                 635                 640

Ala Gly Lys Gln Leu Glu Phe Lys Phe Lys Lys Asn Gly Ala Thr
                645                 650                 655

Ile Thr Trp Glu Gly Gly Ser Asn His Thr Phe Thr Thr Pro Thr Ser
                660                 665                 670

Gly Thr Ala Thr Val Thr Val Asn Trp Gln
                675                 680
```

<210> SEQ ID NO 2
<211> LENGTH: 683
<212> TYPE: PRT
<213> ORGANISM: Paenibacillus pabuli

<400> SEQUENCE: 2

```
Asp Thr Ala Val Thr Asn Lys Gln Asn Phe Ser Thr Asp Val Ile Tyr
1               5                   10                  15

Gln Val Phe Thr Asp Arg Phe Leu Asp Gly Asn Pro Ser Asn Asn Pro
                20                  25                  30

Thr Gly Ala Ala Tyr Asp Ser Ser Cys Thr Asn Leu Lys Leu Tyr Cys
                35                  40                  45

Gly Gly Asp Trp Gln Gly Leu Val Asn Lys Ile Asn Asp Asn Tyr Phe
50                  55                  60

Thr Asp Leu Gly Ile Thr Ala Leu Trp Ile Ser Gln Pro Val Glu Asn
65                  70                  75                  80

Ile Tyr Ser Leu Ile Asn Tyr Ser Gly Val Asn Asn Ser Ala Tyr His
                85                  90                  95

Gly Tyr Trp Ala Arg Asp Phe Lys Lys Thr Asn Pro Ala Phe Gly Thr
                100                 105                 110

Met Thr Asp Phe Gln Asn Leu Ile Asn Thr Ala His Ala Lys Gly Ile
                115                 120                 125

Lys Val Ile Ile Asp Phe Ala Pro Asn His Thr Ser Pro Ala Met Glu
130                 135                 140

Thr Asp Thr Ser Phe Ala Glu Asn Gly Lys Leu Tyr Asn Asn Gly Thr
145                 150                 155                 160

Leu Leu Gly Gly Tyr Thr Asn Asp Thr Asn Lys Phe Phe His His Asn
                165                 170                 175

Gly Gly Ser Asp Phe Ser Ser Leu Glu Asn Gly Ile Tyr Lys Asn Leu
                180                 185                 190

Tyr Asp Leu Ala Asp Leu Asn His Asn Ser Thr Ile Asp Thr Tyr
                195                 200                 205

Phe Lys Asp Ala Ile Lys Leu Trp Leu Asp Met Gly Ile Asp Gly Ile
210                 215                 220
```

-continued

Arg Val Asp Ala Val Lys His Met Pro Met Gly Trp Gln Lys Asn Trp
225                 230                 235                 240

Met Ser Ser Ile Tyr Gly Tyr Lys Pro Val Phe Thr Phe Gly Glu Trp
            245                 250                 255

Phe Leu Gly Ser Ser Ala Ser Asp Ala Asp Asn Thr Asn Phe Ala Asn
        260                 265                 270

Gln Ser Gly Met Ser Leu Leu Asp Phe Arg Phe Asn Asn Glu Val Arg
    275                 280                 285

Asn Val Phe Arg Asp Asn Thr Ser Thr Met Val Ala Leu Asp Ser Met
290                 295                 300

Ile Thr Ser Thr Ala Ala Asp Tyr Ala Gln Val Asn Asp Gln Val Thr
305                 310                 315                 320

Phe Ile Asp Asn His Asp Met Asp Arg Phe Lys Thr Ser Ala Val Asn
                325                 330                 335

Asn Arg Arg Leu Glu Gln Ala Leu Ala Phe Thr Leu Thr Ser Arg Gly
            340                 345                 350

Val Pro Ala Ile Tyr Tyr Gly Thr Glu Gln Tyr Leu Thr Gly Asn Gly
        355                 360                 365

Asp Pro Asp Asn Arg Ala Lys Met Pro Ser Phe Ser Lys Thr Thr Thr
    370                 375                 380

Ala Phe Asn Val Ile Ser Lys Leu Ala Pro Leu Arg Lys Thr Asn Pro
385                 390                 395                 400

Ala Ile Ala Tyr Gly Thr Thr Gln Gln Arg Trp Ile Asn Asn Asp Val
                405                 410                 415

Tyr Val Tyr Glu Arg Lys Phe Gly Asn Asn Val Ala Val Val Ala Val
            420                 425                 430

Asn Arg Asn Leu Ser Thr Pro Thr Ser Ile Ser Gly Leu Thr Thr Ser
        435                 440                 445

Leu Pro Ser Gly Thr Tyr Asn Asp Val Leu Ala Gly Ala Leu Ser Gly
    450                 455                 460

Asn Asn Ile Thr Ser Thr Gly Gly Asn Val Ala Asn Phe Thr Leu Ala
465                 470                 475                 480

Ala Gly Ala Thr Ala Val Trp Gln Tyr Thr Ala Asn Thr Thr Thr Pro
                485                 490                 495

Thr Ile Gly His Val Gly Pro Thr Met Gly Lys Ala Gly Asn Thr Val
            500                 505                 510

Thr Ile Asp Gly Arg Gly Phe Gly Thr Thr Lys Gly Thr Val Tyr Phe
        515                 520                 525

Gly Thr Thr Ala Val Thr Gly Ser Ala Ile Thr Ser Trp Glu Asp Thr
    530                 535                 540

Gln Ile Lys Val Thr Ile Pro Ala Val Ala Ala Gly Asn Tyr Ala Val
545                 550                 555                 560

Lys Val Ala Ala Gly Gly Val Asn Ser Asn Thr Tyr Asn Asn Phe Thr
                565                 570                 575

Ile Leu Ser Gly Asn Gln Val Ser Val Arg Phe Val Ile Asn Asn Ala
            580                 585                 590

Ser Thr Thr Leu Gly Gln Asn Leu Tyr Leu Thr Gly Asn Val Ala Glu
        595                 600                 605

Leu Gly Asn Trp Ser Thr Gly Pro Leu Ala Ile Gly Pro Ala Phe Asn
    610                 615                 620

Gln Val Ile Tyr Ser Tyr Pro Thr Trp Tyr Tyr Asp Val Ser Val Pro
625                 630                 635                 640

Ala Gly Thr Asn Leu Glu Phe Lys Phe Phe Lys Lys Asn Gly Ser Thr

```
                    645                 650                 655
Ile Thr Trp Glu Asn Gly Asn Asn His Thr Phe Thr Thr Pro Thr Ser
                660                 665                 670

Gly Thr Ala Thr Val Thr Val Asp Trp Gln Pro
            675                 680

<210> SEQ ID NO 3
<211> LENGTH: 682
<212> TYPE: PRT
<213> ORGANISM: Paenibacillus amylolyticus

<400> SEQUENCE: 3

Asp Thr Ala Val Thr Asn Lys Gln Asn Phe Ser Thr Asp Val Ile Tyr
1               5                   10                  15

Gln Ile Phe Thr Asp Arg Phe Leu Asp Gly Asn Pro Ser Asn Asn Pro
                20                  25                  30

Thr Gly Ala Ala Tyr Asp Ala Thr Cys Ser Asn Leu Lys Leu Tyr Cys
            35                  40                  45

Gly Gly Asp Trp Gln Gly Leu Ile Asn Lys Ile Asn Asp Asn Tyr Phe
        50                  55                  60

Ser Asp Leu Gly Val Thr Ala Leu Trp Ile Ser Gln Pro Val Glu Asn
65                  70                  75                  80

Ile Phe Ala Thr Ile Asn Tyr Gly Gly Val Ile Asn Thr Ala Tyr His
                85                  90                  95

Gly Tyr Trp Ala Arg Asp Phe Lys Lys Thr Asn Pro Tyr Phe Gly Thr
            100                 105                 110

Met Ala Asp Phe Gln Asn Leu Ile Thr Thr Ala His Ala Lys Gly Ile
        115                 120                 125

Lys Ile Val Ile Asp Phe Ala Pro Asn His Thr Ser Pro Ala Met Glu
130                 135                 140

Thr Asp Thr Ser Phe Ala Glu Asn Gly Lys Leu Tyr Asp Asn Gly Asn
145                 150                 155                 160

Leu Val Gly Gly Tyr Thr Asn Asp Thr Asn Gly Tyr Phe His His Asn
                165                 170                 175

Gly Gly Ser Asp Phe Ser Ser Leu Glu Asn Gly Ile Tyr Lys Asn Leu
            180                 185                 190

Tyr Asp Leu Ala Asp Leu Asn His Asn Asn Ser Thr Ile Asp Gln Tyr
        195                 200                 205

Phe Lys Asp Ala Ile Lys Leu Trp Leu Asp Met Gly Val Asp Gly Ile
210                 215                 220

Arg Val Asp Ala Val Lys His Met Pro Leu Gly Trp Gln Lys Ser Trp
225                 230                 235                 240

Met Ser Ser Ile Tyr Ala His Lys Pro Val Phe Thr Phe Gly Glu Trp
                245                 250                 255

Phe Leu Gly Ser Ala Ala Ser Asp Ala Asp Asn Thr Glu Phe Ala Asn
            260                 265                 270

Glu Ser Gly Met Ser Leu Leu Asp Phe Arg Phe Asn Ser Ala Val Arg
        275                 280                 285

Asp Val Phe Arg Asp Asn Thr Ser Asn Met Tyr Ala Leu Asp Ser Met
290                 295                 300

Ile Thr Gly Thr Ala Ala Asp Tyr Asn Gln Val Asn Asp Gln Val Thr
305                 310                 315                 320

Phe Ile Asp Asn His Asp Met Asp Arg Phe Lys Thr Ser Ala Val Asn
                325                 330                 335
```

```
Asn Arg Arg Leu Glu Gln Ala Leu Ala Phe Thr Leu Thr Ser Arg Gly
            340                 345                 350

Val Pro Ala Ile Tyr Tyr Gly Thr Glu Gln Tyr Leu Thr Gly Asn Gly
355                 360                 365

Asp Pro Asp Asn Arg Ala Lys Met Pro Ser Phe Ser Lys Thr Thr Thr
    370                 375                 380

Ala Phe Asn Val Ile Ser Lys Leu Ala Pro Leu Arg Lys Ser Asn Pro
385                 390                 395                 400

Ala Ile Ala Tyr Gly Ser Thr Gln Gln Arg Trp Ile Asn Asn Asp Val
                405                 410                 415

Tyr Val Tyr Glu Arg Lys Phe Gly Lys Ser Val Ala Val Ala Val
            420                 425                 430

Asn Arg Asn Leu Ser Thr Pro Ala Ser Ile Ala Asn Leu Ser Thr Ser
        435                 440                 445

Leu Pro Thr Gly Asn Tyr Thr Asp Val Leu Gly Gly Ala Leu Asn Gly
    450                 455                 460

Ser Asn Ile Thr Ser Thr Asn Gly Asn Val Ser Ser Phe Thr Leu Ala
465                 470                 475                 480

Ala Gly Ala Thr Ala Val Trp Gln Tyr Thr Thr Ser Glu Thr Pro
                485                 490                 495

Thr Ile Gly His Val Gly Pro Val Met Gly Lys Pro Gly Asn Val Val
                500                 505                 510

Thr Ile Ser Gly Arg Gly Phe Gly Ser Thr Lys Gly Thr Val Tyr Phe
            515                 520                 525

Gly Thr Thr Ala Val Thr Gly Ala Ala Ile Thr Ser Trp Glu Asp Thr
530                 535                 540

Gln Ile Lys Val Thr Ile Pro Ala Val Ala Ala Gly Asn Tyr Ala Val
545                 550                 555                 560

Lys Val Ala Ala Asn Gly Val Asn Ser Asn Ala Tyr Asn Asn Phe Thr
                565                 570                 575

Ile Leu Thr Gly Asp Gln Val Thr Val Arg Phe Val Ile Asn Asn Ala
            580                 585                 590

Ser Thr Thr Leu Gly Gln Asn Ile Tyr Leu Thr Gly Asn Val Ala Glu
        595                 600                 605

Leu Gly Asn Trp Ser Thr Gly Thr Thr Ala Ile Gly Pro Ala Phe Asn
    610                 615                 620

Gln Val Ile His Ala Tyr Pro Thr Trp Tyr Tyr Asp Val Ser Val Pro
625                 630                 635                 640

Ala Gly Lys Gln Leu Glu Phe Lys Phe Lys Lys Asn Gly Ala Thr
                645                 650                 655

Ile Thr Trp Glu Gly Gly Ser Asn His Thr Phe Thr Thr Pro Thr Ser
            660                 665                 670

Gly Thr Ala Thr Val Asn Val Asn Trp Gln
        675                 680

<210> SEQ ID NO 4
<211> LENGTH: 680
<212> TYPE: PRT
<213> ORGANISM: Geobacillus stearothermophilus

<400> SEQUENCE: 4

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30
```

```
Gly Ala Leu Phe Ser Ser Gly Cys Thr Asn Leu Arg Lys Tyr Cys Gly
            35                  40                  45

Gly Asp Trp Gln Gly Ile Ile Asn Lys Ile Asn Asp Gly Tyr Leu Thr
        50                  55                  60

Asp Met Gly Val Thr Ala Ile Trp Ile Ser Gln Pro Val Glu Asn Val
 65                  70                  75                  80

Phe Ser Val Met Asn Asp Ala Ser Gly Ser Ala Ser Tyr His Gly Tyr
                85                  90                  95

Trp Ala Arg Asp Phe Lys Lys Pro Asn Pro Phe Gly Thr Leu Ser
            100                 105                 110

Asp Phe Gln Arg Leu Val Asp Ala Ala His Ala Lys Gly Ile Lys Val
            115                 120                 125

Ile Ile Asp Phe Ala Pro Asn His Thr Ser Pro Ala Ser Glu Thr Asn
        130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
            195                 200                 205

Asp Ala Val Lys Met Trp Ile Asp Met Gly Ile Asp Gly Ile Arg Met
210                 215                 220

Asp Ala Val Lys His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
            245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
        275                 280                 285

Leu Arg Asn Asn Ser Asp Asn Trp Tyr Gly Phe Asn Gln Met Ile Gln
        290                 295                 300

Asp Thr Ala Ser Ala Tyr Asp Glu Val Leu Asp Gln Val Thr Phe Ile
305                 310                 315                 320

Asp Asn His Asp Met Asp Arg Phe Met Ile Asp Gly Gly Asp Pro Arg
            325                 330                 335

Lys Val Asp Met Ala Leu Ala Val Leu Leu Thr Ser Arg Gly Val Pro
            340                 345                 350

Asn Ile Tyr Tyr Gly Thr Glu Gln Tyr Met Thr Gly Asn Gly Asp Pro
        355                 360                 365

Asn Asn Arg Lys Met Met Ser Ser Phe Asn Lys Asn Thr Arg Ala Tyr
        370                 375                 380

Gln Val Ile Gln Lys Leu Ser Ser Leu Arg Arg Asn Asn Pro Ala Leu
385                 390                 395                 400

Ala Tyr Gly Asp Thr Glu Gln Arg Trp Ile Asn Gly Asp Val Tyr Val
            405                 410                 415

Tyr Glu Arg Gln Phe Gly Lys Asp Val Val Leu Val Ala Val Asn Arg
            420                 425                 430

Ser Ser Ser Asn Tyr Ser Ile Thr Gly Leu Phe Thr Ala Leu Pro
            435                 440                 445
```

```
Ala Gly Thr Tyr Thr Asp Gln Leu Gly Gly Leu Leu Asp Gly Asn Thr
    450                 455                 460

Ile Gln Val Gly Ser Asn Gly Ser Val Asn Ala Phe Asp Leu Gly Pro
465                 470                 475                 480

Gly Glu Val Gly Val Trp Ala Tyr Ser Ala Thr Glu Ser Thr Pro Ile
                485                 490                 495

Ile Gly His Val Gly Pro Met Met Gly Gln Val Gly His Gln Val Thr
                500                 505                 510

Ile Asp Gly Glu Gly Phe Gly Thr Asn Thr Gly Thr Val Lys Phe Gly
                515                 520                 525

Thr Thr Ala Ala Asn Val Val Ser Trp Ser Asn Gln Ile Val Val
530                 535                 540

Ala Val Pro Asn Val Ser Pro Gly Lys Tyr Asn Ile Thr Val Gln Ser
545                 550                 555                 560

Ser Ser Gly Gln Thr Ser Ala Ala Tyr Asp Asn Phe Glu Val Leu Thr
                565                 570                 575

Asn Asp Gln Val Ser Val Arg Phe Val Val Asn Ala Thr Thr Asn
                580                 585                 590

Leu Gly Gln Asn Ile Tyr Ile Val Gly Asn Val Tyr Glu Leu Gly Asn
                595                 600                 605

Trp Asp Thr Ser Lys Ala Ile Gly Pro Met Phe Asn Gln Val Val Tyr
610                 615                 620

Ser Tyr Pro Thr Trp Tyr Ile Asp Val Ser Val Pro Glu Gly Lys Thr
625                 630                 635                 640

Ile Glu Phe Lys Phe Ile Lys Lys Asp Ser Gln Gly Asn Val Thr Trp
                645                 650                 655

Glu Ser Gly Ser Asn His Val Tyr Thr Thr Pro Thr Asn Thr Thr Gly
                660                 665                 670

Lys Ile Ile Val Asp Trp Gln Asn
                675                 680

<210> SEQ ID NO 5
<211> LENGTH: 686
<212> TYPE: PRT
<213> ORGANISM: Bacillus macerans

<400> SEQUENCE: 5

Ser Pro Asp Thr Ser Val Asn Asn Lys Leu Asn Phe Ser Thr Asp Thr
1               5                   10                  15

Val Tyr Gln Ile Val Thr Asp Arg Phe Val Asp Gly Asn Ser Ala Asn
                20                  25                  30

His Pro Thr Gly Ala Ala Phe Ser Ser Asp His Ser Asn Leu Lys Leu
            35                  40                  45

Tyr Phe Gly Gly Asp Trp Gln Gly Ile Thr Asn Lys Ile Asn Asp Gly
        50                  55                  60

Tyr Leu Thr Gly Met Gly Ile Thr Ala Leu Trp Ile Ser Gln Pro Val
65                  70                  75                  80

Glu Asn Ile Thr Ala Val Ile Lys Tyr Ser Gly Val Asn Asn Thr Ala
                85                  90                  95

Tyr His Gly Tyr Trp Pro Arg Asp Phe Lys Lys Thr Asn Ala Ala Phe
            100                 105                 110

Gly Ser Phe Thr Asp Phe Ser Asn Leu Ile Ala Ala His Ser His
        115                 120                 125

Asn Ile Lys Val Val Met Asp Phe Ala Pro Asn His Thr Asn Pro Ala
130                 135                 140
```

-continued

```
Ser Ser Thr Asp Pro Ser Phe Ala Glu Asn Gly Ala Leu Tyr Asn Asn
145                 150                 155                 160

Gly Thr Leu Leu Gly Lys Tyr Ser Asn Asp Thr Ala Gly Leu Phe His
                165                 170                 175

His Asn Gly Gly Thr Asp Phe Ser Thr Thr Glu Ser Gly Ile Tyr Lys
            180                 185                 190

Asn Leu Tyr Asp Leu Ala Asp Ile Asn Gln Asn Asn Asn Thr Ile Asp
        195                 200                 205

Ser Tyr Leu Lys Glu Ser Ile Gln Leu Trp Leu Asn Leu Gly Val Asp
    210                 215                 220

Gly Ile Arg Phe Asp Ala Val Lys His Met Pro Gln Gly Trp Gln Lys
225                 230                 235                 240

Ser Tyr Val Ser Ser Ile Tyr Ser Ser Ala Asn Pro Val Phe Thr Phe
                245                 250                 255

Gly Glu Trp Phe Leu Gly Pro Asp Glu Met Thr Gln Asp Asn Ile Asn
            260                 265                 270

Phe Ala Asn Gln Ser Gly Met His Leu Leu Asp Phe Ala Phe Ala Gln
        275                 280                 285

Glu Ile Arg Glu Val Phe Arg Asp Lys Ser Gly Thr Met Thr Asp Leu
    290                 295                 300

Asn Ser Val Ile Ser Ser Thr Gly Ser Ser Tyr Asn Tyr Ile Asn Asn
305                 310                 315                 320

Met Val Thr Phe Ile Asp Asn His Asp Met Asp Arg Phe Gln Gln Ala
                325                 330                 335

Gly Ala Ser Thr Arg Pro Thr Glu Gln Ala Leu Ala Val Thr Leu Thr
            340                 345                 350

Ser Arg Gly Val Pro Ala Ile Tyr Tyr Gly Thr Glu Gln Tyr Met Thr
        355                 360                 365

Gly Asn Gly Asp Pro Asn Asn Arg Gly Met Met Thr Gly Phe Asp Thr
    370                 375                 380

Asn Lys Thr Ala Tyr Lys Val Ile Lys Ala Leu Ala Pro Leu Arg Lys
385                 390                 395                 400

Ser Asn Pro Ala Leu Ala Tyr Gly Ser Thr Thr Gln Arg Trp Val Asn
                405                 410                 415

Ser Asp Val Tyr Val Tyr Glu Arg Lys Phe Gly Ser Asn Val Ala Leu
            420                 425                 430

Val Ala Val Asn Arg Ser Ser Thr Thr Ala Tyr Pro Ile Ser Gly Ala
        435                 440                 445

Leu Thr Ala Leu Pro Asn Gly Thr Tyr Thr Asp Val Leu Gly Gly Leu
    450                 455                 460

Leu Asn Gly Asn Ser Ile Thr Val Asn Gly Gly Thr Val Ser Asn Phe
465                 470                 475                 480

Thr Leu Ala Ala Gly Gly Thr Ala Val Trp Gln Tyr Thr Thr Thr Glu
                485                 490                 495

Ser Ser Pro Ile Ile Gly Asn Val Gly Pro Thr Met Gly Lys Pro Gly
            500                 505                 510

Asn Thr Ile Thr Ile Asp Gly Arg Gly Phe Gly Thr Thr Lys Asn Lys
        515                 520                 525

Val Thr Phe Gly Thr Thr Ala Val Thr Gly Ala Asn Ile Val Ser Trp
    530                 535                 540

Glu Asp Thr Glu Ile Lys Val Lys Val Pro Asn Val Ala Ala Gly Asn
545                 550                 555                 560
```

```
Thr Ala Val Thr Val Thr Asn Ala Ala Gly Thr Ser Ala Ala Phe
                565                 570                 575

Asn Asn Phe Asn Val Leu Thr Ala Asp Gln Val Thr Val Arg Phe Lys
            580                 585                 590

Val Asn Asn Ala Thr Thr Ala Leu Gly Gln Asn Val Tyr Leu Thr Gly
        595                 600                 605

Asn Val Ala Glu Leu Gly Asn Trp Thr Ala Asn Ala Ile Gly Pro
    610                 615                 620

Met Tyr Asn Gln Val Glu Ala Ser Tyr Pro Thr Trp Tyr Phe Asp Val
625                 630                 635                 640

Ser Val Pro Ala Asn Thr Ala Leu Gln Phe Lys Phe Ile Lys Val Asn
                645                 650                 655

Gly Ser Thr Val Thr Trp Glu Gly Gly Asn Asn His Thr Phe Thr Ser
                660                 665                 670

Pro Ser Ser Gly Val Ala Thr Val Thr Val Asp Trp Gln Asn
                675                 680                 685

<210> SEQ ID NO 6
<211> LENGTH: 681
<212> TYPE: PRT
<213> ORGANISM: Thermoanaerobacter thermosulfurigenes

<400> SEQUENCE: 6

Ala Pro Asp Thr Ser Val Ser Asn Val Val Tyr Ser Thr Asp Val
1               5                   10                  15

Ile Tyr Gln Ile Val Thr Asp Arg Phe Leu Asp Gly Asn Pro Ser Asn
            20                  25                  30

Asn Pro Thr Gly Asp Leu Tyr Asp Pro Thr His Thr Ser Leu Lys Lys
        35                  40                  45

Tyr Phe Gly Gly Asp Trp Gln Gly Ile Ile Asn Lys Ile Asn Asp Gly
50                  55                  60

Tyr Leu Thr Gly Met Gly Ile Thr Ala Ile Trp Ile Ser Gln Pro Val
65                  70                  75                  80

Glu Asn Ile Tyr Ala Val Leu Pro Asp Ser Thr Phe Gly Gly Ser Thr
            85                  90                  95

Ser Tyr His Gly Tyr Trp Ala Arg Asp Phe Lys Lys Pro Asn Pro Phe
        100                 105                 110

Phe Gly Ser Phe Thr Asp Phe Gln Asn Leu Ile Ala Thr Ala His Ala
    115                 120                 125

His Asn Ile Lys Val Ile Ile Asp Phe Ala Pro Asn His Thr Ser Pro
130                 135                 140

Ala Ser Glu Thr Asp Pro Thr Tyr Gly Glu Asn Gly Arg Leu Tyr Asp
145                 150                 155                 160

Asn Gly Val Leu Leu Gly Gly Tyr Thr Asn Asp Thr Asn Gly Tyr Phe
                165                 170                 175

His His Tyr Gly Gly Thr Asn Phe Ser Ser Tyr Glu Asp Gly Ile Tyr
            180                 185                 190

Arg Asn Leu Phe Asp Leu Ala Asp Leu Asp Gln Gln Asn Ser Thr Ile
        195                 200                 205

Asp Ser Tyr Leu Lys Ala Ala Ile Lys Leu Trp Leu Asp Met Gly Ile
    210                 215                 220

Asp Gly Ile Arg Met Asp Ala Val Lys His Met Ala Phe Gly Trp Gln
225                 230                 235                 240

Lys Asn Phe Met Asp Ser Ile Leu Ser Tyr Arg Pro Val Phe Thr Phe
                245                 250                 255
```

-continued

Gly Glu Trp Tyr Leu Gly Thr Asn Glu Val Asp Pro Asn Asn Thr Tyr
            260                 265                 270

Phe Ala Asn Glu Ser Gly Met Ser Leu Leu Asp Phe Arg Phe Ala Gln
            275                 280                 285

Lys Val Arg Gln Val Phe Arg Asp Asn Thr Asp Thr Met Tyr Gly Leu
290                 295                 300

Asp Ser Met Ile Gln Ser Thr Ala Ala Asp Tyr Asn Phe Ile Asn Asp
305                 310                 315                 320

Met Val Thr Phe Ile Asp Asn His Asp Met Asp Arg Phe Tyr Thr Gly
                    325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
            355                 360                 365

Asn Gly Asp Pro Tyr Asn Arg Ala Met Met Thr Ser Phe Asp Thr Thr
            370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Gln Lys Gln Arg Trp Ile Asn Asn
                    405                 410                 415

Asp Val Tyr Ile Tyr Glu Arg Gln Phe Gly Asn Asn Val Ala Leu Val
            420                 425                 430

Ala Ile Asn Arg Asn Leu Ser Thr Ser Tyr Tyr Ile Thr Gly Leu Tyr
            435                 440                 445

Thr Ala Leu Pro Ala Gly Thr Tyr Ser Asp Met Leu Gly Gly Leu Leu
450                 455                 460

Asn Gly Ser Ser Ile Thr Val Ser Ser Asn Gly Ser Val Thr Pro Phe
465                 470                 475                 480

Thr Leu Ala Pro Gly Glu Val Ala Val Trp Gln Tyr Val Ser Thr Thr
                    485                 490                 495

Asn Pro Pro Leu Ile Gly His Val Gly Pro Thr Met Thr Lys Ala Gly
            500                 505                 510

Gln Thr Ile Thr Ile Asp Gly Arg Gly Phe Gly Thr Thr Ala Gly Gln
            515                 520                 525

Val Leu Phe Gly Thr Thr Pro Ala Thr Ile Val Ser Trp Glu Asp Thr
            530                 535                 540

Glu Val Lys Val Lys Val Pro Ala Leu Thr Pro Gly Lys Tyr Asn Ile
545                 550                 555                 560

Thr Leu Lys Thr Ala Ser Gly Val Thr Ser Asn Ser Tyr Asn Asn Ile
                    565                 570                 575

Asn Val Leu Thr Gly Asn Gln Val Cys Val Arg Phe Val Val Asn Asn
            580                 585                 590

Ala Thr Thr Val Trp Gly Glu Asn Val Tyr Leu Thr Gly Asn Val Ala
            595                 600                 605

Glu Leu Gly Asn Trp Asp Thr Ser Lys Ala Ile Gly Pro Met Phe Asn
            610                 615                 620

Gln Val Val Tyr Gln Tyr Pro Thr Trp Tyr Tyr Asp Val Ser Val Pro
625                 630                 635                 640

Ala Gly Thr Thr Ile Glu Phe Ile Lys Lys Asn Gly Ser Thr Val Thr
                    645                 650                 655

Trp Glu Gly Gly Tyr Asn His Val Tyr Thr Thr Pro Thr Ser Gly Thr
            660                 665                 670

```
Ala Thr Val Ile Val Asp Trp Gln Pro
            675                 680

<210> SEQ ID NO 7
<211> LENGTH: 2154
<212> TYPE: DNA
<213> ORGANISM: Paenibacillus illinoisensis
<220> FEATURE:
<221> NAME/KEY: CDS
<222> LOCATION: (1)..(2154)

<400> SEQUENCE: 7 atg ttt caa atg gcc aaa cgc gtt ctc ctc agt acc acg cta acg ttc      48
Met Phe Gln Met Ala Lys Arg Val Leu Leu Ser Thr Thr Leu Thr Phe
1               5                   10                  15 agc ctg ctt gcc ggc agt gca ttg cct ttc ctg cct gcc tcc gcg att      96
Ser Leu Leu Ala Gly Ser Ala Leu Pro Phe Leu Pro Ala Ser Ala Ile
                20                  25                  30 tat gcc gat gcg gat acg gct gtc acc aac aag caa aat ttc agt acc     144
Tyr Ala Asp Ala Asp Thr Ala Val Thr Asn Lys Gln Asn Phe Ser Thr
            35                  40                  45 gat gtc atc tat caa gtt ttt acg gac cgg ttt ctg gac ggt aac cca     192
Asp Val Ile Tyr Gln Val Phe Thr Asp Arg Phe Leu Asp Gly Asn Pro
        50                  55                  60 tcc aac aac ccc act gga gct gct ttt gat ggc aca tgc agc aac ctg     240
Ser Asn Asn Pro Thr Gly Ala Ala Phe Asp Gly Thr Cys Ser Asn Leu
65                  70                  75                  80 aaa ctg tac tgc ggc ggc gac tgg cag ggg ctg att aac aaa atc aat     288
Lys Leu Tyr Cys Gly Gly Asp Trp Gln Gly Leu Ile Asn Lys Ile Asn
                85                  90                  95 gac aac tat ttc agt gac ctg ggt gtc aca gcc ctc tgg atc tcc cag     336
Asp Asn Tyr Phe Ser Asp Leu Gly Val Thr Ala Leu Trp Ile Ser Gln
            100                 105                 110 cct gtc gaa aat att ttc gct acc atc aac tac agc ggt gta acc aac     384
Pro Val Glu Asn Ile Phe Ala Thr Ile Asn Tyr Ser Gly Val Thr Asn
        115                 120                 125 act gct tat cac ggc tat tgg gca cgg gat ttc aag aag acc aat cca     432
Thr Ala Tyr His Gly Tyr Trp Ala Arg Asp Phe Lys Lys Thr Asn Pro
    130                 135                 140 tat ttc gga acc atg acc gat ttt cag aat ctg gtg acc tcc gcc cat     480
Tyr Phe Gly Thr Met Thr Asp Phe Gln Asn Leu Val Thr Ser Ala His
145                 150                 155                 160 gct aaa ggc atc aaa atc att att gat ttc gcg cca aac cat acg ttc     528
Ala Lys Gly Ile Lys Ile Ile Ile Asp Phe Ala Pro Asn His Thr Phe
                165                 170                 175 cct gcc atg gaa acc gat acc tcc ttc gct gaa aac ggc aaa ctg tac     576
Pro Ala Met Glu Thr Asp Thr Ser Phe Ala Glu Asn Gly Lys Leu Tyr
            180                 185                 190 gat aac ggc agc ctg gtg ggc ggg tac acc aat gat acg aac gga tat     624
Asp Asn Gly Ser Leu Val Gly Gly Tyr Thr Asn Asp Thr Asn Gly Tyr
        195                 200                 205 ttt cac cac aat ggc ggc tcc gat ttc tcc act ctt gag aat ggc att     672
Phe His His Asn Gly Gly Ser Asp Phe Ser Thr Leu Glu Asn Gly Ile
    210                 215                 220 tac aaa aac ctc tac gat ctg gcc gat ctg aat cac aat aac agc acg     720
Tyr Lys Asn Leu Tyr Asp Leu Ala Asp Leu Asn His Asn Asn Ser Thr
225                 230                 235                 240 atc gat aca tat ttc aaa gac gcc atc aag ctg tgg ctg gat atg ggc     768
Ile Asp Thr Tyr Phe Lys Asp Ala Ile Lys Leu Trp Leu Asp Met Gly
                245                 250                 255 gtg gac ggc atc cgt gtc gat gcg gtc aag cac atg cca cag gga tgg     816
```

-continued

```
                    Val Asp Gly Ile Arg Val Asp Ala Val Lys His Met Pro Gln Gly Trp
                                    260                 265                 270 cag aag aac tgg atg tca tcc atc tat gca cac aag ccg gta ttt acc        864
Gln Lys Asn Trp Met Ser Ser Ile Tyr Ala His Lys Pro Val Phe Thr
            275                 280                 285 ttc ggc gaa tgg ttc ctg gga tct gct gca tcc gat gcg gat aac aca        912
Phe Gly Glu Trp Phe Leu Gly Ser Ala Ala Ser Asp Ala Asp Asn Thr
290                 295                 300 gat ttt gcc aat gaa tcc ggt atg agt ttg ctt gat ttt cgt ttc aat        960
Asp Phe Ala Asn Glu Ser Gly Met Ser Leu Leu Asp Phe Arg Phe Asn
305                 310                 315                 320 tcg gct gtc cgc aac gtg ttc cgg gat aac aca tcc aac atg tac gcg       1008
Ser Ala Val Arg Asn Val Phe Arg Asp Asn Thr Ser Asn Met Tyr Ala
            325                 330                 335 ctg gat tcc atg ctt acg gct acg gca gca gat tac aat caa gtg aat       1056
Leu Asp Ser Met Leu Thr Ala Thr Ala Ala Asp Tyr Asn Gln Val Asn
                340                 345                 350 gac caa gtc act ttc att gac aac cat gat atg gac cgt ttc aaa aca       1104
Asp Gln Val Thr Phe Ile Asp Asn His Asp Met Asp Arg Phe Lys Thr
            355                 360                 365 agt gcg gtg aac aac cgc cgt ctg gaa cag gct ctg gcc ttc acg ctg       1152
Ser Ala Val Asn Asn Arg Arg Leu Glu Gln Ala Leu Ala Phe Thr Leu
370                 375                 380 acc tca cgc ggc gta cct gcc atc tat tat ggt acc gag cag tat ctg       1200
Thr Ser Arg Gly Val Pro Ala Ile Tyr Tyr Gly Thr Glu Gln Tyr Leu
385                 390                 395                 400 acc ggg aat ggt gac ccg gat aac cgg ggc aaa atg cct tcc ttc tcc       1248
Thr Gly Asn Gly Asp Pro Asp Asn Arg Gly Lys Met Pro Ser Phe Ser
            405                 410                 415 aaa tcg acc aca gcg ttc agc gtg atc agc aag ctg gct cct ctg cgc       1296
Lys Ser Thr Thr Ala Phe Ser Val Ile Ser Lys Leu Ala Pro Leu Arg
                420                 425                 430 aaa tcc aac ccg gcg att gcc tac ggt tcc aca cag cag cgc tgg atc       1344
Lys Ser Asn Pro Ala Ile Ala Tyr Gly Ser Thr Gln Gln Arg Trp Ile
            435                 440                 445 aac aat gat gta tat atc tat gag cgc aag ttt ggc aaa agc gtt gcc       1392
Asn Asn Asp Val Tyr Ile Tyr Glu Arg Lys Phe Gly Lys Ser Val Ala
450                 455                 460 gtt gtt gcc gtt aac cgc aat ctc acg acg cca acc agt atc acg aac       1440
Val Val Ala Val Asn Arg Asn Leu Thr Thr Pro Thr Ser Ile Thr Asn
465                 470                 475                 480 ctg aat acg tcc ctt cca tca gga aca tac acc gat gtg ctg ggc ggc       1488
Leu Asn Thr Ser Leu Pro Ser Gly Thr Tyr Thr Asp Val Leu Gly Gly
            485                 490                 495 gtg ctg aac gga aac aac att act tca agt gga ggc aac att tct tcc       1536
Val Leu Asn Gly Asn Asn Ile Thr Ser Ser Gly Gly Asn Ile Ser Ser
                500                 505                 510 ttc acg ctc gca gca gga gct acc gct gtg tgg cag tat acg gca agt       1584
Phe Thr Leu Ala Ala Gly Ala Thr Ala Val Trp Gln Tyr Thr Ala Ser
            515                 520                 525 gaa acg acg cca acc atc ggt cac gtt ggc cct gta atg ggt aaa cct       1632
Glu Thr Thr Pro Thr Ile Gly His Val Gly Pro Val Met Gly Lys Pro
530                 535                 540 ggt aac gtc gtt acc atc gac gga cgg ggg ttc ggc tcc acc aaa ggt       1680
Gly Asn Val Val Thr Ile Asp Gly Arg Gly Phe Gly Ser Thr Lys Gly
545                 550                 555                 560 acc gtc tac ttc ggt aca aca gcc gtt acg ggc tct gcc atc act tca       1728
Thr Val Tyr Phe Gly Thr Thr Ala Val Thr Gly Ser Ala Ile Thr Ser
            565                 570                 575
```

```
tgg gaa gac act cag atc aaa gtc acc att cca cca gta gca ggc ggt    1776
Trp Glu Asp Thr Gln Ile Lys Val Thr Ile Pro Pro Val Ala Gly Gly
        580                 585                 590 gac tat gca gtg aaa gtc gct gcc aat ggt gtg aac agc aat gcc tat    1824
Asp Tyr Ala Val Lys Val Ala Ala Asn Gly Val Asn Ser Asn Ala Tyr
            595                 600                 605 aac gat ttc acg atc cta agc ggc gat cag gtc tcg gtt cgg ttc gtc    1872
Asn Asp Phe Thr Ile Leu Ser Gly Asp Gln Val Ser Val Arg Phe Val
610                 615                 620 atc aat aat gcc aca act gca ctg ggt gaa aac atc tac ctg acg ggc    1920
Ile Asn Asn Ala Thr Thr Ala Leu Gly Glu Asn Ile Tyr Leu Thr Gly
625                 630                 635                 640 aac gtg tcc gaa ctg ggg aac tgg acc aca ggt gcg gct tcc att gga    1968
Asn Val Ser Glu Leu Gly Asn Trp Thr Thr Gly Ala Ala Ser Ile Gly
            645                 650                 655 ccg gct ttc aat cag gtc atc cac gcc tac ccg act tgg tat tat gac    2016
Pro Ala Phe Asn Gln Val Ile His Ala Tyr Pro Thr Trp Tyr Tyr Asp
            660                 665                 670 gta agt gtt cca gcc ggg aaa cag ctg gaa ttc aag ttc ttc aag aaa    2064
Val Ser Val Pro Ala Gly Lys Gln Leu Glu Phe Lys Phe Phe Lys Lys
        675                 680                 685 aac ggg gct acc att acg tgg gag ggt gga tcc aat cac acc ttt aca    2112
Asn Gly Ala Thr Ile Thr Trp Glu Gly Gly Ser Asn His Thr Phe Thr
690                 695                 700 aca ccg acc agc ggt act gcc act gta aca gta aac tgg caa           2154
Thr Pro Thr Ser Gly Thr Ala Thr Val Thr Val Asn Trp Gln
705                 710                 715

<210> SEQ ID NO 8
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense primer for PCR
<220> FEATURE:

<400> SEQUENCE: 8
ttcaccacaa tggccgctcc gatttctcca                                     30

<210> SEQ ID NO 9
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: antisense primer for PCR

<400> SEQUENCE: 9
tggagaaatc ggagcggcca ttgtggtgaa                                     30

<210> SEQ ID NO 10
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense primer for PCR

<400> SEQUENCE: 10
```

```
cttccatcag gaacacacac cgatgtgctg                                        30
```

<210> SEQ ID NO 11
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: antisense primer for PCR

<400> SEQUENCE: 11

```
cagcacatcg gtgtgtgttc ctgatggaag                                        30
```

<210> SEQ ID NO 12
<211> LENGTH: 682
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mutated CGTase(G178R)

<400> SEQUENCE: 12

```
Asp Thr Ala Val Thr Asn Lys Gln Asn Phe Ser Thr Asp Val Ile Tyr
1               5                   10                  15

Gln Val Phe Thr Asp Arg Phe Leu Asp Gly Asn Pro Ser Asn Asn Pro
            20                  25                  30

Thr Gly Ala Ala Phe Asp Gly Thr Cys Ser Asn Leu Lys Leu Tyr Cys
        35                  40                  45

Gly Gly Asp Trp Gln Gly Leu Ile Asn Lys Ile Asn Asp Asn Tyr Phe
    50                  55                  60

Ser Asp Leu Gly Val Thr Ala Leu Trp Ile Ser Gln Pro Val Glu Asn
65                  70                  75                  80

Ile Phe Ala Thr Ile Asn Tyr Ser Gly Val Thr Asn Thr Ala Tyr His
                85                  90                  95

Gly Tyr Trp Ala Arg Asp Phe Lys Lys Thr Asn Pro Tyr Phe Gly Thr
            100                 105                 110

Met Thr Asp Phe Gln Asn Leu Val Thr Ser Ala His Ala Lys Gly Ile
        115                 120                 125

Lys Ile Ile Ile Asp Phe Ala Pro Asn His Thr Phe Pro Ala Met Glu
    130                 135                 140

Thr Asp Thr Ser Phe Ala Glu Asn Gly Lys Leu Tyr Asp Asn Gly Ser
145                 150                 155                 160

Leu Val Gly Gly Tyr Thr Asn Asp Thr Asn Gly Tyr Phe His His Asn
                165                 170                 175

Gly Arg Ser Asp Phe Ser Thr Leu Glu Asn Gly Ile Tyr Lys Asn Leu
            180                 185                 190

Tyr Asp Leu Ala Asp Leu Asn His Asn Asn Ser Thr Ile Asp Thr Tyr
        195                 200                 205

Phe Lys Asp Ala Ile Lys Leu Trp Leu Asp Met Gly Val Asp Gly Ile
    210                 215                 220

Arg Val Asp Ala Val Lys His Met Pro Gln Gly Trp Gln Lys Asn Trp
225                 230                 235                 240

Met Ser Ser Ile Tyr Ala His Lys Pro Val Phe Thr Phe Gly Glu Trp
                245                 250                 255
```

```
Phe Leu Gly Ser Ala Ala Ser Asp Ala Asp Asn Thr Asp Phe Ala Asn
            260                 265                 270

Glu Ser Gly Met Ser Leu Leu Asp Phe Arg Phe Asn Ser Ala Val Arg
            275                 280                 285

Asn Val Phe Arg Asp Asn Thr Ser Asn Met Tyr Ala Leu Asp Ser Met
290                 295                 300

Leu Thr Ala Thr Ala Ala Asp Tyr Asn Gln Val Asn Asp Gln Val Thr
305                 310                 315                 320

Phe Ile Asp Asn His Asp Met Asp Arg Phe Lys Thr Ser Ala Val Asn
                325                 330                 335

Asn Arg Arg Leu Glu Gln Ala Leu Ala Phe Thr Leu Thr Ser Arg Gly
            340                 345                 350

Val Pro Ala Ile Tyr Tyr Gly Thr Glu Gln Tyr Leu Thr Gly Asn Gly
            355                 360                 365

Asp Pro Asp Asn Arg Gly Lys Met Pro Ser Phe Ser Lys Ser Thr Thr
            370                 375                 380

Ala Phe Ser Val Ile Ser Lys Leu Ala Pro Leu Arg Lys Ser Asn Pro
385                 390                 395                 400

Ala Ile Ala Tyr Gly Ser Thr Gln Gln Arg Trp Ile Asn Asn Asp Val
            405                 410                 415

Tyr Ile Tyr Glu Arg Lys Phe Gly Lys Ser Val Ala Val Val Ala Val
            420                 425                 430

Asn Arg Asn Leu Thr Thr Pro Thr Ser Ile Thr Asn Leu Asn Thr Ser
            435                 440                 445

Leu Pro Ser Gly Thr Tyr Thr Asp Val Leu Gly Gly Val Leu Asn Gly
450                 455                 460

Asn Asn Ile Thr Ser Ser Gly Gly Asn Ile Ser Ser Phe Thr Leu Ala
465                 470                 475                 480

Ala Gly Ala Thr Ala Val Trp Gln Tyr Thr Ala Ser Glu Thr Thr Pro
            485                 490                 495

Thr Ile Gly His Val Gly Pro Val Met Gly Lys Pro Gly Asn Val Val
            500                 505                 510

Thr Ile Asp Gly Arg Gly Phe Gly Ser Thr Lys Gly Thr Val Tyr Phe
            515                 520                 525

Gly Thr Thr Ala Val Thr Gly Ser Ala Ile Thr Ser Trp Glu Asp Thr
530                 535                 540

Gln Ile Lys Val Thr Ile Pro Pro Val Ala Gly Gly Asp Tyr Ala Val
545                 550                 555                 560

Lys Val Ala Ala Asn Gly Val Asn Ser Asn Ala Tyr Asn Asp Phe Thr
                565                 570                 575

Ile Leu Ser Gly Asp Gln Val Ser Val Arg Phe Val Ile Asn Asn Ala
            580                 585                 590

Thr Thr Ala Leu Gly Glu Asn Ile Tyr Leu Thr Gly Asn Val Ser Glu
            595                 600                 605

Leu Gly Asn Trp Thr Thr Gly Ala Ala Ser Ile Gly Pro Ala Phe Asn
            610                 615                 620

Gln Val Ile His Ala Tyr Pro Thr Trp Tyr Tyr Asp Val Ser Val Pro
625                 630                 635                 640

Ala Gly Lys Gln Leu Glu Phe Lys Phe Lys Lys Asn Gly Ala Thr
            645                 650                 655

Ile Thr Trp Glu Gly Gly Ser Asn His Thr Phe Thr Thr Pro Thr Ser
            660                 665                 670

Gly Thr Ala Thr Val Thr Val Asn Trp Gln
```

<210> SEQ ID NO 13
<211> LENGTH: 682
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mutated CGTase(Y454H)

<400> SEQUENCE: 13

Asp Thr Ala Val Thr Asn Lys Gln Asn Phe Ser Thr Asp Val Ile Tyr
1               5                   10                  15

Gln Val Phe Thr Asp Arg Phe Leu Asp Gly Asn Pro Ser Asn Asn Pro
            20                  25                  30

Thr Gly Ala Ala Phe Asp Gly Thr Cys Ser Asn Leu Lys Leu Tyr Cys
        35                  40                  45

Gly Gly Asp Trp Gln Gly Leu Ile Asn Lys Ile Asn Asp Asn Tyr Phe
    50                  55                  60

Ser Asp Leu Gly Val Thr Ala Leu Trp Ile Ser Gln Pro Val Glu Asn
65                  70                  75                  80

Ile Phe Ala Thr Ile Asn Tyr Ser Gly Val Thr Asn Thr Ala Tyr His
                85                  90                  95

Gly Tyr Trp Ala Arg Asp Phe Lys Lys Thr Asn Pro Tyr Phe Gly Thr
            100                 105                 110

Met Thr Asp Phe Gln Asn Leu Val Thr Ser Ala His Ala Lys Gly Ile
        115                 120                 125

Lys Ile Ile Ile Asp Phe Ala Pro Asn His Thr Phe Pro Ala Met Glu
    130                 135                 140

Thr Asp Thr Ser Phe Ala Glu Asn Gly Lys Leu Tyr Asp Asn Gly Ser
145                 150                 155                 160

Leu Val Gly Gly Tyr Thr Asn Asp Thr Asn Gly Tyr Phe His His Asn
                165                 170                 175

Gly Gly Ser Asp Phe Ser Thr Leu Glu Asn Gly Ile Tyr Lys Asn Leu
            180                 185                 190

Tyr Asp Leu Ala Asp Leu Asn His Asn Asn Ser Thr Ile Asp Thr Tyr
        195                 200                 205

Phe Lys Asp Ala Ile Lys Leu Trp Leu Asp Met Gly Val Asp Gly Ile
    210                 215                 220

Arg Val Asp Ala Val Lys His Met Pro Gln Gly Trp Gln Lys Asn Trp
225                 230                 235                 240

Met Ser Ser Ile Tyr Ala His Lys Pro Val Phe Thr Phe Gly Glu Trp
                245                 250                 255

Phe Leu Gly Ser Ala Ala Ser Asp Ala Asp Asn Thr Asp Phe Ala Asn
            260                 265                 270

Glu Ser Gly Met Ser Leu Leu Asp Phe Arg Phe Asn Ser Ala Val Arg
        275                 280                 285

Asn Val Phe Arg Asp Asn Thr Ser Asn Met Tyr Ala Leu Asp Ser Met
    290                 295                 300

Leu Thr Ala Thr Ala Ala Asp Tyr Asn Gln Val Asn Asp Gln Val Thr
305                 310                 315                 320

Phe Ile Asp Asn His Asp Met Asp Arg Phe Lys Thr Ser Ala Val Asn
                325                 330                 335

Asn Arg Arg Leu Glu Gln Ala Leu Ala Phe Thr Leu Thr Ser Arg Gly

```
                    340                 345                 350
Val Pro Ala Ile Tyr Tyr Gly Thr Glu Gln Tyr Leu Thr Gly Asn Gly
                355                 360                 365

Asp Pro Asp Asn Arg Gly Lys Met Pro Ser Phe Ser Lys Ser Thr Thr
370                 375                 380

Ala Phe Ser Val Ile Ser Lys Leu Ala Pro Leu Arg Lys Ser Asn Pro
385                 390                 395                 400

Ala Ile Ala Tyr Gly Ser Thr Gln Gln Arg Trp Ile Asn Asn Asp Val
                405                 410                 415

Tyr Ile Tyr Glu Arg Lys Phe Gly Lys Ser Val Ala Val Ala Val
                420                 425                 430

Asn Arg Asn Leu Thr Thr Pro Thr Ser Ile Thr Asn Leu Asn Thr Ser
                435                 440                 445

Leu Pro Ser Gly Thr His Thr Asp Val Leu Gly Val Leu Asn Gly
                450                 455                 460

Asn Asn Ile Thr Ser Ser Gly Gly Asn Ile Ser Ser Phe Thr Leu Ala
465                 470                 475                 480

Ala Gly Ala Thr Ala Val Trp Gln Tyr Thr Ala Ser Glu Thr Thr Pro
                485                 490                 495

Thr Ile Gly His Val Gly Pro Val Met Gly Lys Pro Gly Asn Val Val
                500                 505                 510

Thr Ile Asp Gly Arg Gly Phe Gly Ser Thr Lys Gly Thr Val Tyr Phe
                515                 520                 525

Gly Thr Thr Ala Val Thr Gly Ser Ala Ile Thr Ser Trp Glu Asp Thr
        530                 535                 540

Gln Ile Lys Val Thr Ile Pro Pro Val Ala Gly Gly Asp Tyr Ala Val
545                 550                 555                 560

Lys Val Ala Ala Asn Gly Val Asn Ser Asn Ala Tyr Asn Asp Phe Thr
                565                 570                 575

Ile Leu Ser Gly Asp Gln Val Ser Val Arg Phe Val Ile Asn Asn Ala
                580                 585                 590

Thr Thr Ala Leu Gly Glu Asn Ile Tyr Leu Thr Gly Asn Val Ser Glu
                595                 600                 605

Leu Gly Asn Trp Thr Thr Gly Ala Ala Ser Ile Gly Pro Ala Phe Asn
        610                 615                 620

Gln Val Ile His Ala Tyr Pro Thr Trp Tyr Tyr Asp Val Ser Val Pro
625                 630                 635                 640

Ala Gly Lys Gln Leu Glu Phe Lys Phe Phe Lys Lys Asn Gly Ala Thr
                645                 650                 655

Ile Thr Trp Glu Gly Gly Ser Asn His Thr Phe Thr Thr Pro Thr Ser
                660                 665                 670

Gly Thr Ala Thr Val Thr Val Asn Trp Gln
        675                 680
```